United States Patent
Gelfman et al.

(10) Patent No.: US 12,385,064 B2
(45) Date of Patent: Aug. 12, 2025

(54) INTRAVITREAL DOSING FOR DELIVERY OF POLYNUCLEOTIDES TO RETINAL CONES

(71) Applicant: Adverum Biotechnologies, Inc., Redwood City, CA (US)

(72) Inventors: Claire Gelfman, Carlsbad, CA (US); Diana Cepeda, San Diego, CA (US); Ruslan Grishanin, San Francisco, CA (US); Kristina Bender, Redwood City, CA (US); Pallavi Sharma, Sunnyvale, CA (US); Julio Nieves, San Francisco, CA (US)

(*) Notice: Subject to any disclaimer, the term of this patent is extended or adjusted under 35 U.S.C. 154(b) by 225 days.

(21) Appl. No.: 17/705,237

(22) Filed: Mar. 25, 2022

(65) Prior Publication Data

US 2023/0062110 A1    Mar. 2, 2023

Related U.S. Application Data

(60) Provisional application No. 63/306,004, filed on Feb. 2, 2022, provisional application No. 63/166,600, filed on Mar. 26, 2021.

(51) Int. Cl.
*C12N 15/86*    (2006.01)

(52) U.S. Cl.
CPC .... *C12N 15/86* (2013.01); *C12N 2750/14143* (2013.01)

(58) Field of Classification Search
CPC .......... C12N 15/86; C12N 2750/14143; A61K 48/0075
See application file for complete search history.

(56) References Cited

U.S. PATENT DOCUMENTS

| | | | |
|---|---|---|---|
| 11,021,519 B2* | 6/2021 | Chalberg, Jr. | C12N 15/86 |
| 11,118,192 B2* | 9/2021 | Kirn | C12Y 302/01022 |
| 11,510,950 B2* | 11/2022 | Keravala | A61K 9/0048 |
| 2018/0066022 A1* | 3/2018 | Chalberg | C12N 15/861 |
| 2019/0142975 A1* | 5/2019 | Keravala | A61K 48/0075 424/93.2 |
| 2020/0338146 A1* | 10/2020 | Keravala | C12N 15/86 |
| 2021/0069348 A1 | 3/2021 | Kirn | |

OTHER PUBLICATIONS

Khabou H, Garita-Hernandez M, Chaffiol A, Reichman S, Jaillard C, Brazhnikova E, Bertin S, Forster V, Desrosiers M, Winckler C, Goureau O, Picaud S, Duebel J, Sahel JA, Dalkara D. Noninvasive gene delivery to foveal cones for vision restoration. JCI Insight. Jan. 25, 2018;3(2):e96029. (Year: 2018).*

Mancuso K, Hauswirth W W, Li Q, Connor T B, Kuchenbecker J A, Mauck M C, Neitz J, Neitz M, "Gene therapy for red-green colour blindness in adult primates", Nature, Nature Publishing Group UK, London, London, (Oct. 8, 2009), vol. 461, No. 7265, doi:10.1038/NATURE08401, ISSN 0028-0836, pp. 784-788, XP002615068.

* cited by examiner

*Primary Examiner* — Fereydoun G Sajjadi
*Assistant Examiner* — Joel D Levin
(74) *Attorney, Agent, or Firm* — Pierson Ferdinand LLP; Naira Simmons; Daniel Kennedy

(57) ABSTRACT

Provided is the intravitreal dosing of recombinant adeno-associated virus (rAAV)-based gene therapies for the treatment of color vision deficiencies such as Blue Cone Monochromacy (BCM) and Red-Green Color Blindness.

8 Claims, 33 Drawing Sheets
Specification includes a Sequence Listing.

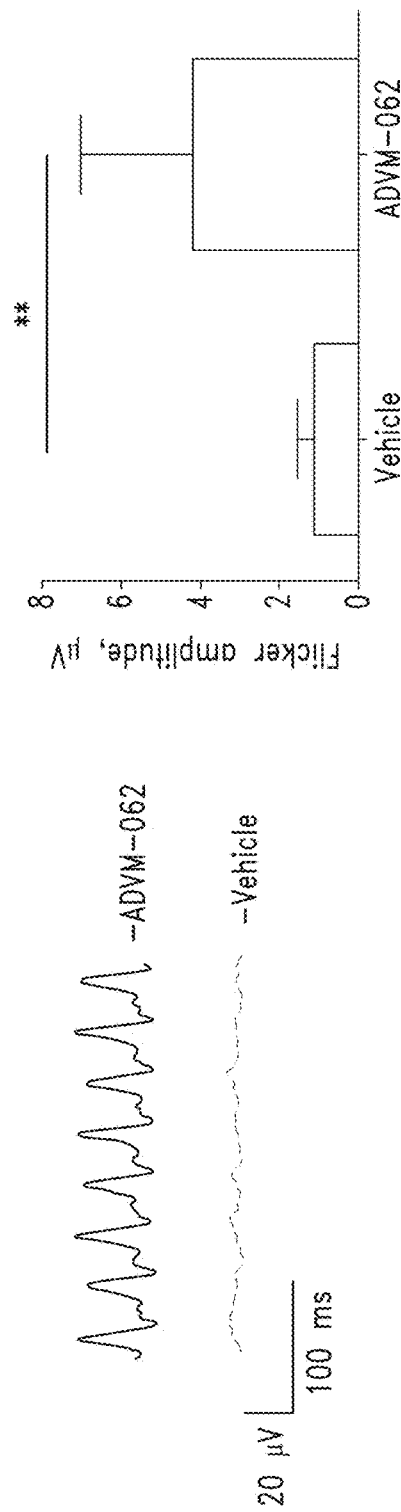
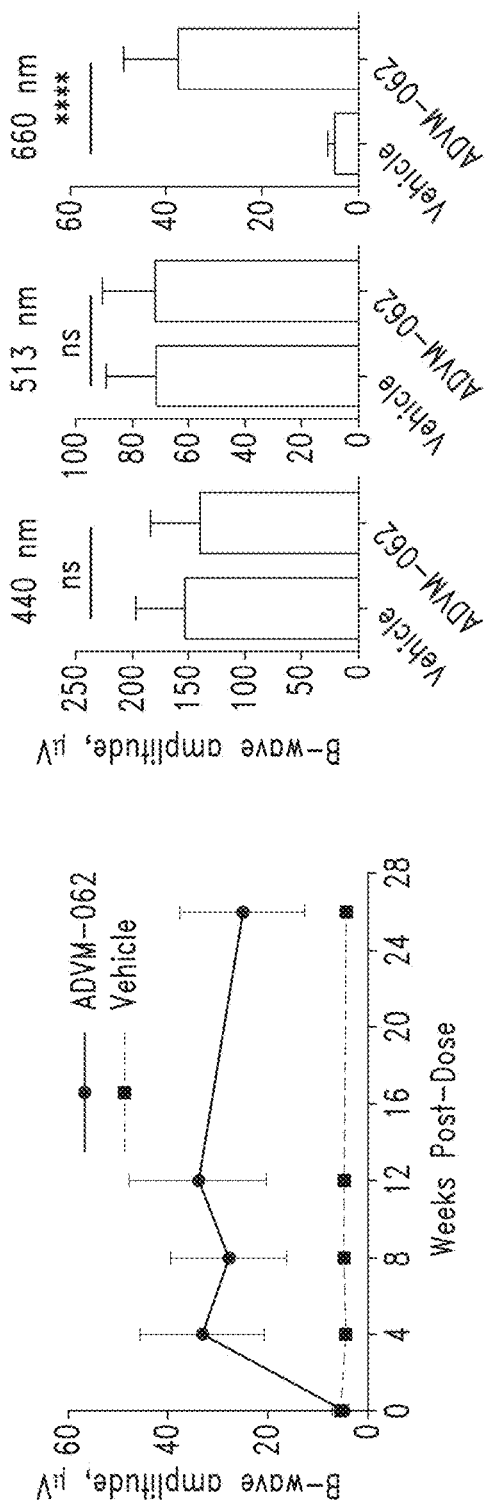
FIG. 3E
FIG. 3F
FIG. 3G
FIG. 3H

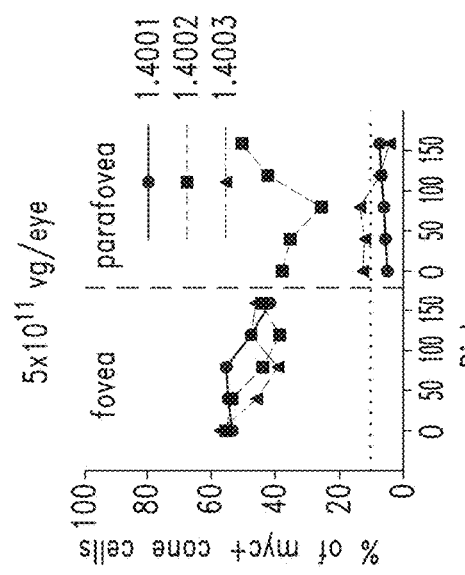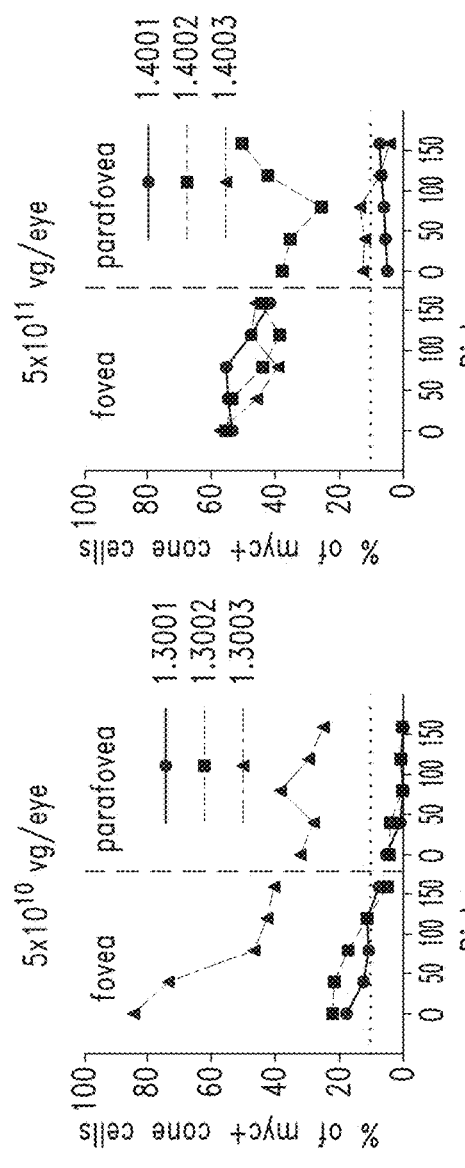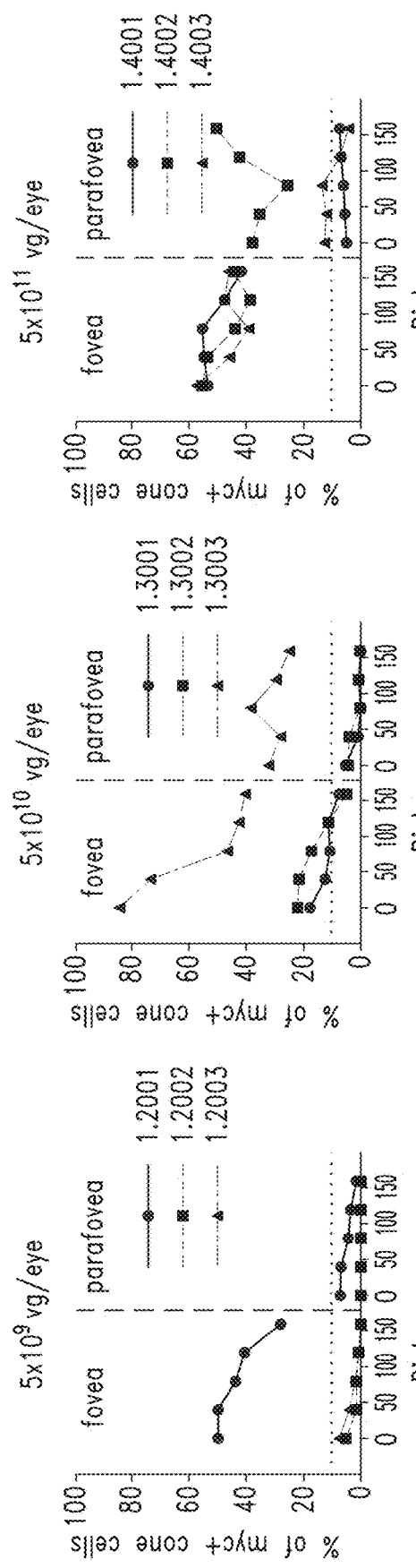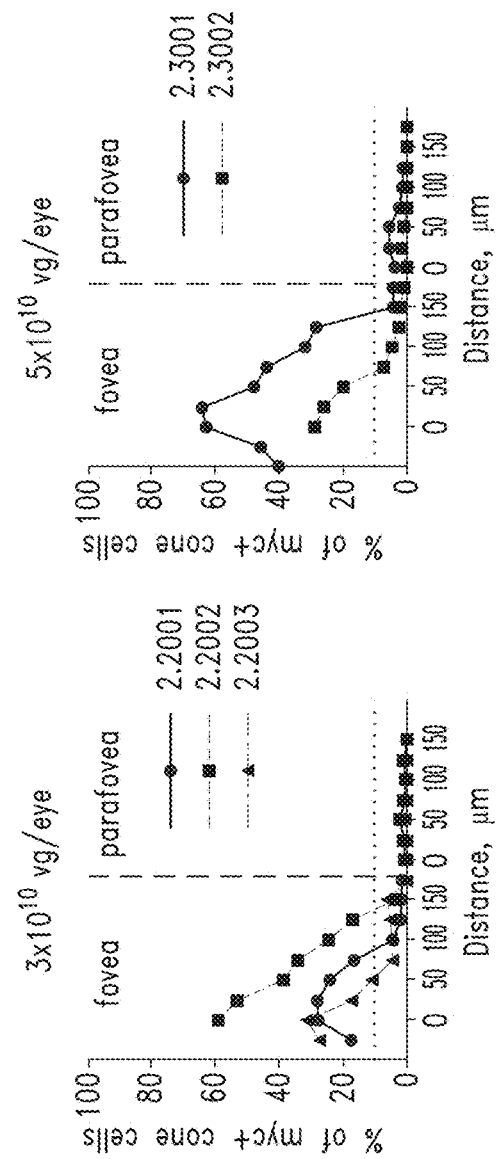
FIG. 5D  FIG. 5E  FIG. 5F  FIG. 5G  FIG. 5H

SEQUENCE LISTING

```
<160> NUMBER OF SEQ ID NOS: 6

<210> SEQ ID NO 1
<211> LENGTH: 745
<212> TYPE: PRT
<213> ORGANISM: Artificial Sequence
<220> FEATURE:
<223> OTHER INFORMATION: Synthetic construct

<400> SEQUENCE: 1

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp Arg
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
```

```
                    210                 215                 220
Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
                275                 280                 285

Cys His Phe Ser Pro Arg Asp Trp Gln Arg Leu Ile Asn Asn Asn Trp
                290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
                435                 440                 445

Asn Thr Pro Ser Gly Thr Thr Thr Gln Ser Arg Leu Gln Phe Ser Gln
                450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
                515                 520                 525

Asp Glu Glu Lys Phe Phe Pro Gln Ser Gly Val Leu Ile Phe Gly Lys
                530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Leu Gly Glu
                580                 585                 590

Thr Thr Arg Pro Ala Arg Gln Ala Ala Thr Ala Asp Val Asn Thr Gln
                595                 600                 605

Gly Val Leu Pro Gly Met Val Trp Gln Asp Arg Asp Val Tyr Leu Gln
                610                 615                 620

Gly Pro Ile Trp Ala Lys Ile Pro His Thr Asp Gly His Phe His Pro
625                 630                 635                 640
```

-continued

Ser Pro Leu Met Gly Gly Phe Gly Leu Lys His Pro Pro Gln Ile
            645             650             655

Leu Ile Lys Asn Thr Pro Val Pro Ala Asn Pro Ser Thr Thr Phe Ser
            660             665             670

Ala Ala Lys Phe Ala Ser Phe Ile Thr Gln Tyr Ser Thr Gly Gln Val
            675             680             685

Ser Val Glu Ile Glu Trp Glu Leu Gln Lys Glu Asn Ser Lys Arg Trp
        690             695             700

Asn Pro Glu Ile Gln Tyr Thr Ser Asn Tyr Asn Lys Ser Val Asn Val
705             710             715             720

Asp Phe Thr Val Asp Thr Asn Gly Val Tyr Ser Glu Pro Arg Pro Ile
            725             730             735

Gly Thr Arg Tyr Leu Thr Arg Asn Leu
            740             745

<210> SEQ ID NO 2
<211> LENGTH: 725
<212> TYPE: PRT
<213> ORGANISM: Artificial Sequence
<220> FEATURE:
<223> OTHER INFORMATION: Synthetic construct

<400> SEQUENCE: 2

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Ala Leu Glu His Asp Lys Ala Tyr Asp
65              70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Thr Gly Lys Arg
    130                 135                 140

Ile Asp Asp His Phe Pro Lys Arg Lys Lys Ala Arg Thr Glu Glu Asp
145                 150                 155                 160

Ser Lys Pro Ser Thr Ser Ser Asp Ala Glu Ala Gly Pro Ser Gly Ser
                165                 170                 175

Gln Gln Leu Gln Ile Pro Ala Gln Pro Ala Ser Ser Leu Gly Ala Asp
            180                 185                 190

Thr Met Ser Ala Gly Gly Gly Pro Leu Gly Asp Asn Asn Gln Gly
        195                 200                 205

Ala Asp Gly Val Gly Asn Ala Ser Gly Asp Trp His Cys Asp Ser Thr
    210                 215                 220

Trp Met Gly Asp Arg Val Val Thr Lys Ser Thr Arg Thr Trp Val Leu
225                 230                 235                 240

Pro Ser Tyr Asn Asn His Gln Tyr Arg Glu Ile Lys Ser Gly Ser Val
                245                 250                 255

```
Asp Gly Ser Asn Ala Asn Ala Tyr Phe Gly Tyr Ser Thr Pro Trp Gly
            260                 265                 270

Tyr Phe Asp Phe Asn Arg Phe His Ser His Trp Ser Pro Arg Asp Trp
        275                 280                 285

Gln Arg Leu Ile Asn Asn Tyr Trp Gly Phe Arg Pro Arg Ser Leu Arg
    290                 295                 300

Val Lys Ile Phe Asn Ile Gln Val Lys Glu Val Thr Val Gln Asp Ser
305                 310                 315                 320

Thr Thr Thr Ile Ala Asn Asn Leu Thr Ser Thr Val Gln Val Phe Thr
                325                 330                 335

Asp Asp Asp Tyr Gln Leu Pro Tyr Val Val Gly Asn Gly Thr Glu Gly
            340                 345                 350

Cys Leu Pro Ala Phe Pro Pro Gln Val Phe Thr Leu Pro Gln Tyr Gly
        355                 360                 365

Tyr Ala Thr Leu Asn Arg Asp Asn Thr Glu Asn Pro Thr Glu Arg Ser
    370                 375                 380

Ser Phe Phe Cys Leu Glu Tyr Phe Pro Ser Lys Met Leu Arg Thr Gly
385                 390                 395                 400

Asn Asn Phe Glu Phe Thr Tyr Asn Phe Glu Glu Val Pro Phe His Ser
                405                 410                 415

Ser Phe Ala Pro Ser Gln Asn Leu Phe Lys Leu Ala Asn Pro Leu Val
            420                 425                 430

Asp Gln Tyr Leu Tyr Arg Phe Val Ser Thr Asn Asn Thr Gly Gly Val
        435                 440                 445

Gln Phe Asn Lys Asn Leu Ala Gly Arg Tyr Ala Asn Thr Tyr Lys Asn
    450                 455                 460

Trp Phe Pro Gly Pro Met Gly Arg Thr Gln Gly Trp Asn Leu Gly Ser
465                 470                 475                 480

Gly Val Asn Arg Ala Ser Val Ser Ala Phe Ala Thr Thr Asn Arg Met
                485                 490                 495

Glu Leu Glu Gly Ala Ser Tyr Gln Val Pro Pro Gln Pro Asn Gly Met
            500                 505                 510

Thr Asn Asn Leu Gln Gly Ser Asn Thr Tyr Ala Leu Glu Asn Thr Met
        515                 520                 525

Ile Phe Asn Ser Gln Pro Ala Asn Pro Gly Thr Thr Ala Thr Tyr Leu
    530                 535                 540

Glu Gly Asn Met Leu Ile Thr Ser Glu Ser Glu Thr Gln Pro Val Asn
545                 550                 555                 560

Arg Val Ala Tyr Asn Val Gly Gly Gln Met Leu Ala His Lys Phe Lys
                565                 570                 575

Ser Gly Asp Ala Pro Thr Thr Gly Thr Tyr Asn Leu Gln Glu Ile Val
            580                 585                 590

Pro Gly Ser Val Trp Met Glu Arg Asp Val Tyr Leu Gln Gly Pro Ile
        595                 600                 605

Trp Ala Lys Ile Pro Glu Thr Gly Ala His Phe His Pro Ser Pro Ala
    610                 615                 620

Met Gly Gly Phe Gly Leu Lys His Pro Pro Met Met Leu Ile Lys
625                 630                 635                 640

Asn Thr Pro Val Pro Gly Asn Ile Thr Ser Phe Ser Asp Val Pro Val
                645                 650                 655

Ser Ser Phe Ile Thr Gln Tyr Ser Thr Gly Gln Val Thr Val Glu Met
            660                 665                 670
```

Glu Trp Glu Leu Lys Lys Glu Asn Ser Lys Arg Trp Asn Pro Glu Ile
            675                 680                 685

Gln Tyr Thr Asn Asn Tyr Asn Asp Pro Gln Phe Val Asp Phe Ala Pro
        690                 695                 700

Asp Ser Thr Gly Glu Tyr Arg Thr Thr Arg Pro Ile Gly Thr Arg Tyr
705                 710                 715                 720

Leu Thr Arg Pro Leu
            725

<210> SEQ ID NO 3
<211> LENGTH: 3918
<212> TYPE: DNA
<213> ORGANISM: Artificial Sequence
<220> FEATURE:
<223> OTHER INFORMATION: Synthetic construct

<400> SEQUENCE: 3

| | | | | | |
|---|---|---|---|---|---|
| gcgcgctcgc | tcgctcactg | aggccgcccg | ggcaaagccc | gggcgtcggg | cgacctttgg | 60 |
| tcgcccggcc | tcagtgagcg | agcgagcgcg | cagagaggga | gtggccaact | ccatcactag | 120 |
| gggttccttg | tagttaatga | ttaacccgcc | atgctactta | tctacgtagc | catgctctag | 180 |
| gatcttcaat | attggccatt | agccatatta | ttcattggtt | atatagcata | aatcaatatt | 240 |
| ggctattggc | cattgcatac | gttgtatcta | tatcataata | tgtacattta | tattggctca | 300 |
| tgtccaatat | gaccgccatg | ttggcattga | ttattgacta | gtcctacagc | agccagggtg | 360 |
| agattatgag | gctgagctga | gaatatcaag | actgtaccga | gtaggggcc | ttggcaagtg | 420 |
| tggagagccc | ggcagctggg | gcagagggcg | gagtacggtg | tgcgtttacg | gacctcttca | 480 |
| aacgaggtag | gaaggtcaga | agtcaaaaag | ggaacaaatg | atgtttaacc | acacaaaaat | 540 |
| gaaaatccaa | tggttggata | tccattccaa | atacacaaag | gcaacggata | agtgatccgg | 600 |
| gccaggcaca | gaaggccatg | cacccgtagg | attgcactca | gagctcccaa | atgcatagga | 660 |
| atagaagggt | gggtgcagga | ggctgagggg | tggggaaagg | gcatgggtgt | tcatgagga | 720 |
| cagagcttcc | gtttcatgca | atgaaaagag | tttggagacg | gatggtggtg | actggactat | 780 |
| acacttacac | acggtagcga | tggtacactt | tgtattatgt | atattttacc | acgatctttt | 840 |
| taaagtgtca | aaggcaaatg | gccaaatggt | tccttgtcct | atagctgtag | cagccatcgg | 900 |
| ctgttagtga | caaagcccct | gagtcaagat | gacagcagcc | cccataactc | ctaatcggct | 960 |
| ctcccgcgtg | gagtcattta | ggagtagtcg | cattagagac | aagtccaaca | tctaatcttc | 1020 |
| caccctggcc | agggccccag | ctggcagcga | gggtgggaga | ctccgggcag | agcagagggc | 1080 |
| gctgacattg | gggcccggcc | tggcttgggt | ccctctggcc | tttccccagg | ggccctcttt | 1140 |
| ccttggggct | ttcttgggcc | gccactgctc | ccgctcctct | cccccatcc | caccccctca | 1200 |
| cccctcgtt | cttcatatcc | ttctctagtg | ctccctccac | tttcatccac | ccttctgcaa | 1260 |
| gagtgtggga | ccacaaatga | gttttcacct | ggcctgggga | cacacgtgcc | cccacaggtg | 1320 |
| ctgagtgact | ttctaggaca | gtaatctgct | ttaggctaaa | atgggacttg | atcttctgtt | 1380 |
| agccctaatc | atcaattagc | agagccggtg | aaggtgcaga | acctaccgcc | tttccaggcc | 1440 |
| tcctcccacc | tctgccacct | ccactctcct | tcctgggatg | tggggctgg | cacacgtgtg | 1500 |
| gcccagggca | ttggtgggat | tgcactgagc | tgggtcatta | gcgtaatcct | ggacaagggc | 1560 |
| agacagggcg | agcggagggc | cagctccggg | gctcaggcaa | ggctggggc | ttccccaga | 1620 |
| cacccccactc | ctcctctgct | ggaccccac | ttcatagggc | acttcgtgtt | ctcaaagggc | 1680 |
| ttccaaatag | catggtggcc | ttggatgccc | agggaagcct | cagagttgct | tatctccctc | 1740 |

```
tagacagaag gggaatctcg gtcaagaggg agaggtcgcc ctgttcaagg ccacccagcc    1800
agctcatggc ggtaatggga caaggctggc cagccatccc accctcagaa gggacccggt    1860
ggggcaggtg atctcagagg aggctcactt ctgggtctca cattcttcca gcaaatccct    1920
ctgagccgcc cccggggget cgcctcagga gcaaggaagc aagggtggg aggaggaggt    1980 ctaagtccca ggcccaatta agagatcaga tggtgtagga tttgggagct tttaaggtga    2040
agaggcccgg gctgatccca ctggccggta taaagcaccg tgaccctcag gtgacgcacc    2100
agggccggct gccgtcgggg acagggcttt ccatagccca ggtaagtatc aaggttacaa    2160
gacaggttta aggagaccaa tagaaactgg gcttgtcgag acagagaaga ctcttgcgtt    2220
tctgataggc acctattggt cttactgaca tccactttgc ctttctctcc acaggcccag    2280
agaggagaca ggccgccacc atggcccagc agtggagcct ccaaaggctc gcaggccgcc    2340
atccgcagga cagctatgag acagcaccc agtccagcat cttcacctac accaacagca    2400
actccaccag aggcccctc gaaggcccga attaccacat cgctcccaga tgggtgtacc    2460
acctcaccag tgtctggatg atctttgtgg tcactgcatc cgtcttcaca aatgggcttg    2520
tgctggcggc caccatgaag ttcaagaagc tgcgccaccc gctgaactgg atcctggtga    2580
acctggcggt cgctgaccta gcagagaccg tcatcgccag cactatcagc attgtgaacc    2640
aggtctctgg ctacttcgtg ctgggccacc ctatgtgtgt cctggagggc tacaccgtct    2700
ccctgtgtgg gatcacaggt ctctggtctc tggccatcat ttcctgggag aggtggctgg    2760
tggtgtgcaa gcccttttggc aatgtgagat ttgatgccaa gctggccatc gtgggcattg    2820
ccttctcctg gatctggtct gctgtgtgga cagccccgcc catctttggt tggagcaggt    2880
actggcccca cggcctgaag acttcatgcg gcccagacgt gttcagcggc agctcgtacc    2940
ccggggtgca gtcttacatg attgtcctca tggtcacctg ctgcatcatc ccactcgcta    3000
tcatcatgct ctgctacctc caagtgtggc tggccatccg agcggtggca aagcagcaga    3060
aagagtctga atccacccag aaggcagaga aggaagtgac gcgcatggtg gtggtgatga    3120
tctttgcgta ctgcgtctgc tggggaccct acacttctt cgcatgcttt gctgctgcca    3180
accctggtta cgccttccac cctttgatgg ctgccctgcc ggcctacttt gccaaaagtg    3240
ccactatcta caaccccgtt atctatgtct ttatgaaccg gcagtttcga aactgcatct    3300
tgcagctttt cgggaagaag gttgacgatg gctctgaact ctccagcgcc tccaaaacgg    3360
aggtctcatc tgtgtcctcg gtatcgcctg catgaggtct gcctcctacc catcccgccc    3420
accgggcctt tggccaccctc tcctttcccc tccttctcc atccctgtaa aataaatgta    3480
atttatcttt gccaaaacca acagacatga taagatacat tgatgagttt ggacaaacca    3540
caactagaat gcagtgaaaa aaatgcttta tttgtgaaat ttgtgatgct attgctttat    3600
ttgtaaccat tataagctgc aataaacaag ttaacaacaa caattgcatt cattttatgt    3660
ttcaggttca gggggagatg tgggaggttt tttaaagcaa gtaaacctc tacaaatgtg    3720 gtaaaatcga taaggatcct agagcatggc tacgtagata agtagcatgg cgggttaatc    3780
attaactaca aggaacccct agtgatggag ttggccactc cctctctgcg cgctcgctcg    3840
ctcactgagg ccgggcgacc aaaggtcgcc cgacgcccgg gctttgcccg gcggcctca    3900 gtgagcgagc gagcgcgc                                                  3918
```

<210> SEQ ID NO 4
<211> LENGTH: 20
<212> TYPE: DNA

```
<213> ORGANISM: Artificial Sequence
<220> FEATURE:
<223> OTHER INFORMATION: Primer

<400> SEQUENCE: 4
ctctcctttc cccctccttc                                               20

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
gcattctagt tgtggtttgt cca                                           23

<210> SEQ ID NO 6
<211> LENGTH: 21
<212> TYPE: DNA
<213> ORGANISM: Artificial Sequence
<220> FEATURE:
<223> OTHER INFORMATION: Probe sequence

<400> SEQUENCE: 6
tgccaaaacc aacagacatg a                                             21
```

INTRAVITREAL DOSING FOR DELIVERY OF POLYNUCLEOTIDES TO RETINAL CONES

CROSS-REFERENCE TO RELATED APPLICATIONS

This application claims priority under 35 U.S.C. § 119(e) to U.S. Provisional Application No. 63/306,004, filed Feb. 2, 2022; and U.S. Provisional Application No. 63/166,600, filed Mar. 26, 2021, each if which is incorporated by reference in its entirety.

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is AVBI_016_02US_ST25.txt. The text file is about 18 KB, was created on Mar. 22, 2022, and is being submitted electronically via EFS-Web.

BACKGROUND

Technical Field

The present disclosure relates to intravitreal dosing of recombinant adeno-associated virus (rAAV)-based gene therapies for the treatment of color vision deficiencies such as Blue Cone Monochromacy (BCM) and Red-Green Color Blindness.

BRIEF SUMMARY

Embodiments of the present disclosure include methods of treating a color vision deficiency in a human subject in need thereof, comprising intravitreally administering to the subject a recombinant adeno-associated virus (rAAV) vector at a dosage ranging from about $1\times10^{10}$ to about $1\times10^{12}$ vector genomes (vg)/eye, wherein the rAAV vector comprises a polynucleotide comprising a human L-opsin protein coding sequence operably linked to an M-opsin promoter sequence, and wherein the rAAV vector comprises an AAV2 capsid variant that transduces foveal cone photoreceptors.

In some embodiments, the polynucleotide comprises, in a 5' to 3' orientation, a 5' AAV2 inverted terminal repeat (ITR), a human locus control region (LCR) enhancer sequence, a truncated M-opsin promoter sequence, a 5' untranslated region (UTR) composed of an M-opsin 5' UTR with an inserted chimeric intron and a strong Kozak sequence, the human L-opsin protein coding sequence, an M-opsin 3' UTR, an SV40 polyadenylation sequence, and a 3' AAV2 ITR. In some embodiments, the AAV2 capsid variant is an AAV2.7m8 capsid or AAV2.5T.LSV1 capsid that comprises, consists, or consists essentially of an amino acid sequence that is at least 80, 85, 90, 95, 98, 99, or 100% identical to the sequence set forth in SEQ ID NO: 1 or 2, and transduces foveal cone photoreceptors. In some embodiments, the polynucleotide comprises, consists, or consists essentially of a sequence that is at least 80, 85, 90, 95, 98, 99, or 100% identical to the sequence set forth in SEQ ID NO: 3, and encodes and expresses a biologically-active human L-opsin protein.

Certain embodiments comprise intravitreally administering the rAAV vector at a dosage of about $5\times10^{10}$, about $1\times10^{11}$, or about $2\times10^{11}$ vg/eye, or optionally about $1\times10^{10}$, about $2\times10^{10}$, about $3\times10^{10}$, about $4\times10^{10}$, about $5\times10^{10}$, about $6\times10^{10}$, about $7\times10^{10}$, about $8\times10^{10}$, about $9\times10^{10}$, about $1\times10^{11}$, about $2\times10^{11}$, about $3\times10^{11}$, about $4\times10^{11}$, about $5\times10^{11}$, about $6\times10^{11}$, about $7\times10^{11}$, about $8\times10^{11}$, about $9\times10^{11}$, or about $1\times10^{12}$ vg/eye.

Particular embodiments comprise intravitreally administering the rAAV vector at a dosage ranging from about $1\times10^{10}$ to about $2\times10^{10}$ vg/eye, about $1\times10^{10}$ to about $3\times10^{10}$ vg/eye, about $1\times10^{10}$ to about $4\times10^{10}$ vg/eye, about $1\times10^{10}$ to about $5\times10^{10}$ vg/eye, about $1\times10^{10}$ to about $6\times10^{10}$ vg/eye, about $1\times10^{10}$ to about $7\times10^{10}$ vg/eye, about $1\times10^{10}$ to about $8\times10^{10}$ vg/eye, about $1\times10^{10}$ to about $9\times10^{10}$ vg/eye, about $1\times10^{10}$ to about $1\times10^{11}$ vg/eye, about $1\times10^{10}$ to about $2\times10^{11}$ vg/eye, about $1\times10^{10}$ to about $3\times10^{11}$ vg/eye, about $1\times10^{10}$ to about $4\times10^{11}$ vg/eye, about $1\times10^{10}$ to about $5\times10^{11}$ vg/eye, about $1\times10^{10}$ to about $6\times10^{11}$ vg/eye, about $1\times10^{10}$ to about $7\times10^{11}$ vg/eye, about $1\times10^{10}$ to about $8\times10^{11}$ vg/eye, about $1\times10^{10}$ to about $9\times10^{11}$ vg/eye, about $1\times10^{10}$ to about $1\times10^{12}$ vg/eye, about $2\times10^{10}$ to about $3\times10^{10}$ vg/eye, about $2\times10^{10}$ to about $4\times10^{10}$ vg/eye, about $2\times10^{10}$ to about $5\times10^{10}$ vg/eye, about $2\times10^{10}$ to about $6\times10^{10}$ vg/eye, about $2\times10^{10}$ to about $7\times10^{10}$ vg/eye, about $2\times10^{10}$ to about $8\times10^{10}$ vg/eye, about $2\times10^{10}$ to about $9\times10^{10}$ vg/eye, about $2\times10^{10}$ to about $1\times10^{11}$ vg/eye, about $2\times10^{10}$ to about $2\times10^{11}$ vg/eye, about $2\times10^{10}$ to about $3\times10^{11}$ vg/eye, about $2\times10^{10}$ to about $4\times10^{11}$ vg/eye, about $2\times10^{10}$ to about $5\times10^{11}$ vg/eye, about $2\times10^{10}$ to about $6\times10^{11}$ vg/eye, about $2\times10^{10}$ to about $7\times10^{11}$ vg/eye, about $2\times10^{10}$ to about $8\times10^{11}$ vg/eye, about $2\times10^{10}$ to about $9\times10^{11}$ vg/eye, about $2\times10^{10}$ to about $1\times10^{12}$ vg/eye, about $3\times10^{10}$ to about $4\times10^{10}$ vg/eye, about $3\times10^{10}$ to about $5\times10^{10}$ vg/eye, about $3\times10^{10}$ to about $6\times10^{10}$ vg/eye, about $3\times10^{10}$ to about $7\times10^{10}$ vg/eye, about $3\times10^{10}$ to about $8\times10^{10}$ vg/eye, about $3\times10^{10}$ to about $9\times10^{10}$ vg/eye, about $3\times10^{10}$ to about $1\times10^{11}$ vg/eye, about $3\times10^{10}$ to about $2\times10^{11}$ vg/eye, about $3\times10^{10}$ to about $3\times10^{11}$ vg/eye, about $3\times10^{10}$ to about $4\times10^{11}$ vg/eye, about $3\times10^{10}$ to about $5\times10^{11}$ vg/eye, about $3\times10^{10}$ to about $6\times10^{11}$ vg/eye, about $3\times10^{10}$ to about $7\times10^{11}$ vg/eye, about $3\times10^{10}$ to about $8\times10^{11}$ vg/eye, about $3\times10^{10}$ to about $9\times10^{11}$ vg/eye, about $3\times10^{10}$ to about $1\times10^{12}$ vg/eye, about $4\times10^{10}$ to about $5\times10^{10}$ vg/eye, about $4\times10^{10}$ to about $6\times10^{10}$ vg/eye, about $4\times10^{10}$ to about $7\times10^{10}$ vg/eye, about $4\times10^{10}$ to about $8\times10^{10}$ vg/eye, about $4\times10^{10}$ to about $9\times10^{10}$ vg/eye, about $4\times10^{10}$ to about $1\times10^{11}$ vg/eye, about $4\times10^{10}$ to about $2\times10^{11}$ vg/eye, about $4\times10^{10}$ to about $3\times10^{11}$ vg/eye, about $4\times10^{10}$ to about $4\times10^{11}$ vg/eye, about $4\times10^{10}$ to about $5\times10^{11}$ vg/eye, about $4\times10^{10}$ to about $6\times10^{11}$ vg/eye, about $4\times10^{10}$ to about $7\times10^{11}$ vg/eye, about $4\times10^{10}$ to about $8\times10^{11}$ vg/eye, about $4\times10^{10}$ to about $9\times10^{11}$ vg/eye, about $4\times10^{10}$ to about $1\times10^{12}$ vg/eye, about $5\times10^{10}$ to about $6\times10^{10}$ vg/eye, about $5\times10^{10}$ to about $7\times10^{10}$ vg/eye, about $5\times10^{10}$ to about $8\times10^{10}$ vg/eye, about $5\times10^{10}$ to about $9\times10^{10}$ vg/eye, about $5\times10^{10}$ to about $1\times10^{11}$ vg/eye, about $5\times10^{10}$ to about $2\times10^{11}$ vg/eye, about $5\times10^{10}$ to about $3\times10^{11}$ vg/eye, about $5\times10^{10}$ to about $4\times10^{11}$ vg/eye, about $5\times10^{10}$ to about $5\times10^{11}$ vg/eye, about $5\times10^{10}$ to about $6\times10^{11}$ vg/eye, about $5\times10^{10}$ to about $7\times10^{11}$ vg/eye, about $5\times10^{10}$ to about $8\times10^{11}$ vg/eye, about $5\times10^{10}$ to about $9\times10^{11}$ vg/eye, about $5\times10^{10}$ to about $1\times10^{12}$ vg/eye, about $6\times10^{10}$ to about $7\times10^{10}$ vg/eye, about $6\times10^{10}$ to about $8\times10^{10}$ vg/eye, about $6\times10^{10}$ to about $9\times10^{10}$ vg/eye, about $6\times10^{10}$ to about $1\times10^{11}$ vg/eye, about $6\times10^{10}$ to about $2\times10^{11}$ vg/eye, about $6\times10^{10}$ to about $3\times10^{11}$ vg/eye, about $6\times10^{10}$ to about $4\times10^{11}$ vg/eye, about $6\times10^{10}$ to about $5\times10^{11}$ vg/eye, about $6\times10^{10}$ to about 6×10¹¹ vg/eye, about 6×10¹⁰ to about 7×10¹¹ vg/eye, about 6×10¹⁰ to about 8×10¹¹ vg/eye, about 6×10¹⁰ to about 9×10¹¹ vg/eye, about 6×10¹⁰ to about 1×10¹² vg/eye, about 7×10¹⁰ to about 8×10¹⁰ vg/eye, about 7×10¹⁰ to about 9×10¹⁰ vg/eye, about 7×10¹⁰ to about 1×10¹¹ vg/eye, about 7×10¹⁰ to about 2×10¹¹ vg/eye, about 7×10¹⁰ to about 3×10¹¹ vg/eye, about 7×10¹⁰ to about 4×10¹¹ vg/eye, about 7×10¹⁰ to about 5×10¹¹ vg/eye, about 7×10¹⁰ to about 6×10¹¹ vg/eye, about 7×10¹⁰ to about 7×10¹¹ vg/eye, about 7×10¹⁰ to about 8×10¹¹ vg/eye, about 7×10¹⁰ to about 9×10¹¹ vg/eye, about 7×10¹⁰ to about 1×10¹² vg/eye, about 8×10¹⁰ to about 9×10¹⁰ vg/eye, about 8×10¹⁰ to about 1×10¹¹ vg/eye, about 8×10¹⁰ to about 2×10¹¹ vg/eye, about 8×10¹⁰ to about 3×10¹¹ vg/eye, about 8×10¹⁰ to about 4×10¹¹ vg/eye, about 8×10¹⁰ to about 5×10¹¹ vg/eye, about 8×10¹⁰ to about 6×10¹¹ vg/eye, about 8×10¹⁰ to about 7×10¹¹ vg/eye, about 8×10¹⁰ to about 8×10¹¹ vg/eye, about 8×10¹⁰ to about 9×10¹¹ vg/eye, about 8×10¹⁰ to about 1×10¹² vg/eye, about 9×10¹⁰ to about 1×10¹¹ vg/eye, about 9×10¹⁰ to about 2×10¹¹ vg/eye, about 9×10¹⁰ to about 3×10¹¹ vg/eye, about 9×10¹⁰ to about 4×10¹¹ vg/eye, about 9×10¹⁰ to about 5×10¹¹ vg/eye, about 9×10¹⁰ to about 6×10¹¹ vg/eye, about 9×10¹⁰ to about 7×10¹¹ vg/eye, about 9×10¹⁰ to about 8×10¹¹ vg/eye, about 9×10¹⁰ to about 9×10¹¹ vg/eye, about 9×10¹⁰ to about 1×10¹² vg/eye, about 1×10¹¹ to about 2×10¹¹ vg/eye, about 1×10¹¹ to about 3×10¹¹ vg/eye, about 1×10¹¹ to about 4×10¹¹ vg/eye, about 1×10¹¹ to about 5×10¹¹ vg/eye, about 1×10¹¹ to about 6×10¹¹ vg/eye, about 1×10¹¹ to about 7×10¹¹ vg/eye, about 1×10¹¹ to about 8×10¹¹ vg/eye, about 1×10¹¹ to about 9×10¹¹ vg/eye, about 1×10¹¹ to about 1×10¹² vg/eye, about 2×10¹¹ to about 3×10¹¹ vg/eye, about 2×10¹¹ to about 4×10¹¹ vg/eye, about 2×10¹¹ to about 5×10¹¹ vg/eye, about 2×10¹¹ to about 6×10¹¹ vg/eye, about 2×10¹¹ to about 7×10¹¹ vg/eye, about 2×10¹¹ to about 8×10¹¹ vg/eye, about 2×10¹¹ to about 9×10¹¹ vg/eye, about 2×10¹¹ to about 1×10¹² vg/eye, about 3×10¹¹ to about 4×10¹¹ vg/eye, about 3×10¹¹ to about 5×10¹¹ vg/eye, about 3×10¹¹ to about 6×10¹¹ vg/eye, about 3×10¹¹ to about 7×10¹¹ vg/eye, about 3×10¹¹ to about 8×10¹¹ vg/eye, about 3×10¹¹ to about 9×10¹¹ vg/eye, about 3×10¹¹ to about 1×10¹² vg/eye, about 4×10¹¹ to about 5×10¹¹ vg/eye, about 4×10¹¹ to about 6×10¹¹ vg/eye, about 4×10¹¹ to about 7×10¹¹ vg/eye, about 4×10¹¹ to about 8×10¹¹ vg/eye, about 4×10¹¹ to about 9×10¹¹ vg/eye, about 4×10¹¹ to about 1×10¹² vg/eye, about 5×10¹¹ to about 6×10¹¹ vg/eye, about 5×10¹¹ to about 7×10¹¹ vg/eye, about 5×10¹¹ to about 8×10¹¹ vg/eye, about 5×10¹¹ to about 9×10¹¹ vg/eye, about 5×10¹¹ to about 1×10¹² vg/eye, about 6×10¹¹ to about 7×10¹¹ vg/eye, about 6×10¹¹ to about 8×10¹¹ vg/eye, about 6×10¹¹ to about 9×10¹¹ vg/eye, about 6×10¹¹ to about 1×10¹² vg/eye, about 7×10¹¹ to about 8×10¹¹ vg/eye, about 7×10¹¹ to about 9×10¹¹ vg/eye, about 7×10¹¹ to about 1×10¹² vg/eye, about 8×10¹¹ to about 9×10¹¹ vg/eye, about 8×10¹¹ to about 1×10¹² vg/eye, or about 9×10¹¹ to about 1×10¹² vg/eye.

Certain embodiments comprise intravitreally administering the rAAV vector at a dosage ranging from about 6×10¹⁰ to about 6×10¹¹ vg/eye. Specific embodiments comprise intravitreally administering the rAAV vector at a dosage of about 6×10¹⁰, about 7×10¹⁰, about 8×10¹⁰, about 9×10¹⁰, about 1×10¹¹ vg/eye, about 2×10¹¹ vg/eye, about 3×10¹¹ vg/eye, about 4×10¹¹ vg/eye, about 5×10¹¹ vg/eye, or about 6×10¹¹ vg/eye. Some embodiments comprise intravitreally administering the rAAV vector at a dosage ranging from about 6×10¹⁰ to about 7×10¹⁰ vg/eye, about 6×10¹⁰ to about 8×10¹⁰ vg/eye, about 6×10¹⁰ to about 9×10¹⁰ vg/eye, about 6×10¹⁰ to about 1×10¹¹ vg/eye, about 6×10¹⁰ to about 2×10¹¹ vg/eye, about 6×10¹⁰ to about 3×10¹¹ vg/eye, about 6×10¹⁰ to about 4×10¹¹ vg/eye, about 6×10¹⁰ to about 5×10¹¹ vg/eye, about 6×10¹⁰ to about 6×10¹¹ vg/eye, about 7×10¹⁰ to about 8×10¹⁰ vg/eye, about 7×10¹⁰ to about 9×10¹⁰ vg/eye, about 7×10¹⁰ to about 1×10¹¹ vg/eye, about 7×10¹⁰ to about 2×10¹¹ vg/eye, about 7×10¹⁰ to about 3×10¹¹ vg/eye, about 7×10¹⁰ to about 4×10¹¹ vg/eye, about 7×10¹⁰ to about 5×10¹¹ vg/eye, about 7×10¹⁰ to about 6×10¹¹ vg/eye, about 8×10¹⁰ to about 9×10¹⁰ vg/eye, about 8×10¹⁰ to about 1×10¹¹ vg/eye, about 8×10¹⁰ to about 2×10¹¹ vg/eye, about 8×10¹⁰ to about 3×10¹¹ vg/eye, about 8×10¹⁰ to about 4×10¹¹ vg/eye, about 8×10¹⁰ to about 5×10¹¹ vg/eye, about 8×10¹⁰ to about 6×10¹¹ vg/eye, about 9×10¹⁰ to about 1×10¹¹ vg/eye, about 9×10¹⁰ to about 2×10¹¹ vg/eye, about 9×10¹⁰ to about 3×10¹¹ vg/eye, about 9×10¹⁰ to about 4×10¹¹ vg/eye, about 9×10¹⁰ to about 5×10¹¹ vg/eye, about 9×10¹⁰ to about 6×10¹¹ vg/eye, about 1×10¹¹ to about 2×10¹¹ vg/eye, about 1×10¹¹ to about 3×10¹¹ vg/eye, about 1×10¹¹ to about 4×10¹¹ vg/eye, about 1×10¹¹ to about 5×10¹¹ vg/eye, about 1×10¹¹ to about 6×10¹¹ vg/eye, about 2×10¹¹ to about 3×10¹¹ vg/eye, about 2×10¹¹ to about 4×10¹¹ vg/eye, about 2×10¹¹ to about 5×10¹¹ vg/eye, about 2×10¹¹ to about 6×10¹¹ vg/eye, about 3×10¹¹ to about 4×10¹¹ vg/eye, about 3×10¹¹ to about 5×10¹¹ vg/eye, about 3×10¹¹ to about 6×10¹¹ vg/eye, about 4×10¹¹ to about 5×10¹¹ vg/eye, about 4×10¹¹ to about 6×10¹¹ vg/eye, or about 5×10¹¹ to about 6×10¹¹ vg/eye.

In certain embodiments, the color vision deficiency is Blue Cone Monochromacy (BCM) or Red-Green Color Blindness. In certain embodiments, the subject prior to treatment has impaired color discrimination, decreased visual acuity, nystagmus, and/or photophobia. In some embodiments, the subject prior to treatment has decreased functional L-opsins and M-opsins, inactive L-cones and M-cones, and decreased foveal vision. In specific embodiments, the subject is characterized by one or more genetic mutations selected from deletions in the locus control region (LCR), nonhomologous recombination between the L- and M-opsin genes and at least one missense point mutation inactivating the residual gene, optionally a C203R mutation, and/or one or more inactivating mutations within the LCR that inhibit expression of the L-opsin and M-opsin genes. In certain embodiments, the subject is a male, optionally about 5, 10, 15, 20, 25, 30, 35, 40, 50, 55, or 60 years of age. In some embodiments, the subject is a pediatric subject, and the dosage is about 2×10¹⁰ vg/eye or 3×10¹⁰ vg/eye.

Certain embodiments comprise treating the subject in both eyes simultaneously (or nearly so), or sequentially, for example, wherein the interval between administering a dosage to the first eye and administering a dosage to the second eye is 1, 2, 3, 4, 5, 6, 7, 8, 9, 10, 11, 12, 13, or 14 days. In some embodiments, the unit dosage administered to the first eye is approximately or substantially equal to the dosage administered to the second eye. In some embodiments, the subject is treated first in a first eye, and subsequently treated in a second eye, and the interval between the first and second does is at least 2 weeks, at least 3 weeks, at least 4 weeks, at least 6 weeks, or at least 8 weeks, and the dosage administered to the second eye is greater than the dosage administered to the first eye, including wherein the second dosage is 1.5×, 2×, 2.5×, 3×, or 3.5× the first dose.

In certain embodiments, intravitreally administering the rAAV vector transduces about or at least about 10% to 85% of the foveal cones in the subject with the polynucleotide encoding and expressing the human L-opsin protein. In some embodiments, intravitreally administering the rAAV vector transduces about or at least about 10, 15, 20, 25, 30, 35, 40, 45, 50, 55, 60, 65, 70, 75, 80, or 85% of the foveal cones in the subject with the polynucleotide encoding and expressing the human L-opsin protein. In certain embodiments, intravitreally administering the rAAV vector improves color discrimination, increases visual acuity, decreases nystagmus, and/or decreases photophobia in the subject.

Particular embodiments comprise intravitreally administering to the subject a single dosage per eye of the rAAV vector.

Also included are intravitreal dosage forms, comprising a recombinant adeno-associated virus (rAAV) vector at a dosage ranging from about $1 \times 10^{10}$ to about $1 \times 10^{12}$ vector genomes (vg)/eye, wherein the rAAV vector comprises a polynucleotide comprising a human L-opsin protein coding sequence operably linked to an M-opsin promoter sequence, and wherein the rAAV vector comprises an AAV2 capsid variant that transduces foveal cone photoreceptors.

In certain embodiments, the polynucleotide comprises, in a 5' to 3' orientation, a 5' AAV2 inverted terminal repeat (ITR), a human locus control region (LCR) enhancer sequence, a truncated M-opsin promoter sequence, a 5' untranslated region (UTR) composed of an M-opsin 5' UTR with an inserted chimeric intron and a strong Kozak sequence, the human L-opsin protein coding sequence, an M-opsin 3' UTR, an SV40 polyadenylation sequence, and a 3' AAV2 ITR. In certain embodiments, the AAV2 capsid variant is an AAV2.7m8 capsid or AAV2.5T.LSV1 capsid that comprises, consists, or consists essentially of an amino acid sequence that is at least 80, 85, 90, 95, 98, 99, or 100% identical to the sequence set forth in SEQ ID NO: 1 or 2, and which transduces foveal cone photoreceptors. In particular embodiments, the polynucleotide comprises, consists, or consists essentially of a sequence that is at least 80, 85, 90, 95, 98, 99, or 100% identical to the sequence set forth in SEQ ID NO: 3, and which encodes and expresses a biologically-active human L-opsin protein.

Some dosage forms comprise the rAAV vector at a dosage of about $5 \times 10^{10}$, about $1 \times 10^{11}$, or about $2 \times 10^{11}$ vg/eye, or optionally about $1 \times 10^{10}$, about $2 \times 10^{10}$, about $3 \times 10^{10}$, about $4 \times 10^{10}$, about $5 \times 10^{10}$, about $6 \times 10^{10}$, about $7 \times 10^{10}$, about $8 \times 10^{10}$, about $9 \times 10^{10}$, about $1 \times 10^{11}$, about $2 \times 10^{11}$, about $3 \times 10^{11}$, about $4 \times 10^{11}$, about $5 \times 10^{11}$, about $6 \times 10^{11}$, about $7 \times 10^{11}$, about $8 \times 10^{11}$, about $9 \times 10^{11}$, or about $1 \times 10^{12}$ vg/eye.

Certain dosage forms comprise the rAAV vector at a dosage ranging from about $1 \times 10^{10}$ to about $2 \times 10^{10}$ vg/eye, about $1 \times 10^{10}$ to about $3 \times 10^{10}$ vg/eye, about $1 \times 10^{10}$ to about $4 \times 10^{10}$ vg/eye, about $1 \times 10^{10}$ to about $5 \times 10^{10}$ vg/eye, about $1 \times 10^{10}$ to about $6 \times 10^{10}$ vg/eye, about $1 \times 10^{10}$ to about $7 \times 10^{10}$ vg/eye, about $1 \times 10^{10}$ to about $8 \times 10^{10}$ vg/eye, about $1 \times 10^{10}$ to about $9 \times 10^{10}$ vg/eye, about $1 \times 10^{10}$ to about $1 \times 10^{11}$ vg/eye, about $1 \times 10^{10}$ to about $2 \times 10^{11}$ vg/eye, about $1 \times 10^{10}$ to about $3 \times 10^{11}$ vg/eye, about $1 \times 10^{10}$ to about $4 \times 10^{11}$ vg/eye, about $1 \times 10^{10}$ to about $5 \times 10^{11}$ vg/eye, about $1 \times 10^{10}$ to about $6 \times 10^{11}$ vg/eye, about $1 \times 10^{10}$ to about $7 \times 10^{11}$ vg/eye, about $1 \times 10^{10}$ to about $8 \times 10^{11}$ vg/eye, about $1 \times 10^{10}$ to about $9 \times 10^{11}$ vg/eye, about $1 \times 10^{10}$ to about $1 \times 10^{12}$ vg/eye, about $2 \times 10^{10}$ to about $3 \times 10^{10}$ vg/eye, about $2 \times 10^{10}$ to about $4 \times 10^{10}$ vg/eye, about $2 \times 10^{10}$ to about $5 \times 10^{10}$ vg/eye, about $2 \times 10^{10}$ to about $6 \times 10^{10}$ vg/eye, about $2 \times 10^{10}$ to about $7 \times 10^{10}$ vg/eye, about $2 \times 10^{10}$ to about $8 \times 10^{10}$ vg/eye, about $2 \times 10^{10}$ to about $9 \times 10^{10}$ vg/eye, about $2 \times 10^{10}$ to about $1 \times 10^{11}$ vg/eye, about $2 \times 10^{10}$ to about $2 \times 10^{11}$ vg/eye, about $2 \times 10^{10}$ to about $3 \times 10^{11}$ vg/eye, about $2 \times 10^{10}$ to about $4 \times 10^{11}$ vg/eye, about $2 \times 10^{10}$ to about $5 \times 10^{11}$ vg/eye, about $2 \times 10^{10}$ to about $6 \times 10^{11}$ vg/eye, about $2 \times 10^{10}$ to about $7 \times 10^{11}$ vg/eye, about $2 \times 10^{10}$ to about $8 \times 10^{11}$ vg/eye, about $2 \times 10^{10}$ to about $9 \times 10^{11}$ vg/eye, about $2 \times 10^{10}$ to about $1 \times 10^{12}$ vg/eye, about $3 \times 10^{10}$ to about $4 \times 10^{10}$ vg/eye, about $3 \times 10^{10}$ to about $5 \times 10^{10}$ vg/eye, about $3 \times 10^{10}$ to about $6 \times 10^{10}$ vg/eye, about $3 \times 10^{10}$ to about $7 \times 10^{10}$ vg/eye, about $3 \times 10^{10}$ to about $8 \times 10^{10}$ vg/eye, about $3 \times 10^{10}$ to about $9 \times 10^{10}$ vg/eye, about $3 \times 10^{10}$ to about $1 \times 10^{11}$ vg/eye, about $3 \times 10^{10}$ to about $2 \times 10^{11}$ vg/eye, about $3 \times 10^{10}$ to about $3 \times 10^{11}$ vg/eye, about $3 \times 10^{10}$ to about $4 \times 10^{11}$ vg/eye, about $3 \times 10^{10}$ to about $5 \times 10^{11}$ vg/eye, about $3 \times 10^{10}$ to about $6 \times 10^{11}$ vg/eye, about $3 \times 10^{10}$ to about $7 \times 10^{11}$ vg/eye, about $3 \times 10^{10}$ to about $8 \times 10^{11}$ vg/eye, about $3 \times 10^{10}$ to about $9 \times 10^{11}$ vg/eye, about $3 \times 10^{10}$ to about $1 \times 10^{12}$ vg/eye, about $4 \times 10^{10}$ to about $5 \times 10^{10}$ vg/eye, about $4 \times 10^{10}$ to about $6 \times 10^{10}$ vg/eye, about $4 \times 10^{10}$ to about $7 \times 10^{10}$ vg/eye, about $4 \times 10^{10}$ to about $8 \times 10^{10}$ vg/eye, about $4 \times 10^{10}$ to about $9 \times 10^{10}$ vg/eye, about $4 \times 10^{10}$ to about $1 \times 10^{11}$ vg/eye, about $4 \times 10^{10}$ to about $2 \times 10^{11}$ vg/eye, about $4 \times 10^{10}$ to about $3 \times 10^{11}$ vg/eye, about $4 \times 10^{10}$ to about $4 \times 10^{11}$ vg/eye, about $4 \times 10^{10}$ to about $5 \times 10^{11}$ vg/eye, about $4 \times 10^{10}$ to about $6 \times 10^{11}$ vg/eye, about $4 \times 10^{10}$ to about $7 \times 10^{11}$ vg/eye, about $4 \times 10^{10}$ to about $8 \times 10^{11}$ vg/eye, about $4 \times 10^{10}$ to about $9 \times 10^{11}$ vg/eye, about $4 \times 10^{10}$ to about $1 \times 10^{12}$ vg/eye, about $5 \times 10^{10}$ to about $6 \times 10^{10}$ vg/eye, about $5 \times 10^{10}$ to about $7 \times 10^{10}$ vg/eye, about $5 \times 10^{10}$ to about $8 \times 10^{10}$ vg/eye, about $5 \times 10^{10}$ to about $9 \times 10^{10}$ vg/eye, about $5 \times 10^{10}$ to about $1 \times 10^{11}$ vg/eye, about $5 \times 10^{10}$ to about $2 \times 10^{11}$ vg/eye, about $5 \times 10^{10}$ to about $3 \times 10^{11}$ vg/eye, about $5 \times 10^{10}$ to about $4 \times 10^{11}$ vg/eye, about $5 \times 10^{10}$ to about $5 \times 10^{11}$ vg/eye, about $5 \times 10^{10}$ to about $6 \times 10^{11}$ vg/eye, about $5 \times 10^{10}$ to about $7 \times 10^{11}$ vg/eye, about $5 \times 10^{10}$ to about $8 \times 10^{11}$ vg/eye, about $5 \times 10^{10}$ to about $9 \times 10^{11}$ vg/eye, about $5 \times 10^{10}$ to about $1 \times 10^{12}$ vg/eye, about $6 \times 10^{10}$ to about $7 \times 10^{10}$ vg/eye, about $6 \times 10^{10}$ to about $8 \times 10^{10}$ vg/eye, about $6 \times 10^{10}$ to about $9 \times 10^{10}$ vg/eye, about $6 \times 10^{10}$ to about $1 \times 10^{11}$ vg/eye, about $6 \times 10^{10}$ to about $2 \times 10^{11}$ vg/eye, about $6 \times 10^{10}$ to about $3 \times 10^{11}$ vg/eye, about $6 \times 10^{10}$ to about $4 \times 10^{11}$ vg/eye, about $6 \times 10^{10}$ to about $5 \times 10^{11}$ vg/eye, about $6 \times 10^{10}$ to about $6 \times 10^{11}$ vg/eye, about $6 \times 10^{10}$ to about $7 \times 10^{11}$ vg/eye, about $6 \times 10^{10}$ to about $8 \times 10^{11}$ vg/eye, about $6 \times 10^{10}$ to about $9 \times 10^{11}$ vg/eye, about $6 \times 10^{10}$ to about $1 \times 10^{12}$ vg/eye, about $7 \times 10^{10}$ to about $8 \times 10^{10}$ vg/eye, about $7 \times 10^{10}$ to about $9 \times 10^{10}$ vg/eye, about $7 \times 10^{10}$ to about $1 \times 10^{11}$ vg/eye, about $7 \times 10^{10}$ to about $2 \times 10^{11}$ vg/eye, about $7 \times 10^{10}$ to about $3 \times 10^{11}$ vg/eye, about $7 \times 10^{10}$ to about $4 \times 10^{11}$ vg/eye, about $7 \times 10^{10}$ to about $5 \times 10^{11}$ vg/eye, about $7 \times 10^{10}$ to about $6 \times 10^{11}$ vg/eye, about $7 \times 10^{10}$ to about $7 \times 10^{11}$ vg/eye, about $7 \times 10^{10}$ to about $8 \times 10^{11}$ vg/eye, about $7 \times 10^{10}$ to about $9 \times 10^{11}$ vg/eye, about $7 \times 10^{10}$ to about $1 \times 10^{12}$ vg/eye, about $8 \times 10^{10}$ to about $9 \times 10^{10}$ vg/eye, about $8 \times 10^{10}$ to about $1 \times 10^{11}$ vg/eye, about $8 \times 10^{10}$ to about $2 \times 10^{11}$ vg/eye, about $8 \times 10^{10}$ to about $3 \times 10^{11}$ vg/eye, about $8 \times 10^{10}$ to about $4 \times 10^{11}$ vg/eye, about $8 \times 10^{10}$ to about $5 \times 10^{11}$ vg/eye, about $8 \times 10^{10}$ to about $6 \times 10^{11}$ vg/eye, about $8 \times 10^{10}$ to about $7 \times 10^{11}$ vg/eye, about $8 \times 10^{10}$ to about $8 \times 10^{11}$ vg/eye, about $8 \times 10^{10}$ to about $9 \times 10^{11}$ vg/eye, about $8 \times 10^{10}$ to about $1 \times 10^{11}$ vg/eye, about $9 \times 10^{10}$ to about $1 \times 10^{11}$ vg/eye, about $9 \times 10^{10}$ to about $2 \times 10^{11}$ vg/eye, about $9 \times 10^{10}$ to about $3 \times 10^{11}$ vg/eye, about $9 \times 10^{10}$ to about $4 \times 10^{11}$ vg/eye, about $9 \times 10^{10}$ to about $5 \times 10^{11}$ vg/eye, about $9 \times 10^{10}$ to about $6 \times 10^{11}$ vg/eye, about $9 \times 10^{10}$ to about $7 \times 10^{11}$ vg/eye, about $9 \times 10^{10}$ to about $8 \times 10^{11}$ vg/eye, about $9 \times 10^{10}$ to about $9 \times 10^{11}$ vg/eye, about $9 \times 10^{10}$ to about $1 \times 10^{12}$ vg/eye, about $1 \times 10^{11}$ to about $2 \times 10^{11}$ vg/eye, about $1 \times 10^{11}$ to about $3 \times 10^{11}$ vg/eye, about $1 \times 10^{11}$ to about $4 \times 10^{11}$ vg/eye, about $1 \times 10^{11}$ to about $5 \times 10^{11}$ vg/eye, about $1 \times 10^{11}$ to about $6 \times 10^{11}$ vg/eye, about $1 \times 10^{11}$ to about $7 \times 10^{11}$ vg/eye, about $1 \times 10^{11}$ to about $8 \times 10^{11}$ vg/eye, about $1 \times 10^{11}$ to about $9 \times 10^{11}$ vg/eye, about $1\times10^{11}$ to about $1\times10^{12}$ vg/eye, about $2\times10^{11}$ to about $3\times10^{11}$ vg/eye, about $2\times10^{11}$ to about $4\times10^{11}$ vg/eye, about $2\times10^{11}$ to about $5\times10^{11}$ vg/eye, about $2\times10^{11}$ to about $6\times10^{11}$ vg/eye, about $2\times10^{11}$ to about $7\times10^{11}$ vg/eye, about $2\times10^{11}$ to about $8\times10^{11}$ vg/eye, about $2\times10^{11}$ to about $9\times10^{11}$ vg/eye, about $2\times10^{11}$ to about $1\times10^{12}$ vg/eye, about $3\times10^{11}$ to about $4\times10^{11}$ vg/eye, about $3\times10^{11}$ to about $5\times10^{11}$ vg/eye, about $3\times10^{11}$ to about $6\times10^{11}$ vg/eye, about $3\times10^{11}$ to about $7\times10^{11}$ vg/eye, about $3\times10^{11}$ to about $8\times10^{11}$ vg/eye, about $3\times10^{11}$ to about $9\times10^{11}$ vg/eye, about $3\times10^{11}$ to about $1\times10^{12}$ vg/eye, about $4\times10^{11}$ to about $5\times10^{11}$ vg/eye, about $4\times10^{11}$ to about $6\times10^{11}$ vg/eye, about $4\times10^{11}$ to about $7\times10^{11}$ vg/eye, about $4\times10^{11}$ to about $8\times10^{11}$ vg/eye, about $4\times10^{11}$ to about $9\times10^{11}$ vg/eye, about $4\times10^{11}$ to about $1\times10^{12}$ vg/eye, about $5\times10^{11}$ to about $6\times10^{11}$ vg/eye, about $5\times10^{11}$ to about $7\times10^{11}$ vg/eye, about $5\times10^{11}$ to about $8\times10^{11}$ vg/eye, about $5\times10^{11}$ to about $9\times10^{11}$ vg/eye, about $5\times10^{11}$ to about $1\times10^{12}$ vg/eye, about $6\times10^{11}$ to about $7\times10^{11}$ vg/eye, about $6\times10^{11}$ to about $8\times10^{11}$ vg/eye, about $6\times10^{11}$ to about $9\times10^{11}$ vg/eye, about $6\times10^{11}$ to about $1\times10^{12}$ vg/eye, about $7\times10^{11}$ to about $8\times10^{11}$ vg/eye, about $7\times10^{11}$ to about $9\times10^{11}$ vg/eye, about $7\times10^{11}$ to about $1\times10^{12}$ vg/eye, about $8\times10^{11}$ to about $9\times10^{11}$ vg/eye, about $8\times10^{11}$ to about $1\times10^{12}$ vg/eye, or about $9\times10^{11}$ to about $1\times10^{12}$ vg/eye.

Some dosage forms comprise the rAAV vector at a dosage ranging from about $6\times10^{10}$ to about $6\times10^{11}$ vg/eye. Specific dosage forms comprise the rAAV vector at a dosage of about $6\times10^{10}$, about $7\times10^{10}$, about $8\times10^{10}$, about $9\times10^{10}$, about $1\times10^{11}$ vg/eye, about $2\times10^{11}$ vg/eye, about $3\times10^{11}$ vg/eye, about $4\times10^{11}$ vg/eye, about $5\times10^{11}$ vg/eye, or about $6\times10^{11}$ vg/eye. Certain dosage forms comprise the rAAV vector at a dosage ranging from about $6\times10^{10}$ to about $7\times10^{10}$ vg/eye, about $6\times10^{10}$ to about $8\times10^{10}$ vg/eye, about $6\times10^{10}$ to about $9\times10^{10}$ vg/eye, about $6\times10^{10}$ to about $1\times10^{11}$ vg/eye, about $6\times10^{10}$ to about $2\times10^{11}$ vg/eye, about $6\times10^{10}$ to about $3\times10^{11}$ vg/eye, about $6\times10^{10}$ to about $4\times10^{11}$ vg/eye, about $6\times10^{10}$ to about $5\times10^{11}$ vg/eye, about $6\times10^{10}$ to about $6\times10^{11}$ vg/eye, about $7\times10^{10}$ to about $8\times10^{10}$ vg/eye, about $7\times10^{10}$ to about $9\times10^{10}$ vg/eye, about $7\times10^{10}$ to about $1\times10^{11}$ vg/eye, about $7\times10^{10}$ to about $2\times10^{11}$ vg/eye, about $7\times10^{10}$ to about $3\times10^{11}$ vg/eye, about $7\times10^{10}$ to about $4\times10^{11}$ vg/eye, about $7\times10^{10}$ to about $5\times10^{11}$ vg/eye, about $7\times10^{10}$ to about $6\times10^{11}$ vg/eye, about $8\times10^{10}$ to about $9\times10^{10}$ vg/eye, about $8\times10^{10}$ to about $1\times10^{11}$ vg/eye, about $8\times10^{10}$ to about $2\times10^{11}$ vg/eye, about $8\times10^{10}$ to about $3\times10^{11}$ vg/eye, about $8\times10^{10}$ to about $4\times10^{11}$ vg/eye, about $8\times10^{10}$ to about $5\times10^{11}$ vg/eye, about $8\times10^{10}$ to about $6\times10^{11}$ vg/eye, about $9\times10^{10}$ to about $1\times10^{11}$ vg/eye, about $9\times10^{10}$ to about $2\times10^{11}$ vg/eye, about $9\times10^{10}$ to about $3\times10^{11}$ vg/eye, about $9\times10^{10}$ to about $4\times10^{11}$ vg/eye, about $9\times10^{10}$ to about $5\times10^{11}$ vg/eye, about $9\times10^{10}$ to about $6\times10^{11}$ vg/eye, about $1\times10^{11}$ to about $2\times10^{11}$ vg/eye, about $1\times10^{11}$ to about $3\times10^{11}$ vg/eye, about $1\times10^{11}$ to about $4\times10^{11}$ vg/eye, about $1\times10^{11}$ to about $5\times10^{11}$ vg/eye, about $1\times10^{11}$ to about $6\times10^{11}$ vg/eye, about $2\times10^{11}$ to about $3\times10^{11}$ vg/eye, about $2\times10^{11}$ to about $4\times10^{11}$ vg/eye, about $2\times10^{11}$ to about $5\times10^{11}$ vg/eye, about $2\times10^{11}$ to about $6\times10^{11}$ vg/eye, about $3\times10^{11}$ to about $4\times10^{11}$ vg/eye, about $3\times10^{11}$ to about $5\times10^{11}$ vg/eye, about $3\times10^{11}$ to about $6\times10^{11}$ vg/eye, about $4\times10^{11}$ to about $5\times10^{11}$ vg/eye, about $4\times10^{11}$ to about $6\times10^{11}$ vg/eye, or about $5\times10^{11}$ to about $6\times10^{11}$ vg/eye.

Some dosage forms are for single use in each eye for treating a color vision deficiency in a human subject in need thereof, as described herein.

BRIEF DESCRIPTION OF THE FIGURES

The present disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIGS. 3A-3J show the effects of IVT dose of ADVM-062 on ERG responses to long-wavelength light in gerbils. (A, B) Representative ERG responses in IVT vehicle-treated (A) and ADVM-062-treated eyes at the dose of $3.9\times10^{11}$ vg/eye (B) to 660 nM LED stimuli of increasing intensity. (C, D) ERG b-wave amplitude in response to increasing intensities of 660 nm light at baseline and 26 weeks post-dose in vehicle control (C) and ADVM-062-treated gerbils (D). ERG responses were elicited by short flashes of 660-nm light at 3 cd·s·m-2. (**: P<0.0001, RM 2 way ANOVA with Sidak's multiple comparisons test). (E) Representative ERG responses of vehicle treated (blue trace) and ADVM-062-treated gerbils (red trace) to 25-Hz 660-nm light flicker. (F) Amplitudes of 25-Hz flicker ERG responses in vehicle and ADVM-062-treated eyes. ( P<0.005 unpaired t-test). (G, H) Durability of augmented ERG sensitivity to 660 nm light in the ADVM-062-treated group, measured up to 26 weeks (G) or 87 weeks post-dose A-G. n=10 or 9 eyes in vehicle- or ADVM-062-dosed groups (1 eye excluded due to an injection procedure-induced cataract), respectively. (H). ADVM-062 did not affect ERG responses to blue (440-nm) or green (530-nm) light but significantly increased ERG b-waves in response to 660-nm (red) light (unpaired t-test, ** P<0.0001; ns—no significance, n=8 eyes in both vehicle and ADVM-062 groups). (I) Dependency of the augmentation of ERG b-wave amplitude on the IVT dose of ADVM-062 in the Mongolian gerbil. Data recorded 28 weeks post-dose are shown. **: P<0.0001 (Ordinary one-way ANOVA with Dunnett's multiple comparisons test). (J) IVT ADVM-062.myc ($5\times10^{10}$ vg/eye) demonstrates cone-specific expression of hOPN1LW-myc transgene expression in the gerbil retina as shown by the overlap in myc immunostaining (green) with a pan-cone marker peanut agglutinin (PNA) (red). Means±SD are shown.

FIGS. 5A-5H show the localization of ADVM-062.myc-driven expression of human L-opsin.myc in cone photoreceptors in an NHP retina (Animal #3003, dosed at $5\times10^{10}$ vg/eye) identified by myc-tag immunofluorescence. (A) Expression of human L-opsin.myc in central retina, with fovea and parafovea demarcated. (B) Magnified area of outer retina within the fovea (in box on A). (C) Expression of human L-opsin.myc in peripheral cones, indicated by the arrowheads. Blue: DAPI, nuclei. Red: cone arrestin, Green: hOPN1LW-myc. (D, H) The density profiles of human L-opsin-positive cones in serial sections cut through the fovea and parafovea along the fovea-optic disk axis, in the individual animals, dosed IVT with ADVM-062.myc. ADVM-062 dose was administered IVT to the middle of vitreous body (D,E,F) at $5\times10^9$ (D), $5\times10^{10}$, or $5\times10^{11}$ (F), $3\times10^{10}$ (G), or to posterior pole of the eye, aiming closer to optic disc region (G,H), at $3\times10^{10}$ (G), or $5\times10^{10}$ (H) vg/eye. X axis as a distance from a transverse section cut through the avascular zone in the direction from the foveola to the superior pole. Expression has been quantified as a percentage of hL-opsin.myc positive cone outer segments identified by cone-arrestin counterstaining, in a 500-µm region centered over the foveal avascular zone (FAZ). Parafoveal cone cell counts were assessed by selecting a 500-µm region starting from the margins of the FAZ and extending out towards the temporal and nasal parafoveal periphery.

FIGS. 7A-1 to 7A-4 and FIGS. 7B-1 to 7B-4 show the ocular inflammation findings in NHPs treated with vehicle or ADVM-062 at $5\times10^9$, $5\times10^{10}$, and $5\times10^{11}$ vg/eye. Vitreous cell infiltrates, vitreous haze, aqueous cell infiltrates, and aqueous flare were observed and showed dose-dependency on ADVM-062.

FIGS. 13-1 to 13-4 show IVT ADVM-062 ocular tolerability. NHP eyes were bilaterally IVT injected with vehicle, or ADVM-062 at $5\times10^{10}$, $1\times10^{11}$ or $3\times10^{11}$ vg/eye. The parameters scored by the Hackett-McDonald irritation and inflammation scoring system are shown: vitreous cells, vitreous haze, aqueous cells and aqueous flare. The eye exams were performed using slit-lamp biomicroscopy and indirect ophthalmoscopy. The inflammatory response was limited to mild and transient dose-dependent vitreous cell infiltrates. No aqueous cells, aqueous flare or vitreous haze were detected at any timepoint of the study. Vehicle injection resulted in a low grade (1+) transient inflammatory response in one eye of one out of two vehicle treated animals, considered to be related to a procedure. The observed inflammatory responses were considered non-adverse.

DETAILED DESCRIPTION

Figure 1:
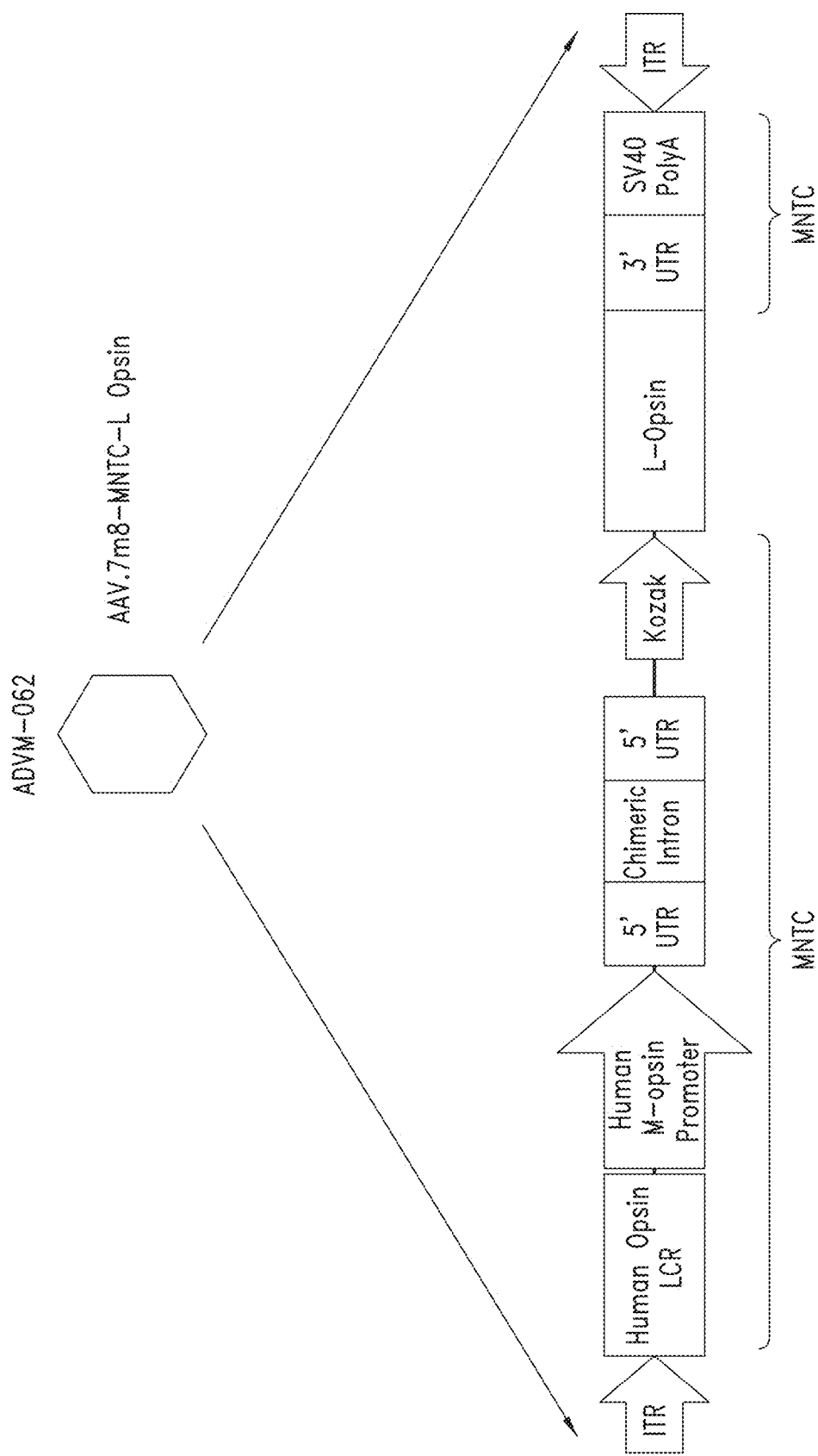
FIG. 1 shows the design of the ADVM-062 vector genome. The vector genome includes the MNTC expression cassette (see U.S. Pat. No. 10,000,741) flanked by 5' and 3' inverted terminal repeats (ITRs). The MNTC expression cassette includes a human LCR enhancer sequence, a truncated M-opsin promoter sequence, a 5' untranslated region (UTR) based on the M-opsin 5' UTR split into two by the insertion of a chimeric intron and a strong Kozak sequence to drive expression of the human L-opsin gene, an M-opsin 3' UTR, and an SV40 polyadenylation sequence. The MNTC-L Opsin cassette, flanked by the AAV2 inverted ITRs, is packaged in the AAV2.7m8 capsid variant.
Figure 2A:
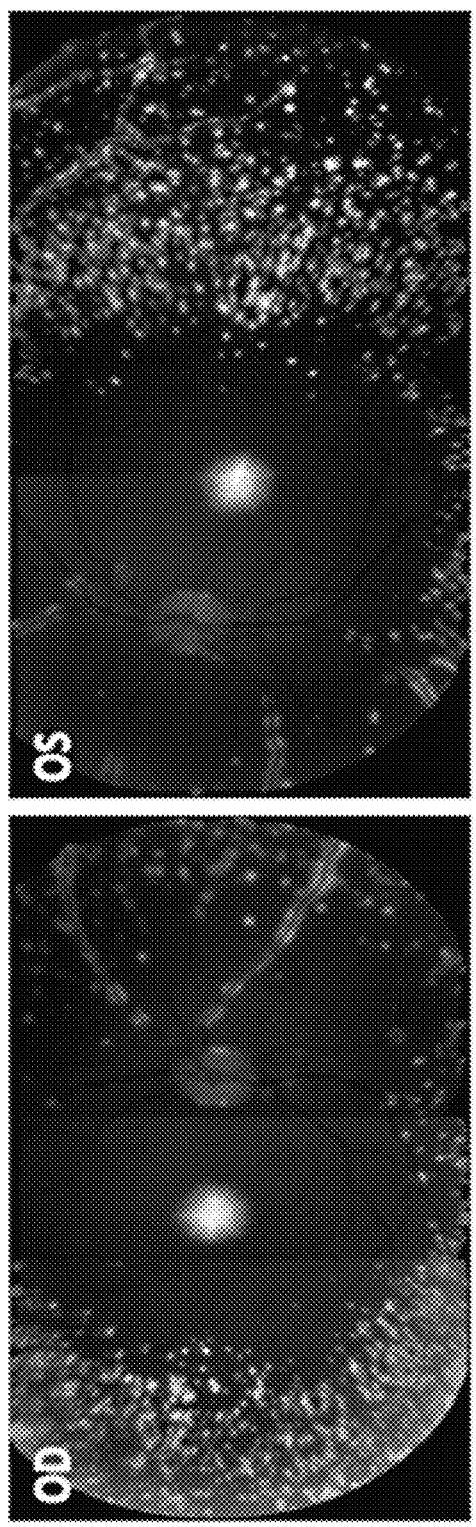
FIGS. 2A-2B show that the MNTC regulatory cassette drives pronounced and abundant expression in non-human primate (NHP) cone photoreceptors. (A) Composite fundus autofluorescence images acquired by SLO shows GFP expression in retinas of both eyes of two NHPs (K271 and K472) transduced with $5\times10^{11}$ vg/eye of AAV2.7m8-MNTC-GFP at 12 weeks post-intravitreal injection. (B) AAV2.7m8-MNTC-GFP results in cone-specific transgene expression in the NHP retina (animal K271) in the fovea (left), mid-periphery (middle) and periphery (right) following intravitreal (IVT) administration as shown by the overlap in GFP (green) with L/M-opsin and calbindin (marker of peripheral and perifoveal cones, magenta).
Figure 2B:
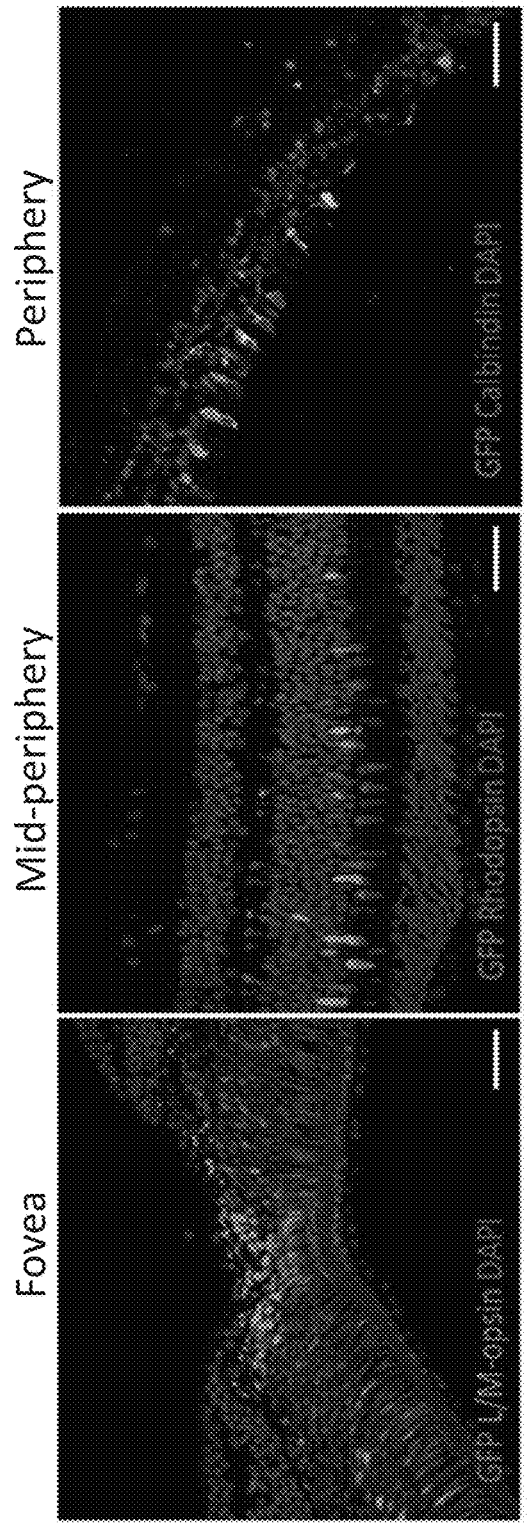

Methods and dosage forms are provided for optimal intravitreal delivery of a polynucleotide to cone photoreceptors. Aspects of the methods include injecting a recombinant adeno-associated virus comprising the polynucleotide of interest into the vitreous of the eye. These methods and compositions find particular use in treating color vision deficiencies. These and other objects, advantages, and features of the invention will become apparent to those persons skilled in the art upon reading the details of the compositions and methods as more fully described herein.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described.

All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

It must be noted that as used herein and in the appended claims, the singular forms "a", "an", and "the" include plural referents unless the context clearly dictates otherwise. Thus, for example, reference to "a cell" includes a plurality of such cells and reference to "the polynucleotide" includes reference to one or more polynucleotides and equivalents thereof, e.g., nucleic acid sequences, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

A "vector" as used herein refers to a macromolecule or association of macromolecules that comprises or associates with a polynucleotide and which can be used to mediate delivery of the polynucleotide to a cell. Illustrative vectors include, for example, plasmids, viral vectors (virus or the viral genome thereof), liposomes, and other gene delivery vehicles.

By a "virus" it is meant a viral particle comprising a viral capsid and a viral genome. For example, an adeno-associated virus refers to a viral particle comprising at least one adeno-associated virus capsid protein or variant thereof and an encapsidated adeno-associated virus vector genome or variant thereof.

By a viral "capsid" it is meant the protein shell of a virus. Viral capsids typically comprise several oligomeric structural subunits made of protein called protomers. The capsid encloses, or "encapsidates", the genetic material, or "genome", of the virus. In some viruses, the capsid is enveloped, meaning that the capsid is coated with a lipid membrane known as a viral envelope.

By a viral "genome" (referred to interchangeably herein as "viral genome", "viral vector DNA" and "viral DNA"), it is meant a polynucleotide sequence comprising at least one, and generally two, viral terminal repeats (e.g., inverted terminal repeats (ITRs), long terminal repeats (LTR)) at its ends.

By a "recombinant viral genome" it is meant a viral genome comprising a heterologous nucleic acid sequence and at least one, and generally two, viral terminal repeats at its ends. By a "recombinant virus" it is meant a viral particle comprising a recombinant viral genome.

As used herein, the term "heterologous" means derived from a genotypically distinct entity from that of the rest of the entity to which it is being compared. For example, a polynucleotide introduced by genetic engineering techniques into a plasmid or vector derived from a different species, e.g., a viral genome, is a heterologous polynucleotide. As another example, a promoter removed from its native coding sequence and operatively linked to a coding sequence with which it is not naturally found linked is a heterologous promoter. As a third example, a heterologous gene product, e.g., RNA, protein, is a gene product not normally encoded by a cell in which it is being expressed.

The term "replication defective" as used herein relative to the viruses of the disclosure refers to a virus that cannot independently replicate and package its genome. For example, when a cell of a subject is infected with recombinant virions, the heterologous gene is expressed in the infected cells; however, due to the fact that the infected cells lack AAV rep and cap genes and accessory function genes, the recombinant virus is not able to replicate further.

The term "AAV" is an abbreviation for adeno-associated virus. When used herein, the term AAV may be used to refer to the virus itself or derivatives thereof, e.g., the viral capsid, the viral genome, and the like. The term "AAV" encompasses all subtypes, both naturally occurring and recombinant forms, and variants thereof except where required otherwise.

By "naturally occurring" or "wild-type" AAV it is meant any adeno-associated virus or derivative thereof comprising a viral capsid that consists of viral capsid proteins that occur in nature. Non-limiting examples of naturally occurring AAV include AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), AAV9, AAV10, AAV11, AAV12, rh10, avian AAV, bovine AAV, canine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, etc.

By an "AAV variant" or a "variant AAV" it is meant to include an AAV viral particle comprising a variant, or mutant, AAV capsid protein. Examples of variant AAV capsid proteins include AAV capsid proteins comprising at least one amino acid difference (e.g., amino acid substitution, amino acid insertion, amino acid deletion) relative to a corresponding parental AAV capsid protein, i.e., an AAV capsid protein from which it was derived, a wild type AAV capsid protein, etc., where the variant AAV capsid protein does not consist of an amino acid sequence present in a naturally occurring AAV capsid protein. In addition to differing structurally, i.e., at the sequence level, from the corresponding parental AAV, the AAV variant may differ functionally from the corresponding parental AAV. Put another way, the variant capsid protein comprising the at least one amino acid difference relative to a corresponding parental AAV capsid protein may confer functional characteristics on the AAV variant that are not possessed by the corresponding parental AAV. For example, the AAV variant may have a different cellular tropism, i.e., a different affinity for and/or ability to infect a particular type of cell, e.g., the AAV variant may bind to a cell, e.g., a retinal cell, with an increased (or decreased) affinity than the parental AAV, and/or infect/transduce a cell, e.g., a retinal cell, with an increased (or decreased) efficiency than the parental AAV such that more (or less) cells of a cell population is transduced/infected with the same titer of viral particles. As another example, the AAV variant may have a greater (or lesser) affinity for antibodies produced by the host animal, e.g., the AAV variant may bind with greater (or lesser) affinity to neutralizing antibodies and be cleared from the host tissue to a greater (or lesser) extent.

By "recombinant AAV", or "rAAV" it is meant to include any AAV that comprises a heterologous polynucleotide sequence in its viral genome. In general, the heterologous polynucleotide is flanked by at least one, and generally by two naturally occurring or variant AAV inverted terminal repeat sequences (ITRs). The term rAAV vector encompasses both rAAV vector particles and rAAV vector plasmids. Thus, for example, an rAAV that comprises a heterologous polynucleotide sequence would be an rAAV that includes a nucleic acid sequence not normally included in a naturally-occurring, wild-type AAV, for example, a transgene (e.g., a non-AAV RNA-coding polynucleotide sequence, non-AAV protein-coding polynucleotide sequence), a non-AAV promoter sequence, a non-AAV poly-adenylation sequence, etc.

As used herein, the term "expression vector" refers to a vector comprising a region which encodes a gene product of interest, and is used for effecting the expression of a gene product in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

As used herein, the term "expression" refers to the transcription and/or translation of a coding sequence, e.g., an endogenous gene, a heterologous gene, in a cell.

As used herein, the terms "gene" or "coding sequence" refer to a polynucleotide sequence that encodes a gene product, and encompasses both naturally occurring polynucleotide sequences and cDNA. A gene may or may not include regions preceding and following the coding region, e.g., 5' untranslated (5' UTR) or "leader" sequences and 3' UTR or "trailer" sequences, or intervening sequences (introns) between individual coding segments (exons).

As used herein, the term "gene product" refers the desired expression product of a polynucleotide sequence such as a polypeptide, peptide, protein or RNA including, for example, a ribozyme, short interfering RNA (siRNA), miRNA or small hairpin RNA (shRNA). The terms "polypeptide," "peptide," and "protein" are used interchangeably herein to refer to polymers of amino acids of any length. The terms also encompass an amino acid polymer that has been modified; for example, disulfide bond formation, glycosylation, lipidation, phosphorylation, or conjugation with a labeling component.

As used herein, the terms "operatively linked" or "operably linked" refers to a juxtaposition of genetic elements on a single polynucleotide, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained. The combination of control elements, e.g., promoter, enhancer(s), etc. and a gene or genes to which they are operably linked for expression is sometimes referred to as an "expression cassette," a large number of which are known and available in the art or can be readily constructed from components that are available in the art.

By a "promoter" it is generally meant a DNA sequence that directs the binding of RNA polymerase and thereby promotes RNA synthesis, i.e., a minimal sequence sufficient to direct transcription. Promoters and corresponding protein or polypeptide expression may be ubiquitous, meaning strongly active in a wide range of cells, tissues and species or cell-type specific, tissue-specific, or species-specific. Promoters may be "constitutive," meaning continually active, or "inducible," meaning the promoter can be activated or deactivated by the presence or absence of biotic or abiotic factors.

By an "enhancer" it is generally meant a cis-acting regulatory element that stimulates, i.e., promotes or enhances, transcription of an adjacent genes. By a "silencer" it is meant a cis-acting regulatory element that inhibits, i.e., reduces or suppresses, transcription of an adjacent gene, e.g., by actively interfering with general transcription factor assembly or by inhibiting other regulatory elements, e.g., enhancers, associated with the gene. Enhancers can function (i.e., can be associated with a coding sequence) in either orientation, over distances of up to several kilobase pairs (kb) from the coding sequence and from a position downstream of a transcribed region. Enhancer sequences influence promoter-dependent gene expression and may be located in the 5' or 3' regions of the native gene. Enhancer sequences may or may not be contiguous with the promoter sequence. Likewise, enhancer sequences may or may not be immediately adjacent to the gene sequence. For example, an enhancer sequence may be several thousand basepairs from the promoter and/or gene sequence.

A "termination signal sequence" within the meaning of the invention may be any genetic element that causes RNA polymerase to terminate transcription, such as for example a polyadenylation signal sequence. A polyadenylation signal sequence is a recognition region necessary for endonuclease cleavage of an RNA transcript that is followed by the polyadenylation consensus sequence AATAAA. A polyadenylation signal sequence provides a "polyA site", i.e., a site on a RNA transcript to which adenine residues will be added by post-transcriptional polyadenylation.

The terms "identical" or percent "identity" in the context of two or more nucleotide sequences that are the same or have a specified percentage of amino acid residues or nucleotides that are the same, when compared and aligned for maximum correspondence, as measured using one of the sequence comparison algorithms described herein, e.g., the Smith-Waterman algorithm, or by visual inspection.

As used herein, the term "sequence identity" refers to the degree of identify between nucleotides in two or more aligned sequences, when aligned using a sequence alignment program. The term "% homology" is used interchangeably herein with the term "% identity" herein and refers to the level of nucleic acid or amino acid sequence identity between two or more aligned sequences, when aligned using a sequence alignment program. For example, as used herein, 80% homology means the same thing as 80% sequence identity determined by a defined algorithm, and accordingly a homologue of a given sequence has greater than 80% sequence identity over a length of the given sequence. Sequence identity may be determined by aligning sequences using any of a number of publicly available alignment algorithm tools, e.g., the local homology algorithm of Smith & Waterman, Adv. Appl. Math. 2: 482 (1981), the homology alignment algorithm of Needleman & Wunsch, J Mol. Biol. 48: 443 (1970), the search for similarity method of Pearson & Lipman, Proc. Nat'l. Acad. Sci. USA 85: 2444 (1988), computerized implementations of these algorithms (GAP, BESTFIT, FASTA, and TFASTA in the Wisconsin Genetics Software Package, Genetics Computer Group, 575 Science Dr., Madison, Wis.), by the BLAST algorithm, Altschul et al., J Mol. Biol. 215: 403-410 (1990), with software that is publicly available through the National Center for Biotechnology Information (www.ncbi.nlm.nih.gov/), or by visual inspection (see generally, Ausubel et al., infra).

The terms "complement" and "complementary" refer to two antiparallel nucleotide sequences capable of pairing with one another upon formation of hydrogen bonds between the complementary base residues in the antiparallel nucleotide sequences.

The term "native", when used in the context of a polynucleotide or polypeptide herein, refers to a polynucleotide or polypeptide sequence that is found in nature; i.e., that is present in the genome of a wild-type virus or cell.

The term "variant", when used in the context of a polynucleotide or polypeptide herein, refers to a mutants of a native polynucleotide or polypeptide having less than 100% sequence identity with the native sequence or any other native sequence. Such variants may comprise one or more substitutions, deletions, or insertions in the corresponding native gene or gene product sequence. The term "variant" also includes fragments of the native gene or gene product, and mutants thereof, e.g., fragments comprising one or more substitutions, deletions, or insertions in the corresponding native gene or gene product fragment. In some embodiments, the variant retains a functional activity of the native gene product, e.g., ligand binding, receptor binding, protein signaling, etc., as known in the art.

The term "fragment," when referring to a recombinant protein or polypeptide of the invention means a polypeptide having an amino acid sequence which is the same as part of, but not all of, the amino acid sequence of the corresponding full length protein or polypeptide, which retains at least one of the functions or activities of the corresponding full length protein or polypeptide. The fragment preferably includes at least 20-100 contiguous amino acid residues of the full length protein or polypeptide.

As used herein, the terms "biological activity" and "biologically active" refer to the activity attributed to a particular gene product, e.g., RNA or protein, in a cell line in culture or in vivo.

The terms "modulating" and "altering" include "increasing," "enhancing" or "stimulating," as well as "decreasing" or "reducing," typically in a statistically significant or a physiologically significant amount or degree relative to a control. An "increased," "stimulated" or "enhanced" amount is typically a "statistically significant" amount, and may include an increase that is 1.1, 1.2, 1.5, 2, 3, 4, 5, 6, 7, 8, 9, 10, 15, 20, 30, 40, 50, 60, 70, 80, 90, 100 or more times (e.g., 500, 1000 times) (including all integers and ranges in between e.g., 1.5, 1.6, 1.7, 1.8, etc.) the amount produced by no composition (e.g., the absence of agent) or a control composition. A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease (including all integers and ranges in between) in the amount produced by no composition (e.g., the absence of an agent) or a control composition. Examples of comparisons and "statistically significant" amounts are described herein.

"Substantially" or "essentially" means nearly totally or completely, for instance, 95%, 96%, 97%, 98%, 99% or greater of some given quantity.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

The terms "administering" or "introducing", as used herein refer to contacting a cell, tissue, or subject with a vector for the purposes of delivering a polynucleotide to the cell or to cells and or organs of the subject. Such administering or introducing may take place in vivo, in vitro, or ex vivo. A vector for expression of a gene product may be introduced into a cell by transfection, which typically means insertion of heterologous DNA into a cell by physical means (e.g., calcium phosphate transfection, electroporation, microinjection or lipofection); infection, which typically refers to introduction by way of an infectious agent, i.e., a virus; or transduction, which typically means stable infection of a cell with a virus or the transfer of genetic material from one microorganism to another by way of a viral agent (e.g., a bacteriophage).

"Transformation" or "transfection" as used herein refers to the delivery of a heterologous DNA to the interior of a cell, e.g., a mammalian cell, an insect cell, a bacterial cell, etc. by a vector. A vector used to "transform" a cell may be a plasmid, minicircle DNA, or other vehicle. Typically, a cell is referred to as "transduced", "infected"; "transfected" or "transformed" dependent on the means used for administration, introduction or insertion of heterologous DNA (i.e., the vector) into the cell. The terms "transfected" and "transformed" are used interchangeably herein to refer to the introduction of heterologous DNA by non-viral methods, e.g., electroporation, calcium chloride transfection, lipofection, etc., e.g., as when preparing the subject viral vectors for use in the subject methods. The terms "transduced" and "infected" are used interchangeably herein to refer to introduction of the heterologous DNA to the cell in the context of a viral particle.

The term "host cell", as used herein refers to a cell which has been transduced, infected, transfected or transformed with a vector. The vector may be a plasmid, a viral particle, a phage, etc. The culture conditions, such as temperature, pH, and the like, are those previously used with the host cell selected for expression, and will be apparent to those skilled in the art. It will be appreciated that the term "host cell" refers to the original transduced, infected, transfected or transformed cell and progeny thereof.

As used herein, a "therapeutic" gene refers to a gene that, when expressed, confers a beneficial effect on the cell or tissue in which it is present, or on a mammal in which the gene is expressed. Examples of beneficial effects include amelioration of a sign or symptom of a condition or disease, prevention or inhibition of a condition or disease, or conferral of a desired characteristic. Therapeutic genes include genes that correct a genetic deficiency in a cell or mammal.

The terms "treatment", "treating" and the like are used herein to generally mean obtaining a desired pharmacologic and/or physiologic effect. The effect may be prophylactic in terms of completely or partially preventing a disease or symptom thereof, e.g., reducing the likelihood that the disease or symptom thereof occurs in the subject, and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired, including, but not limited to, human and non-human primates, including simians and humans; mammalian sport animals (e.g., horses); mammalian farm animals (e.g., sheep, goats, etc.); mammalian pets (dogs, cats, etc.); and rodents (e.g., mice, rats, etc.); particularly humans.

The terminology used herein is for the purpose of describing particular embodiments only and is not intended to be limiting of the invention. As used herein, the singular forms "a", "an", and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

By "comprising" it is meant that the recited elements are required in, for example, the composition, method, dosage form, kit, etc., but other elements may be included to form the, for example, composition, method, dosage form, kit, etc. within the scope of the claim. For example, an expression cassette "comprising" a gene encoding a therapeutic polypeptide operably linked to a promoter is an expression cassette that may include other elements in addition to the gene and promoter, e.g., poly-adenylation sequence, enhancer elements, other genes, linker domains, etc.

By "consisting essentially of", it is meant a limitation of the scope of the, for example, composition, method, kit, etc., described to the specified materials or steps that do not materially affect the basic and novel characteristic(s) of the, for example, composition, method, dosage form, kit, etc. For example, an expression cassette "consisting essentially of" a gene encoding a therapeutic polypeptide operably linked to a promoter and a polyadenylation sequence may include additional sequences, e.g., linker sequences, so long as they do not materially affect the transcription or translation of the gene. As another example, a variant polypeptide fragment "consisting essentially of" a recited sequence has the amino acid sequence of the recited sequence plus or minus about 10 amino acid residues at the boundaries of the sequence based upon the full length naïve polypeptide from which it was derived, e.g., 10, 9, 8, 7, 6, 5, 4, 3, 2 or 1 residue less than the recited bounding amino acid residue, or 1, 2, 3, 4, 5, 6, 7, 8, 9, or 10 residues more than the recited bounding amino acid residue.

By "consisting of", it is meant the exclusion from the composition, method, dosage form, or kit of any element, step, or ingredient not specified in the claim. For example, an expression cassette "consisting of" a gene encoding a therapeutic polypeptide operably linked to a promoter and a polyadenylation sequence consists only of the promoter, polynucleotide sequence encoding the therapeutic polypeptide, and polyadenlyation sequence. As another example, a polypeptide "consisting of" a recited sequence contains only the recited amino acid sequence.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "wild-type" refers to a gene or gene product (e.g., a polypeptide) that is most frequently observed in a population and is thus arbitrarily designed the "normal" or "wild-type" form of the gene.

Each embodiment in this specification is to be applied to every other embodiment unless expressly stated otherwise.

Methods and Dosage Forms

Provided herein are methods and dosage forms for optimal delivery a polynucleotide to cone photoreceptors. Generally, embodiments of the present disclosure relate to dosage forms and methods of treating a color vision deficiency in a human subject in need thereof, comprising intravitreally administering to the subject a recombinant adeno-associated virus (AAV) vector at a dosage ranging from about $1 \times 10^{10}$ to about $1 \times 10^{12}$ vector genomes (vg)/eye. In particular embodiments, the AAV vector has a polynucleotide comprising a human L-opsin protein coding sequence operably linked to an M-opsin promoter sequence, and an AAV capsid variant that transduces foveal cone photoreceptors.

As discussed herein, cone photoreceptors, referred to interchangeably herein as "cone cells", "retinal cones", and most simply, "cones," are one of two subtypes of photoreceptor cells in the retina of the eye, the other being rod photoreceptors. Cone photoreceptors may be readily distinguished from rod photoreceptors by a number of physical, biochemical, and functional characteristics. For example, cone photoreceptors comprise an outer segment region that is shaped like a cone, whereas rod photoreceptors comprise an outer segment that is shaped like a rod.

Cone photoreceptors express a number of proteins that are not expressed by rod photoreceptors, including, e.g., L-opsin (OPN1LW, the nucleic acid and amino acid sequences for which may be found at GenBank Accession No: NM_020061.5), M-opsin (OPN1MW, the nucleic acid and amino acid sequences for which may be found at GenBank Accession No: NM_000513.2), or S-opsin (OPN1SW, the nucleic acid and amino acid sequences for which may be found at GenBank Accession No: NM_001708.2); whereas rod photoreceptors express a number of proteins that are not expressed by cone photoreceptors, e.g., rhodopsin (RHO, the nucleic acid and amino acid sequences for which may be found at GenBank Accession No: NM_000539.3) and rod-derived cone viability factor (RDCVF, also known as NXNL1, the nucleic acid and amino acid sequences for which may be found at GenBank Accession No: NM_138454.1). Functionally, cone photoreceptors differ from rod photoreceptors in that cone photoreceptors are responsible for color vision and function best in relatively bright light, whereas rod photoreceptors support vision at low light levels and function best in dim light; cones and rods can be distinguished based on this difference using an electroretinogram (ERG) or color ERG (cERG).

Cone photoreceptors may be distinguished from rod photoreceptors by their location in the retina. As discussed herein, the vast majority of cone photoreceptors—all of them L- and M-cone photoreceptors—are densely packed in a 1.5 mm depression located in the center of the macula of the retina, called the fovea centralis, with the remaining L- and M-cone photoreceptors and the S-cone photoreceptors scattered in the parafovea, the perifovea, and the peripheral retina. In contrast, rod photoreceptors are excluded from the foveola and are poorly represented in the fovea, instead being primarily found in the parafovea, the perifovea, and the peripheral retina.

rAAV Virions

In practicing the subject methods, a polynucleotide of interest is delivered to cone photoreceptors by injecting into the vitreous of the eye a recombinant viral particle comprising the polynucleotide of interest as a heterologous sequence within its genome. In some instances, the recombinant viral particles are recombinant adeno-associated virus (rAAV) particles.

In some embodiments, as noted above, the rAAV comprises an AAV serotype variant, i.e., a variant AAV capsid protein that comprises at least one amino acid difference relative to a corresponding parental AAV capsid protein, e.g., a wild type AAV capsid protein, and which does not consist of an amino acid sequence present in a naturally occurring AAV capsid protein. In some embodiments, the AAV vector comprises an AAV2 capsid variant that transduces foveal cone photoreceptors, for example, an AAV2.7m8 capsid variant, as provided in Table 1 below. In certain embodiments, the capsid variant is an AAV2.5T.LSV1 capsid as described in PCT/US2020/029895 and as provided in Table 1 below.

TABLE 1

Exemplary Sequences

| Name | Sequence | SEQ ID NO: |
|---|---|---|
| AAV2.7m8 VP1 Capsid Protein | MAADGYLPDWLEDTLSEGIRQWWKLKPGPPPPKPAERHKDDSRGLVLPGYK YLGPFNGLDKGEPVNEADAAALEHDKAYDRQLDSGDNPYLKYNHADAEFQE RLKEDTSFGGNLGRAVFQAKKRVLEPLGLVEEPVKTAPGKKRPVEHSPVEP DSSSGTGKAGGQPARKRLNFGQTGDADSVPDPQPLGQPPAAPSGLGTNTMA TGSGAPMADNNEGADGVGNSSGNWHCDSTWMGDRVITTSTRTWALPTYNNH LYKQISSQSGASNDNHYFGYSTPWGYFDFNRPHCHFSPRDWQRLINNNWGF RPKRLNFKLFNIQVKEVTQNDGTTTIANNLTSTVQVFTDSEYQLPYVLGSA HQGCLPPFPADVFMVPQYGYLTLNNGSQAVGRSSFYCLEYFPSQMLRTGNN FTFSYTFEDVPFHSSYAHSQSLDRLMNPLIDQYLYYLSRTNTPSGTTTQSR LQFSQAGASDIRDQSRNWLPGPCYRQQRVSKTSADNNNSEYSWTGATKYHL NGRDSLVNPGPAMASHKDDEEKFFPQSGVLIFGKQGSEKTNVDIEKVMITD EEEIRTTNPVATEQYGSVSTNLQRGNLALGETTRPARQAATADVNTQGVLP GMVWQDRDVYLQGPIWAKIPHTDGHFHPSPLMGGFGLKHPPPQILIKNTPV PANPSTTFSAAKFASFITQYSTGQVSVEIEWELQKENSKRWNPEIQYTSNY NKSVNVDFTVDTNGVYSEPRPIGTRYLTRNL | 1 |
| AAV2.5T.LSV1 VP1 Capsid Protein | MAADGYLPDWLEDTLSEGIRQWWKLKPGPPPPKPAERHKDDSRGLVLPGYK YLGPFNGLDKGEPVNEADAAALEHDKAYDRQLDSGDNPYLKYNHADAEFQE RLKEDTSFGGNLGRAVFQAKKRVLEPFGLVEEGAKTAPTGKRIDDHFPKRK KARTEEDSKPSTSSDAEAGPSGSQQLQIPAQPASSLGADTMSAGGGGPLGD NNQGADGVGNASGDWHCDSTWMGDRVVTKSTRTWVLPSYNNHQYREIKSGS VDGSNANAYFGYSTPWGYFDFNRFHSHWSPRDWQRLINNYWGFRPRSLRVK IFNIQVKEVTVQDSTTTIANNLTSTVQVFTDDDYQLPYVVGNGTEGCLPAF PPQVFTLPQYGYATLNRDNTENPTERSSFFCLEYFPSKMLRTGNNFEFTYN FEEVPFHSSFAPSQNLFKLANPLVDQYLYRFVSTNNTGGVQFNKNLAGRYA NTYKNWFPGPMGRTQGWNLGSGVNRASVSAFATTNRMELEGASYQVPPQPN GMTNNLQGSNTYALENTMIFNSQPANPGTTATYLEGNMLITSESETQPVNR VAYNVGGQMLAHKFKSGDAPTTGTYNLQEIVPGSVWMERDVYLQGPIWAKI PETGAHFHPSPAMGGFGLKHPPPMMLIKNTPVPGNITSFSDVPVSSFITQY STGQVTVEMEWELKKENSKRWNPEIQYTNNYNDPQFVDFAPDSTGEYRTTR PIGTRYLTRPL | 2 |

Thus, in certain embodiments, the AAV2 capsid variant is or is related to an AAV2.7m8 capsid or AAV2.5T.LSV1 capsid that comprises, consists, or consists essentially of an amino acid sequence that is at least 80, 85, 90, 95, 98, 99, or 100% identical to the sequence set forth in SEQ ID NO: 1 or 2, and which transduces foveal cone photoreceptors. rAAV variants encompassed by the subject compositions and that find use in the subject methods may be readily validated as such by determining the efficacy by which they transduce cone photoreceptors, e.g., foveal cone photoreceptors. For example, viral particles may be created comprising an AAV viral genome comprising an expression cassette comprising GFP operably linked to a cone promoter as known in the art, packaged into the subject rAAV, and the viral particles injected into the vitreous of a human eye. rAAV virions encompassed by the present disclosure will typically exhibit at least a 2-fold, at least a 5-fold, at least a 10-fold, at least a 15-fold, at least a 20-fold, at least a 25-fold, at least a 50-fold, in some instances, more than 50-fold, e.g., at least a 60-fold, at least a 70-fold, at least an 80-fold, at least a 90-fold, for example, a 100-fold increased infectivity of cone photoreceptors or more when administered via intravitreal injection relative to the infectivity of cone photoreceptors by an AAV virion comprising the corresponding parental AAV capsid protein, for example, the parental AAV2 capsid protein. Put another way, rAAV virions suitable for use in the subject methods will infect at least 10-fold more, at least 15-fold more, at least 20-fold more, at least 50-fold more, in some instances more than 50-fold more cone photoreceptors, e.g., at least 60-fold, at least 70-fold, at least 80-fold, at least 90-fold, for example, a 100-fold more cone photoreceptors than AAV virions comprising the corresponding parental AAV capsid protein, for example, the parental AAV2 capsid protein.

Certain embodiments comprise the step of detecting the presence of the delivered polynucleotide in a cone photoreceptor. Any convenient method may be employed for detecting the presence of the polynucleotide. For example, the polynucleotide may be detecting using, e.g., PCR, Next Gen sequencing, and the like, or the expression of a gene product encoded by the polynucleotide may be detected by, e.g., RT-PCR, Northern blot, RNAse protection, Western blot, ELISA, immunohistochemistry, and the like. These methods are particularly suited to preclinical studies. In clinical studies, in may be preferably to detect the presence of the polynucleotide by detecting the presence of a functional gene product, that is, by detecting the impact of the gene product on the viability or function of the cone photoreceptor in the subject. For example, if the gene product encoded by the polynucleotide improves the viability of the cone photoreceptor, an improvement in viability of the cone photoreceptor may be detected by, e.g., fundus photography, Optical coherence tomography (OCT), Adaptive Optics (AO), and the like, as a way of detecting the presence of the polynucleotide. If the gene product encoded by the polynucleotide alters the activity of the cone photoreceptor, the modified activity of the cone photoreceptor may be detected by, e.g., electroretinogram (ERG) and color ERG (cERG); color vision tests such as pseudoisochromatic plates (Ishihara plates, Hardy-Rand-Ritter polychromatic plates), the Farnsworth-Munsell 100 hue test, the Farnsworth's panel D-15, the City university test, Kollner's rule, and the like; and visual acuity tests such as the ETDRS letters test, Snellen visual acuity test, and the like, as a way of detecting the presence of the delivered polynucleotide.

In particular embodiments, as discussed herein, the AAV vector comprises a polynucleotide comprising a human L-opsin protein coding sequence operably linked to an M-opsin promoter sequence. OPN1LW is a gene on the X chromosome that encodes for long wave sensitive (LWS) opsin (or L-opsin). It is responsible for perception of visible light in the yellow-green range on the visible spectrum (around 500-570 nm). The gene contains 6 exons with variability that induces shifts in the spectral range (see, for example, NCBI Reference Sequence: NM_020061.6). The protein encoded is a G-protein coupled receptor with embedded 11-cis-retinal, whose light excitation causes a cis-trans conformational change that begins the process of chemical signaling to the brain.

In specific embodiments, the rAAV comprises the "MNTC expression cassette" flanked by 5' and 3' inverted terminal repeats (ITRs). The MNTC expression cassette includes a human LCR enhancer sequence, a truncated M-opsin promoter sequence, a 5' untranslated region (UTR) based on the M-opsin 5' UTR split into two by the insertion of a chimeric intron and a strong Kozak sequence to drive expression of the human L-opsin gene, an M-opsin 3' UTR, and an SV40 polyadenylation sequence. In specific embodiments, the polynucleotide in an AAV vector comprises, in a 5' to 3' orientation, a 5' AAV2 inverted terminal repeat (ITR), a human locus control region (LCR) enhancer sequence, a truncated M-opsin promoter sequence, a 5' untranslated region (UTR) composed of an M-opsin 5' UTR with an inserted chimeric intron and a strong Kozak sequence, the human L-opsin protein coding sequence, an M-opsin 3' UTR, an SV40 polyadenylation sequence, and a 3' AAV2 ITR. In particular embodiments, the polynucleotide in the AAV vector comprises the ADVM-062 vector genome sequence, as shown in Table 2.

TABLE 2

Exemplary Sequences

| Name | Sequence | SEQ ID NO: |
|---|---|---|
| ADVM-062 Vector Genome | GCGCGCTCGCTCGCTCACTGAGGCCGCCCGGGCAAAGCCCGGGCGTCGGGCGAC CTTTGGTCGCCCGGCCTCAGTGAGCGAGCGAGCGCGCAGAGAGGGAGTGGCCAA CTCCATCACTAGGGGTTCCTTGTAGTTAATGATTAACCCGCCATGCTACTTATC TACGTAGCCATGCTCTAGGATCTTCAATATTGGCCATTAGCCATATTATTCATT GGTTATATAGCATAAATCAATATTGGCTATTGGCCATTGCATACGTTGTATCTA TATCATAATATGTACATTTATATTGGCTCATGTCCAATATGACCGCCATGTTGG CATTGATTATTGACTAGTCCTACAGCAGCCAGGGTGAGATTATGAGGCTGAGCT GAGAATATCAAGACTGTACCGAGTAGGGGGCCTTGGCAAGTGTGGAGAGCCCGG CAGCTGGGGCAGAGGGCGGAGTACGGTGTGCGTTTACGGACCTCTTCAAACGAG GTAGGAAGGTCAGAAGTCAAAAAGGGAACAAATGATGTTTAACCACACAAAAAT GAAAATCCAATGGTTGGATATCCATTCCAAATACACAAAGGCAACGGATAAGTG ATCCGGGCCAGGCACAGAAGGCCATGCACCCGTAGGATTGCACTCAGAGCTCCC AAATGCATAGGAATAGAAGGGTGGGTGCAGGAGGCTGAGGGGTGGGAAAGGGC ATGGGTGTTTCATGAGGACAGAGCTTCCGTTTCATGCAATGAAAAGAGTTTGGA GACGGATGGTGGTGACTGGACTATACACTTACACACGGTAGCGATGGTACACTT | 3 |

TABLE 2-continued

Exemplary Sequences

| Name | Sequence | SEQ ID NO: |
|---|---|---|
| | TGTATTATGTATATTTTACCACGATCTTTTTAAAGTGTCAAAGGCAAATGGCCA<br>AATGGTTCCTTGTCCTATAGCTGTAGCAGCCATCGGCTGTTAGTGACAAAGCCC<br>CTGAGTCAAGATGACAGCAGCCCCCATAACTCCTAATCGGCTCTCCCGCGTGGA<br>GTCATTTAGGAGTAGTCGCATTAGAGACAAGTCCAACATCTAATCTTCCACCCT<br>GGCCAGGGCCCCAGCTGGCAGCGAGGGTGGGAGACTCCGGGCAGAGCAGAGGGC<br>GCTGACATTGGGGCCCGGCCTGGCTTGGGTCCCTCTGGCCTTTCCCCAGGGGCC<br>CTCTTTCCTTGGGGCTTTCTTGGGCCGCCACTGCTCCCGCTCCTCTCCCCCCAT<br>CCCACCCCCTCACCCCCTCGTTCTTCATATCCTTCTCTAGTGCTCCCTCCACTT<br>TCATCCACCCTTCTGCAAGAGTGTGGGACCACAAATGAGTTTTCACCTGGCCTG<br>GGGACACACGTGCCCCCACAGGTGCTGAGTGACTTTCTAGGACAGTAATCTGCT<br>TTAGGCTAAAATGGGACTTGATCTTCTGTTAGCCCTAATCATCAATTAGCAGAG<br>CCGGTGAAGGTGCAGAACCTACCGCCTTTCCAGGCCTCCTCCCACCCTCTGCCAC<br>CTCCACTCTCCTTCCTGGGATGTGGGGGCTGGCACACGTGTGGCCCAGGGCATT<br>GGTGGGATTGCACTGAGCTGGGTCATTAGCGTAATCCTGGACAAGGGCAGACAG<br>GGCGAGCGGAGGGCCAGCTCCGGGGCTCAGGCAAGGCTGGGGGCTTCCCCCAGA<br>CACCCCACTCCTCCTCTGCTGGACCCCCACTTCATAGGGCACTTCGTGTTCTCA<br>AAGGGCTTCCAAATAGCATGGTGGCCTTGGATGCCCAGGGAAGCCTCAGAGTTG<br>CTTATCTCCCTCTAGACAGAAGGGGAATCTCGGTCAAGAGGGAGAGGTCGCCCT<br>GTTCAAGGCCACCCAGCCAGCTCATGGCGGTAATGGGACAAGGCTGGCCAGCCA<br>TCCCACCCTCAGAAGGGACCCGGTGGGGCAGGTGATCTCAGAGGAGGCTCACTT<br>CTGGGTCTCACATTCTTCCAGCAAATCCCTCTGAGCCGCCCCGGGGGCTCGCC<br>TCAGGAGCAAGGAAGCAAGGGGTGGGAGGAGGAGGTCTAAGTCCCAGGCCCAAT<br>TAAGAGATCAGATGGTGTAGGATTTGGGAGCTTTTAAGGTGAAGAGGCCCGGGC<br>TGATCCCACTGGCCGGTATAAAGCACCGTGACCCTCAGGTGACGCACCAGGGCC<br>GGCTGCCGTCGGGGACAGGGCTTTCCATAGCCCAGGTAAGTATCAAGGTTACAA<br>GACAGGTTTAAGGAGACCAATAGAAACTGGGCTTGTCGAGACAGAGAAGACTCT<br>TGCGTTTCTGATAGGCACCTATTGGTCTTACTGACATCCACTTTGCCTTTCTCT<br>CCACAGGCCCAGAGAGGAGACAGGCCGCCACCATGGCCCAGCAGTGGAGCCTCC<br>AAAGGCTCGCAGGCCGCCATCCGCAGGACAGCTATGAGGACAGCACCCAGTCCA<br>GCATCTTCACCTACACCAACAGCAACTCCACCAGAGGCCCCTTCGAAGGCCCGA<br>ATTACCACATCGCTCCCAGATGGGTGTACCACCTCACCAGTGTCTGGATGATCT<br>TTGTGGTCACTGCATCCGTCTTCACAAATGGGCTTGTGCTGGCGGCCACCATGA<br>AGTTCAAGAAGCTGCGCCACCCGCTGAACTGGATCCTGGTGAACCTGGCGGTCG<br>CTGACCTAGCAGAGACCGTCATCGCCAGCACTATCAGCATTGTGAACCAGGTCT<br>CTGGCTACTTCGTGCTGGGCCACCCTATGTGTGTCCTGGAGGGCTACACCGTCT<br>CCCTGTGTGGGATCACAGGTCTCTGGTCTCTGGCCATCATTTCCTGGGAGAGGT<br>GGCTGGTGGTGTGCAAGCCCTTTGGCAATGTGAGATTTGATGCCAAGCTGGCCA<br>TCGTGGGCATTGCCTTCTCCTGGATCTGGTCTGCTGTGTGGACAGCCCCGCCCA<br>TCTTTGGTTGGAGCAGGTACTGGCCCCACGGCCTGAAGACTTCATGCGGCCCAG<br>ACGTGTTCAGCGGCAGCTCGTACCCCGGGGTGCAGTCTTACATGATTGTCCTCA<br>TGGTCACCTGCTGCATCATCCCACTCGCTATCATCATGCTCTGCTACCTCCAAG<br>TGTGGCTGGCCATCCGAGCGGTGGCAAAGCAGCAGAAAGAGTCTGAATCCACCC<br>AGAAGGCAGAGAAGGAAGTGACGCGCATGGTGGTGGTGATGATCTTTGCGTACT<br>GCGTCTGCTGGGGACCCTACACCTTCTTCGCATGCTTTGCTGCTGCCAACCCTG<br>GTTACGCCTTCCACCCTTTGATGGCTGCCCTGCCGGCCTACTTTGCCAAAAGTG<br>CCACTATCTACAACCCCGTTATCTATGTCTTTATGAACCGGCAGTTTCGAAACT<br>GCATCTTGCAGCTTTTCGGGAAGAAGGTTGACGATGGCTCTGAACTCTCCAGCG<br>CCTCCAAAACGGAGGTCTCATCTGTGTCCTCGGTATCGCCTGCATGAGGTCTGC<br>CTCCTACCCATCCCGCCCACCGGGGCTTTGGCCACCTCTCCTTTCCCCCTCCTT<br>CTCCATCCCTGTAAAATAAATGTAATTTATCTTTGCCAAAACCAACAGACATGA<br>TAAGATACATTGATGAGTTTGGACAAACCACAACTAGAATGCAGTGAAAAAAAT<br>GCTTTATTTGTGAAATTTGTGATGCTATTGCTTTATTTGTAACCATTATAAGCT<br>GCAATAAACAAGTTAACAACAACAATTGCATTCATTTTATGTTTCAGGTTCAGG<br>GGGAGATGTGGGAGGTTTTTTAAAGCAAGTAAAACCTCTACAAATGTGGTAAAA<br>TCGATAAGGATCCTAGAGCATGGCTACGTAGATAAGTAGCATGGCGGGTTAATC<br>ATTAACTACAAGGAACCCCTAGTGATGGAGTTGGCCACTCCCTCTCTGCGCGCT<br>CGCTCGCTCACTGAGGCCGGGCGACCAAAGGTCGCCCGACGCCCGGGCTTTGCC<br>CGGGCGGCCTCAGTGAGCGAGCGAGCGCGC | |

Thus, in certain embodiments, the polynucleotide comprises, consists, or consists essentially of a sequence that is at least 80, 85, 90, 95, 98, 99, or 100% identical to the sequence set forth in SEQ ID NO: 3, and encodes and expresses a biologically-active human L-opsin protein. In specific embodiments, the MNTC-L Opsin cassette, flanked by AAV2 inverted ITRs, is packaged in the AAV2.7m8 capsid variant.

rAAV virions comprising the polynucleotide of interest of the present disclosure may be produced using any convenient methodologies, AAV packaging cells, and packaging technology as known to those of skill in the art. For example, an AAV expression vector (that is, a plasmid comprising the rAAV genome as well as elements useful for the cloning of the genomic elements in, e.g., bacteria, e.g., origin of replication, selectable marker, etc.) may be transfected into mammalian producer cells. Also transfected into the mammalian producer cells is an AAV helper construct, i.e., a plasmid comprising AAV REP and CAP coding regions that can be expressed in the producer cell, which complement AAV helper functions absent from the AAV expression vector. The dually-transfected producer cells are then infected by a helper virus, e.g., adenovirus, or transfected with a plasmid comprising helper virus accessory genes that promote AAV vector replication, e.g., regions VA, E2A, E4, so as to promote efficient rAAV virus production. The producer cells are then cultured to produce rAAV, and AAV vectors are purified and formulated using standard techniques known in the art.

As another example, an AAV expression vector may be packaged as a baculovirus and introduced into insect producer cells, e.g., Sf9 cells. Also introduced into the insect cells by another baculovirus are the AAV REP and CAP genes. Baculovirus-being a virus—comprises the genes encoding the accessory functions necessary for efficient rAAV virus production. Accordingly, upon infection of the insect cells by the two baculoviruses, the producer cells can be cultured to produce rAAV, and AAV vectors purified and formulated using standard techniques known in the art.

Examples of these and other methods may be found in, for example, U.S. Pat. Nos. 5,436,146; 5,753,500, 6,040,183, 6,093,570 and 6,548,286, expressly incorporated by reference herein in their entirety. Further compositions and methods for packaging are described in Wang et al. (U.S. Application No. 2002/0168342), also incorporated by reference herein in its entirety.

Any convenient host cells used in the art for producing rAAV virions may be employed in the production of the subject vectors, including, for example, mammalian cells, insect cells, microorganisms and yeast, e.g., SF-9, 293, A549, HeLa cells, etc. In some instances, the host cells are packaging cells in which the AAV rep and cap genes are stably maintained in the host cell. In some instances, the host cells are producer cells in which the AAV vector genome is stably maintained and packaged.

Methods of Administration and Treatment

As noted herein, embodiments of the present disclosure relate to methods of treating a color vision deficiency in a human subject in need thereof, comprising intravitreally administering to the subject a recombinant AAV (rAAV) vector at a dosage ranging from about $1\times10^{10}$ to about $1\times10^{12}$ vector genomes (vg)/eye. That is, the dosage forms and pharmaceutical composition described herein are administered to the eye of the subject by intravitreal injection. General methods for delivering a vector via intravitreal injection may be illustrated by the following brief outlines. These examples are merely meant to illustrate certain features of the methods, and are in no way meant to be limiting.

For intravitreal administration, the vector can be delivered in the form of a suspension. Initially, topical anesthetic is applied to the surface of the eye followed by a topical antiseptic solution. The eye is held open, with or without instrumentation, and the vector is injected through the sclera with a short, narrow, for example a 30 gauge needle, into the vitreous cavity of the eye of a subject under direct observation. Typically, a volume of 1 to 100 µL, e.g., 25 µL, 50 µL, or 100 µL, and usually no more than 100 µL, of the subject composition may be delivered to the eye by intravitreal injection without removing the vitreous. Alternatively, a vitrectomy may be performed, and the entire volume of vitreous gel is replaced by an infusion of the subject composition. In such cases, up to about 4 mL of the subject composition may be delivered, e.g., to a human eye. Intravitreal administration is generally well tolerated. At the conclusion of the procedure, there is sometimes mild redness at the injection site. There is occasional tenderness, but most patients do not report any pain. No eye patch or eye shield is necessary after this procedure, and activities are not restricted. Sometimes, an antibiotic eye drop is prescribed for several days to help prevent infection.

Certain embodiments comprise intravitreally administering the rAAV vector at a dosage of about $1\times10^{10}$, about $2\times10^{10}$, about $3\times10^{10}$, about $4\times10^{10}$, about $5\times10^{10}$, about $6\times10^{10}$, about $7\times10^{10}$, about $8\times10^{10}$, about $9\times10^{10}$, about $1\times10^{11}$, about $2\times10^{11}$, about $3\times10^{11}$, about $4\times10^{11}$, about $5\times10^{11}$, about $6\times10^{11}$, about $7\times10^{11}$, about $8\times10^{11}$, about $9\times10^{11}$, or about $1\times10^{12}$ vg/eye, for example, intravitreally administering the rAAV vector at a dosage ranging from about $1\times10^{10}$ to about $2\times10^{10}$ vg/eye, about $1\times10^{10}$ to about $3\times10^{10}$ vg/eye, about $1\times10^{10}$ to about $4\times10^{10}$ vg/eye, about $1\times10^{10}$ to about $5\times10^{10}$ vg/eye, about $1\times10^{10}$ to about $6\times10^{10}$ vg/eye, about $1\times10^{10}$ to about $7\times10^{10}$ vg/eye, about $1\times10^{10}$ to about $8\times10^{10}$ vg/eye, about $1\times10^{10}$ to about $9\times10^{10}$ vg/eye, about $1\times10^{10}$ to about $1\times10^{11}$ vg/eye, about $1\times10^{10}$ to about $2\times10^{11}$ vg/eye, about $1\times10^{10}$ to about $3\times10^{11}$ vg/eye, about $1\times10^{10}$ to about $4\times10^{11}$ vg/eye, about $1\times10^{10}$ to about $5\times10^{11}$ vg/eye, about $1\times10^{10}$ to about $6\times10^{11}$ vg/eye, about $1\times10^{10}$ to about $7\times10^{11}$ vg/eye, about $1\times10^{10}$ to about $8\times10^{11}$ vg/eye, about $1\times10^{10}$ to about $9\times10^{11}$ vg/eye, about $1\times10^{10}$ to about $1\times10^{12}$ vg/eye, about $2\times10^{10}$ to about $3\times10^{10}$ vg/eye, about $2\times10^{10}$ to about $4\times10^{10}$ vg/eye, about $2\times10^{10}$ to about $5\times10^{10}$ vg/eye, about $2\times10^{10}$ to about $6\times10^{10}$ vg/eye, about $2\times10^{10}$ to about $7\times10^{10}$ vg/eye, about $2\times10^{10}$ to about $8\times10^{10}$ vg/eye, about $2\times10^{10}$ to about $9\times10^{10}$ vg/eye, about $2\times10^{10}$ to about $1\times10^{11}$ vg/eye, about $2\times10^{10}$ to about $2\times10^{11}$ vg/eye, about $2\times10^{10}$ to about $3\times10^{11}$ vg/eye, about $2\times10^{10}$ to about $4\times10^{11}$ vg/eye, about $2\times10^{10}$ to about $5\times10^{11}$ vg/eye, about $2\times10^{10}$ to about $6\times10^{11}$ vg/eye, about $2\times10^{10}$ to about $7\times10^{11}$ vg/eye, about $2\times10^{10}$ to about $8\times10^{11}$ vg/eye, about $2\times10^{10}$ to about $9\times10^{11}$ vg/eye, about $2\times10^{10}$ to about $1\times10^{12}$ vg/eye, about $3\times10^{10}$ to about $4\times10^{10}$ vg/eye, about $3\times10^{10}$ to about $5\times10^{10}$ vg/eye, about $3\times10^{10}$ to about $6\times10^{10}$ vg/eye, about $3\times10^{10}$ to about $7\times10^{10}$ vg/eye, about $3\times10^{10}$ to about $8\times10^{10}$ vg/eye, about $3\times10^{10}$ to about $9\times10^{10}$ vg/eye, about $3\times10^{10}$ to about $1\times10^{11}$ vg/eye, about $3\times10^{10}$ to about $2\times10^{11}$ vg/eye, about $3\times10^{10}$ to about $3\times10^{11}$ vg/eye, about $3\times10^{10}$ to about $4\times10^{11}$ vg/eye, about $3\times10^{10}$ to about $5\times10^{11}$ vg/eye, about $3\times10^{10}$ to about $6\times10^{11}$ vg/eye, about $3\times10^{10}$ to about $7\times10^{11}$ vg/eye, about $3\times10^{10}$ to about $8\times10^{11}$ vg/eye, about $3\times10^{10}$ to about $9\times10^{11}$ vg/eye, about $3\times10^{10}$ to about $1\times10^{12}$ vg/eye, about $4\times10^{10}$ to about $5\times10^{10}$ vg/eye, about $4\times10^{10}$ to about $6\times10^{10}$ vg/eye, about $4\times10^{10}$ to about $7\times10^{10}$ vg/eye, about $4\times10^{10}$ to about $8\times10^{10}$ vg/eye, about $4\times10^{10}$ to about $9\times10^{10}$ vg/eye, about $4\times10^{10}$ to about $1\times10^{11}$ vg/eye, about $4\times10^{10}$ to about $2\times10^{11}$ vg/eye, about $4\times10^{10}$ to about $3\times10^{11}$ vg/eye, about $4\times10^{10}$ to about $4\times10^{11}$ vg/eye, about $4\times10^{10}$ to about $5\times10^{11}$ vg/eye, about $4\times10^{10}$ to about $6\times10^{11}$ vg/eye, about $4\times10^{10}$ to about $7\times10^{11}$ vg/eye, about $4\times10^{10}$ to about $8\times10^{11}$ vg/eye, about $4\times10^{10}$ to about $9\times10^{11}$ vg/eye, about $4\times10^{10}$ to about $1\times10^{12}$ vg/eye, about $5\times10^{10}$ to about $6\times10^{10}$ vg/eye, about $5\times10^{10}$ to about $7\times10^{10}$ vg/eye, about $5\times10^{10}$ to about $8\times10^{10}$ vg/eye, about $5\times10^{10}$ to about $9\times10^{10}$ vg/eye, about $5\times10^{10}$ to about $1\times10^{11}$ vg/eye, about $5\times10^{10}$ to about $2\times10^{11}$ vg/eye, about $5\times10^{10}$ to about $3\times10^{11}$ vg/eye, about $5\times10^{10}$ to about $4\times10^{11}$ vg/eye, about $5\times10^{10}$ to about $5\times10^{11}$ vg/eye, about $5\times10^{10}$ to about $6\times10^{11}$ vg/eye, about $5\times10^{10}$ to about $7\times10^{11}$ vg/eye, about $5\times10^{10}$ to about $8\times10^{11}$ vg/eye, about $5\times10^{10}$ to about $9\times10^{11}$ vg/eye, about $5\times10^{10}$ to about $1\times10^{12}$ vg/eye, about $6\times10^{10}$ to about $7\times10^{10}$ vg/eye, about $6\times10^{10}$ to about $8\times10^{10}$ vg/eye, about $6\times10^{10}$ to about $9\times10^{10}$ vg/eye, about $6\times10^{10}$ to about $1\times10^{11}$ vg/eye, about $6\times10^{10}$ to about $2\times10^{11}$ vg/eye, about $6\times10^{10}$ to about $3\times10^{11}$ vg/eye, about $6\times10^{10}$ to about $4\times10^{11}$ vg/eye, about $6\times10^{10}$ to about $5\times10^{11}$ vg/eye, about $6\times10^{10}$ to about $6 \times 10^{11}$ vg/eye, about $6 \times 10^{10}$ to about $7 \times 10^{11}$ vg/eye, about $6 \times 10^{10}$ to about $8 \times 10^{11}$ vg/eye, about $6 \times 10^{10}$ to about $9 \times 10^{11}$ vg/eye, about $6 \times 10^{10}$ to about $1 \times 10^{12}$ vg/eye, about $7 \times 10^{10}$ to about $8 \times 10^{10}$ vg/eye, about $7 \times 10^{10}$ to about $9 \times 10^{10}$ vg/eye, about $7 \times 10^{10}$ to about $1 \times 10^{11}$ vg/eye, about $7 \times 10^{10}$ to about $2 \times 10^{11}$ vg/eye, about $7 \times 10^{10}$ to about $3 \times 10^{11}$ vg/eye, about $7 \times 10^{10}$ to about $4 \times 10^{11}$ vg/eye, about $7 \times 10^{10}$ to about $5 \times 10^{11}$ vg/eye, about $7 \times 10^{10}$ to about $6 \times 10^{11}$ vg/eye, about $7 \times 10^{10}$ to about $7 \times 10^{11}$ vg/eye, about $7 \times 10^{10}$ to about $8 \times 10^{11}$ vg/eye, about $7 \times 10^{10}$ to about $9 \times 10^{11}$ vg/eye, about $7 \times 10^{10}$ to about $1 \times 10^{12}$ vg/eye, about $8 \times 10^{10}$ to about $9 \times 10^{10}$ vg/eye, about $8 \times 10^{10}$ to about $1 \times 10^{11}$ vg/eye, about $8 \times 10^{10}$ to about $2 \times 10^{11}$ vg/eye, about $8 \times 10^{10}$ to about $3 \times 10^{11}$ vg/eye, about $8 \times 10^{10}$ to about $4 \times 10^{11}$ vg/eye, about $8 \times 10^{10}$ to about $5 \times 10^{11}$ vg/eye, about $8 \times 10^{10}$ to about $6 \times 10^{11}$ vg/eye, about $8 \times 10^{10}$ to about $7 \times 10^{11}$ vg/eye, about $8 \times 10^{10}$ to about $8 \times 10^{11}$ vg/eye, about $8 \times 10^{10}$ to about $9 \times 10^{11}$ vg/eye, about $8 \times 10^{10}$ to about $1 \times 10^{12}$ vg/eye, about $9 \times 10^{10}$ to about $1 \times 10^{11}$ vg/eye, about $9 \times 10^{10}$ to about $2 \times 10^{11}$ vg/eye, about $9 \times 10^{10}$ to about $3 \times 10^{11}$ vg/eye, about $9 \times 10^{10}$ to about $4 \times 10^{11}$ vg/eye, about $9 \times 10^{10}$ to about $5 \times 10^{11}$ vg/eye, about $9 \times 10^{10}$ to about $6 \times 10^{11}$ vg/eye, about $9 \times 10^{10}$ to about $7 \times 10^{11}$ vg/eye, about $9 \times 10^{10}$ to about $8 \times 10^{11}$ vg/eye, about $9 \times 10^{10}$ to about $9 \times 10^{11}$ vg/eye, about $9 \times 10^{10}$ to about $1 \times 10^{12}$ vg/eye, about $1 \times 10^{11}$ to about $2 \times 10^{11}$ vg/eye, about $1 \times 10^{11}$ to about $3 \times 10^{11}$ vg/eye, about $1 \times 10^{11}$ to about $4 \times 10^{11}$ vg/eye, about $1 \times 10^{11}$ to about $5 \times 10^{11}$ vg/eye, about $1 \times 10^{11}$ to about $6 \times 10^{11}$ vg/eye, about $1 \times 10^{11}$ to about $7 \times 10^{11}$ vg/eye, about $1 \times 10^{11}$ to about $8 \times 10^{11}$ vg/eye, about $1 \times 10^{11}$ to about $9 \times 10^{11}$ vg/eye, about $1 \times 10^{11}$ to about $1 \times 10^{12}$ vg/eye, about $2 \times 10^{11}$ to about $3 \times 10^{11}$ vg/eye, about $2 \times 10^{11}$ to about $4 \times 10^{11}$ vg/eye, about $2 \times 10^{11}$ to about $5 \times 10^{11}$ vg/eye, about $2 \times 10^{11}$ to about $6 \times 10^{11}$ vg/eye, about $2 \times 10^{11}$ to about $7 \times 10^{11}$ vg/eye, about $2 \times 10^{11}$ to about $8 \times 10^{11}$ vg/eye, about $2 \times 10^{11}$ to about $9 \times 10^{11}$ vg/eye, about $2 \times 10^{11}$ to about $1 \times 10^{12}$ vg/eye, about $3 \times 10^{11}$ to about $4 \times 10^{11}$ vg/eye, about $3 \times 10^{11}$ to about $5 \times 10^{11}$ vg/eye, about $3 \times 10^{11}$ to about $6 \times 10^{11}$ vg/eye, about $3 \times 10^{11}$ to about $7 \times 10^{11}$ vg/eye, about $3 \times 10^{11}$ to about $8 \times 10^{11}$ vg/eye, about $3 \times 10^{11}$ to about $9 \times 10^{11}$ vg/eye, about $3 \times 10^{11}$ to about $1 \times 10^{11}$ vg/eye, about $4 \times 10^{11}$ to about $5 \times 10^{11}$ vg/eye, about $4 \times 10^{11}$ to about $6 \times 10^{11}$ vg/eye, about $4 \times 10^{11}$ to about $7 \times 10^{11}$ vg/eye, about $4 \times 10^{11}$ to about $8 \times 10^{11}$ vg/eye, about $4 \times 10^{11}$ to about $9 \times 10^{11}$ vg/eye, about $4 \times 10^{11}$ to about $1 \times 10^{11}$ vg/eye, about $5 \times 10^{11}$ to about $6 \times 10^{11}$ vg/eye, about $5 \times 10^{11}$ to about $7 \times 10^{11}$ vg/eye, about $5 \times 10^{11}$ to about $8 \times 10^{11}$ vg/eye, about $5 \times 10^{11}$ to about $9 \times 10^{11}$ vg/eye, about $5 \times 10^{11}$ to about $1 \times 10^{11}$ vg/eye, about $6 \times 10^{11}$ to about $7 \times 10^{11}$ vg/eye, about $6 \times 10^{11}$ to about $8 \times 10^{11}$ vg/eye, about $6 \times 10^{11}$ to about $9 \times 10^{11}$ vg/eye, about $6 \times 10^{11}$ to about $1 \times 10^{11}$ vg/eye, about $7 \times 10^{11}$ to about $8 \times 10^{11}$ vg/eye, about $7 \times 10^{11}$ to about $9 \times 10^{11}$ vg/eye, about $7 \times 10^{11}$ to about $1 \times 10^{11}$ vg/eye, about $8 \times 10^{11}$ to about $9 \times 10^{11}$ vg/eye, about $8 \times 10^{11}$ to about $1 \times 10^{11}$ vg/eye, or about $9 \times 10^{11}$ to about $1 \times 10^{11}$ vg/eye.

Specific embodiments include intravitreally administering the rAAV vector at a dosage ranging from about $6 \times 10^{10}$ to about $6 \times 10^{11}$ vg/eye, for example, intravitreally administering the rAAV vector at a dosage of about $6 \times 10^{10}$, about $7 \times 10^{10}$, about $8 \times 10^{10}$, about $9 \times 10^{10}$, about $1 \times 10^{11}$ vg/eye, about $2 \times 10^{11}$ vg/eye, about $3 \times 10^{11}$ vg/eye, about $4 \times 10^{11}$ vg/eye, about $5 \times 10^{11}$ vg/eye, or about $6 \times 10^{11}$ vg/eye. Non-limiting examples include intravitreally administering the rAAV vector at a dosage ranging from about $6 \times 10^{10}$ to about $7 \times 10^{10}$ vg/eye, about $6 \times 10^{10}$ to about $8 \times 10^{10}$ vg/eye, about $6 \times 10^{10}$ to about $9 \times 10^{10}$ vg/eye, about $6 \times 10^{10}$ to about $1 \times 10^{11}$ vg/eye, about $6 \times 10^{10}$ to about $2 \times 10^{11}$ vg/eye, about $6 \times 10^{10}$ to about $3 \times 10^{11}$ vg/eye, about $6 \times 10^{10}$ to about $4 \times 10^{11}$ vg/eye, about $6 \times 10^{10}$ to about $5 \times 10^{11}$ vg/eye, about $6 \times 10^{10}$ to about $6 \times 10^{11}$ vg/eye, about $7 \times 10^{10}$ to about $8 \times 10^{10}$ vg/eye, about $7 \times 10^{10}$ to about $9 \times 10^{10}$ vg/eye, about $7 \times 10^{10}$ to about $1 \times 10^{11}$ vg/eye, about $7 \times 10^{10}$ to about $2 \times 10^{11}$ vg/eye, about $7 \times 10^{10}$ to about $3 \times 10^{11}$ vg/eye, about $7 \times 10^{10}$ to about $4 \times 10^{11}$ vg/eye, about $7 \times 10^{10}$ to about $5 \times 10^{11}$ vg/eye, about $7 \times 10^{10}$ to about $6 \times 10^{11}$ vg/eye, about $8 \times 10^{10}$ to about $9 \times 10^{10}$ vg/eye, about $8 \times 10^{10}$ to about $1 \times 10^{11}$ vg/eye, about $8 \times 10^{10}$ to about $2 \times 10^{11}$ vg/eye, about $8 \times 10^{10}$ to about $3 \times 10^{11}$ vg/eye, about $8 \times 10^{10}$ to about $4 \times 10^{11}$ vg/eye, about $8 \times 10^{10}$ to about $5 \times 10^{11}$ vg/eye, about $8 \times 10^{10}$ to about $6 \times 10^{11}$ vg/eye, about $9 \times 10^{10}$ to about $1 \times 10^{11}$ vg/eye, about $9 \times 10^{10}$ to about $2 \times 10^{11}$ vg/eye, about $9 \times 10^{10}$ to about $3 \times 10^{11}$ vg/eye, about $9 \times 10^{10}$ to about $4 \times 10^{11}$ vg/eye, about $9 \times 10^{10}$ to about $5 \times 10^{11}$ vg/eye, about $9 \times 10^{10}$ to about $6 \times 10^{11}$ vg/eye, about $1 \times 10^{11}$ to about $2 \times 10^{11}$ vg/eye, about $1 \times 10^{11}$ to about $3 \times 10^{11}$ vg/eye, about $1 \times 10^{11}$ to about $4 \times 10^{11}$ vg/eye, about $1 \times 10^{11}$ to about $5 \times 10^{11}$ vg/eye, about $1 \times 10^{11}$ to about $6 \times 10^{11}$ vg/eye, about $2 \times 10^{11}$ to about $3 \times 10^{11}$ vg/eye, about $2 \times 10^{11}$ to about $4 \times 10^{11}$ vg/eye, about $2 \times 10^{11}$ to about $5 \times 10^{11}$ vg/eye, about $2 \times 10^{11}$ to about $6 \times 10^{11}$ vg/eye, about $3 \times 10^{11}$ to about $4 \times 10^{11}$ vg/eye, about $3 \times 10^{11}$ to about $5 \times 10^{11}$ vg/eye, about $3 \times 10^{11}$ to about $6 \times 10^{11}$ vg/eye, about $4 \times 10^{11}$ to about $5 \times 10^{11}$ vg/eye, about $4 \times 10^{11}$ to about $6 \times 10^{11}$ vg/eye, or about $5 \times 10^{11}$ to about $6 \times 10^{11}$ vg/eye.

The subject methods and/or compositions may be used in medicine to express a therapeutic polynucleotide in cone photoreceptors as a therapy to treat or prevent a color vision deficiency, for example, in a human subject in need thereof. A "color vision deficiency" refers to the decreased ability to see color or differences in color, and is most commonly an inherited problem in the development of one or more of the three sets of the eyes' cone cells, which sense color. However, color vision deficiencies can also result from physical or chemical damage to the eye, the optic nerve, or parts of the brain. Diagnosis is typically with the Ishihara color test and/or genetic testing.

The terms "treatment", "treating" and the like are used herein to generally mean obtaining a desired pharmacologic and/or physiologic effect. The effect may be prophylactic in terms of completely or partially preventing a disease or symptom thereof, e.g., reducing the likelihood that the disease or symptom thereof occurs in the subject, and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

Examples of color vision deficiencies include Blue Cone Monochromacy (BCM) and Red-Green Color Blindness. BCM is a rare X-linked congenital stationary cone dysfunction syndrome, affecting approximately 1 in 100,000 individuals. Affected males with BCM have no functional long wavelength sensitive (L) or medium wavelength sensitive (M) cones in the retina, due to mutations at the genetic locus for the L and M-opsin genes. Color discrimination is severely impaired from birth, and vision is derived from the remaining preserved S cones and rod photoreceptors. BCM typically presents with reduced visual acuity (6/24 to 6/60), pendular nystagmus, photophobia, and patients often have myopia. The rod-specific and maximal electroretinogram (ERG) usually show no definite abnormality, whereas the 30 Hz cone ERG cannot be detected. Single flash photopic ERG is often recordable, albeit small and late, and the S cone ERG is well preserved.

BCM is characterized by severely impaired color discrimination, poor visual acuity, nystagmus, and photophobia. The genetic mechanisms underlying BCM involve mutations that result either in large deletions in the locus control region (LCR) or nonhomologous recombination between the L- and M-opsin genes followed by a missense point mutation inactivating the residual gene, with a C203R mutation being described most frequently. Other BCM cases involves inactivating mutations within the LCR itself that inhibit expression of both the L- and M-opsin genes. In most all cases, these mutations result in a lack of functional L- and M-opsins, and thus inactive L- and M-cones. L- and M-cones are the principal photoreceptors of the fovea centralis and have primary roles in high acuity foveal vision. Therefore, the loss of L- and M-cone function in BCM patients severely affects foveal vision. In the absence of functional L- and M-opsin cones, BCM patients must rely on sparsely distributed S-cones for vision under photopic luminance levels, when rod photoreceptors are typically inactive. This results in decreased visual acuity (ranging from 20/63 to 20/200) and significant deficiencies in color discrimination.

Red-Green Color Blindness is the most common form of color vision deficiency that makes it difficult to distinguish between red and green. There are at least four types of Red-Green Color Blindness, including protanopia (red-blindness, unable to distinguish between red and green), protanomaly (red-weakness, red looks more green and less bright), deuteranopia (green-blindness, unable to distinguish between red and green), and deuteranomaly (green-weakness, green looks more red). Thus, in certain embodiments, a subject has at least one of the foregoing types of Red-Green Color Blindness.

In certain embodiments, the subject prior to treatment has impaired color discrimination, decreased visual acuity, nystagmus, and/or photophobia. In specific embodiments, the subject prior to treatment has decreased functional L-opsins and M-opsins, inactive L-cones and M-cones, and decreased foveal vision. In particular embodiments, for example, in treating BCM, the subject is characterized by one or more genetic mutations selected from deletions in the locus control region (LCR), nonhomologous recombination between the L- and M-opsin genes and at least one missense point mutation inactivating the residual gene (e.g., a C203R mutation), and/or one or more inactivating mutations within the LCR that inhibit expression of the L-opsin and M-opsin genes. In certain embodiments, the subject is a male, for example, about 5, 10, 15, 20, 25, 30, 35, 40, 50, 55, or 60 years of age. In certain embodiments, the subject is a pediatric subject (e.g., about or up to about 5, 10, 15, 20 years of age), and the dosage is about $2 \times 10^{10}$ vg/eye or $3 \times 10^{10}$ vg/eye.

In practicing the subject methods, the subject composition is typically delivered to the retina of the subject in an amount that is effective to result in the expression of the transgene in the cone cells. For instance, in certain embodiments, intravitreally administering the rAAV vector transduces about or at least about 10% to 85% or more (e.g., 10, 15, 20, 25, 30, 35, 40, 45, 50, 55, 60, 65, 70, 75, 80, or 85% or more) of the subject's cone photoreceptors (e.g., foveal cones) with the polynucleotide encoding and expressing the polynucleotide of interest, such as the polynucleotide encoding the human L-opsin protein. In some embodiments, the method comprises the step of detecting the expression of the transgene in the cone cells.

In practicing the subject methods, the subject rAAV virion is intravitreally delivered to the eye in an amount effective to deliver the polynucleotide of interest to 10% or more, 15% or more, 20% or more, 30% or more, 40% or more, or 50% or more of the subject's cone photoreceptors, e.g., 60% or more, 70% or more, 80% or more, or 90% or more of the subject's cone photoreceptors, in some instance, 95% or more, 98% or more, or 100% of the subject's cone photoreceptors to provide therapeutic benefit to the subject individual. Put another way, following the administering, 10% or more, 15% or more, 20% or more, 30% or more, 40% or more, or 50% or more, in some instance 60% or more, 70% or more, 80% or more, or 90% or more, e.g., 95%, 98%, or 100% of the cones, will comprise a sufficient amount of the polynucleotide of interest to have an impact on cone viability and/or function, e.g., to treat or prevent a color vision deficiency. In some embodiments, the transduced cones photoreceptors will be located throughout the retina. In some embodiments, the transduced cone photoreceptors will be cones in the fovea and foveola. In some embodiments, the transduced cone photoreceptors will be foveal cones, i.e., L- or M-cones located in the fovea.

Certain embodiments comprise treating the subject in both eyes simultaneously (or nearly so), for example, at the same time or substantially the same time (i.e., the same visit). Certain embodiments comprising treating the subject in each eye sequentially, for example, wherein the interval between administering a dosage to the first eye and administering a dosage to the second eye is about or at least about 1, 2, 3, 4, 5, 6, 7, 8, 9, 10, 11, 12, 13, or 14 days, or about or at least about 2 weeks, 3 weeks, 4 weeks, 6 weeks, or 8 weeks. In some embodiments, the dosage administered to the first eye is approximately or substantially equal to the dosage administered to the second eye. In certain embodiments, the dosage administered to the second eye is greater than the dosage administered to the first eye, including wherein the second dosage is about 1.5×, 2×, 2.5×, 3×, or 3.5× the first dosage.

There are a number of ways to detect the expression of a transgene (e.g., L-opsin protein), any of which may be used in the subject embodiments. For example, expression may be detected directly, i.e., by measuring the amount of gene product, for example, at the RNA level, e.g., by RT-PCR, Northern blot, RNAse protection; or at the protein level, e.g., by Western blot, ELISA, immunohistochemistry, and the like. As another example, expression may be detected indirectly, i.e., by detecting the impact of the gene product on the viability or function of the cone photoreceptor in the subject. For example, if the gene product encoded by the transgene improves the viability of the cone cell, the expression of the transgene may be detected by detecting an improvement in viability of the cone cell, e.g., by fundus photography, Optical coherence tomography (OCT), Adaptive Optics (AO), and the like. If the gene product encoded by the transgene alters the activity of the cone cell, the expression of the transgene may be detected by detecting a change in the activity of the cone cell, e.g., by electroretinogram (ERG) and color ERG (cERG); functional adaptive optics; color vision tests such as pseudoisochromatic plates (Ishihara plates, Hardy-Rand-Ritter polychromatic plates), the Farnsworth-Munsell 100 hue test, the Farnsworth's panel D-15, the City university test, Kollner's rule, and the like; and visual acuity tests such as the ETDRS letters test, Snellen visual acuity test, visual field test, contrast sensitivity test, and the like, as a way of detecting the presence of the delivered polynucleotide. In some instances, both an improvement in viability and a modification in cone cell function may be detected.

In some embodiments, the subject method results in a therapeutic benefit, e.g., preventing the development of a disorder, halting the progression of a disorder, reversing the progression of a disorder, etc. In some embodiments, the subject method comprises the step of detecting that a therapeutic benefit has been achieved. In specific embodiments, intravitreally administering the rAAV vector improves color discrimination, increases visual acuity, decreases nystagmus, and/or decreases photophobia in the subject. The ordinarily skilled artisan will appreciate that such measures of therapeutic efficacy will be applicable to the particular disease being modified, and will recognize the appropriate detection methods to use to measure therapeutic efficacy. For example, therapeutic efficacy in treating a progressive cone dysfunction may be observed as a reduction in the rate of progression of cone dysfunction, as a cessation in the progression of cone dysfunction, or as an improvement in cone function, effects which may be observed by, e.g., ERG and/or cERG; color vision tests; functional adaptive optics; and/or visual acuity tests, for example, by comparing test results after administration of the subject composition to test results before administration of the subject composition and detecting a change in cone viability and/or function. Also, therapeutic efficacy in treating a color vision deficiency may be observed as an alteration in the individual's perception of color, e.g., in the perception of red wavelengths, in the perception of green wavelengths, in the perception of blue wavelengths, effects which may be observed by, e.g., cERG and color vision tests, for example, by comparing test results after administration of the subject composition to test results before administration of the subject composition and detecting a change in cone viability and/or function.

Expression of a transgene delivered by the subject rAAV is expected to be robust. Accordingly, in some instances, the expression of the transgene, e.g., as detected by measuring levels of gene product, by measuring therapeutic efficacy, etc., may be observed two months or less after administration, e.g., 4, 3 or 2 weeks or less after administration, for example, 1 week after administration of the subject composition. Expression of the transgene is also expected to persist over time. Accordingly, in some instances, the expression of the transgene, e.g., as detected by measuring levels of gene product, by measuring therapeutic efficacy, etc., may be observed 2 months or more after administration of the subject composition, e.g., 4, 6, 8, or 10 months or more, in some instances 1 year or more, for example, 2, 3, 4, or 5 years, in certain instances, more than 5 years.

Individual doses are typically not less than an amount required to produce a measurable effect on the subject, and may be determined based on the pharmacokinetics and pharmacology for absorption, distribution, metabolism, and excretion ("ADME") of the subject composition or its by-products, and thus based on the disposition of the composition within the subject. This includes consideration of the route of administration as well as dosage amount, which can be adjusted for intravitreal (applied to the vitreous for a pan-retinal effect) applications. Based on the parameters described herein, optimal amounts of dose and/or dose regimen can be determined empirically from individual clinician-patient relationships, as well as in vitro and in vivo assays such as those described herein and illustrated in the Experimental section, below.

Dosage Forms and Pharmaceutical Compositions

In some embodiments, e.g., gene therapy uses, it will be desirable to formulate the subject rAAV as a dosage form or pharmaceutical composition, as measured by vector genomes per eye. For instance, particular embodiments include an intravitreal dosage form, comprising rAAV vector described herein at a dosage ranging from about $1 \times 10^{10}$ to about $1 \times 10^{12}$ vector genomes (vg)/eye, for example, a dosage of about $1 \times 10^{10}$, about $2 \times 10^{10}$, about $3 \times 10^{10}$, about $4 \times 10^{10}$, about $5 \times 10^{10}$, about $6 \times 10^{10}$, about $7 \times 10^{10}$, about $8 \times 10^{10}$, about $9 \times 10^{10}$, about $1 \times 10^{11}$, about $2 \times 10^{11}$, about $3 \times 10^{11}$, about $4 \times 10^{11}$, about $5 \times 10^{11}$, about $6 \times 10^{11}$, about $7 \times 10^{11}$, about $8 \times 10^{11}$, about $9 \times 10^{11}$, or about $1 \times 10^{12}$ vg/eye.

Particular dosage forms comprise the rAAV vector at a dosage ranging from about $1 \times 10^{10}$ to about $2 \times 10^{10}$ vg/eye, about $1 \times 10^{10}$ to about $3 \times 10^{10}$ vg/eye, about $1 \times 10^{10}$ to about $4 \times 10^{10}$ vg/eye, about $1 \times 10^{10}$ to about $5 \times 10^{10}$ vg/eye, about $1 \times 10^{10}$ to about $6 \times 10^{10}$ vg/eye, about $1 \times 10^{10}$ to about $7 \times 10^{10}$ vg/eye, about $1 \times 10^{10}$ to about $8 \times 10^{10}$ vg/eye, about $1 \times 10^{10}$ to about $9 \times 10^{10}$ vg/eye, about $1 \times 10^{10}$ to about $1 \times 10^{11}$ vg/eye, about $1 \times 10^{10}$ to about $2 \times 10^{11}$ vg/eye, about $1 \times 10^{10}$ to about $3 \times 10^{11}$ vg/eye, about $1 \times 10^{10}$ to about $4 \times 10^{11}$ vg/eye, about $1 \times 10^{10}$ to about $5 \times 10^{11}$ vg/eye, about $1 \times 10^{10}$ to about $6 \times 10^{11}$ vg/eye, about $1 \times 10^{10}$ to about $7 \times 10^{11}$ vg/eye, about $1 \times 10^{10}$ to about $8 \times 10^{11}$ vg/eye, about $1 \times 10^{10}$ to about $9 \times 10^{11}$ vg/eye, about $1 \times 10^{10}$ to about $1 \times 10^{12}$ vg/eye, about $2 \times 10^{10}$ to about $3 \times 10^{10}$ vg/eye, about $2 \times 10^{10}$ to about $4 \times 10^{10}$ vg/eye, about $2 \times 10^{10}$ to about $5 \times 10^{10}$ vg/eye, about $2 \times 10^{10}$ to about $6 \times 10^{10}$ vg/eye, about $2 \times 10^{10}$ to about $7 \times 10^{10}$ vg/eye, about $2 \times 10^{10}$ to about $8 \times 10^{10}$ vg/eye, about $2 \times 10^{10}$ to about $9 \times 10^{10}$ vg/eye, about $2 \times 10^{10}$ to about $1 \times 10^{11}$ vg/eye, about $2 \times 10^{10}$ to about $2 \times 10^{11}$ vg/eye, about $2 \times 10^{10}$ to about $3 \times 10^{11}$ vg/eye, about $2 \times 10^{10}$ to about $4 \times 10^{11}$ vg/eye, about $2 \times 10^{10}$ to about $5 \times 10^{11}$ vg/eye, about $2 \times 10^{10}$ to about $6 \times 10^{11}$ vg/eye, about $2 \times 10^{10}$ to about $7 \times 10^{11}$ vg/eye, about $2 \times 10^{10}$ to about $8 \times 10^{11}$ vg/eye, about $2 \times 10^{10}$ to about $9 \times 10^{11}$ vg/eye, about $2 \times 10^{10}$ to about $1 \times 10^{12}$ vg/eye, about $3 \times 10^{10}$ to about $4 \times 10^{10}$ vg/eye, about $3 \times 10^{10}$ to about $5 \times 10^{10}$ vg/eye, about $3 \times 10^{10}$ to about $6 \times 10^{10}$ vg/eye, about $3 \times 10^{10}$ to about $7 \times 10^{10}$ vg/eye, about $3 \times 10^{10}$ to about $8 \times 10^{10}$ vg/eye, about $3 \times 10^{10}$ to about $9 \times 10^{10}$ vg/eye, about $3 \times 10^{10}$ to about $1 \times 10^{11}$ vg/eye, about $3 \times 10^{10}$ to about $2 \times 10^{11}$ vg/eye, about $3 \times 10^{10}$ to about $3 \times 10^{11}$ vg/eye, about $3 \times 10^{10}$ to about $4 \times 10^{11}$ vg/eye, about $3 \times 10^{10}$ to about $5 \times 10^{11}$ vg/eye, about $3 \times 10^{10}$ to about $6 \times 10^{11}$ vg/eye, about $3 \times 10^{10}$ to about $7 \times 10^{11}$ vg/eye, about $3 \times 10^{10}$ to about $8 \times 10^{11}$ vg/eye, about $3 \times 10^{10}$ to about $9 \times 10^{11}$ vg/eye, about $3 \times 10^{10}$ to about $1 \times 10^{12}$ vg/eye, about $4 \times 10^{10}$ to about $5 \times 10^{10}$ vg/eye, about $4 \times 10^{10}$ to about $6 \times 10^{10}$ vg/eye, about $4 \times 10^{10}$ to about $7 \times 10^{10}$ vg/eye, about $4 \times 10^{10}$ to about $8 \times 10^{10}$ vg/eye, about $4 \times 10^{10}$ to about $9 \times 10^{10}$ vg/eye, about $4 \times 10^{10}$ to about $1 \times 10^{11}$ vg/eye, about $4 \times 10^{10}$ to about $2 \times 10^{11}$ vg/eye, about $4 \times 10^{10}$ to about $3 \times 10^{11}$ vg/eye, about $4 \times 10^{10}$ to about $4 \times 10^{11}$ vg/eye, about $4 \times 10^{10}$ to about $5 \times 10^{11}$ vg/eye, about $4 \times 10^{10}$ to about $6 \times 10^{11}$ vg/eye, about $4 \times 10^{10}$ to about $7 \times 10^{11}$ vg/eye, about $4 \times 10^{10}$ to about $8 \times 10^{11}$ vg/eye, about $4 \times 10^{10}$ to about $9 \times 10^{11}$ vg/eye, about $4 \times 10^{10}$ to about $1 \times 10^{12}$ vg/eye, about $5 \times 10^{10}$ to about $6 \times 10^{10}$ vg/eye, about $5 \times 10^{10}$ to about $7 \times 10^{10}$ vg/eye, about $5 \times 10^{10}$ to about $8 \times 10^{10}$ vg/eye, about $5 \times 10^{10}$ to about $9 \times 10^{10}$ vg/eye, about $5 \times 10^{10}$ to about $1\times10^{11}$ vg/eye, about $5\times10^{10}$ to about $2\times10^{11}$ vg/eye, about $5\times10^{10}$ to about $3\times10^{11}$ vg/eye, about $5\times10^{10}$ to about $4\times10^{11}$ vg/eye, about $5\times10^{10}$ to about $5\times10^{11}$ vg/eye, about $5\times10^{10}$ to about $6\times10^{11}$ vg/eye, about $5\times10^{10}$ to about $7\times10^{11}$ vg/eye, about $5\times10^{10}$ to about $8\times10^{11}$ vg/eye, about $5\times10^{10}$ to about $9\times10^{11}$ vg/eye, about $5\times10^{10}$ to about $1\times10^{12}$ vg/eye, about $6\times10^{10}$ to about $7\times10^{10}$ vg/eye, about $6\times10^{10}$ to about $8\times10^{10}$ vg/eye, about $6\times10^{10}$ to about $9\times10^{10}$ vg/eye, about $6\times10^{10}$ to about $1\times10^{11}$ vg/eye, about $6\times10^{10}$ to about $2\times10^{11}$ vg/eye, about $6\times10^{10}$ to about $3\times10^{11}$ vg/eye, about $6\times10^{10}$ to about $4\times10^{11}$ vg/eye, about $6\times10^{10}$ to about $5\times10^{11}$ vg/eye, about $6\times10^{10}$ to about $6\times10^{11}$ vg/eye, about $6\times10^{10}$ to about $7\times10^{11}$ vg/eye, about $6\times10^{10}$ to about $8\times10^{11}$ vg/eye, about $6\times10^{10}$ to about $9\times10^{11}$ vg/eye, about $6\times10^{11}$ to about $1\times10^{11}$ vg/eye, about $7\times10^{11}$ to about $8\times10^{11}$ vg/eye, about $7\times10^{10}$ to about $9\times10^{10}$ vg/eye, about $7\times10^{10}$ to about $1\times10^{11}$ vg/eye, about $7\times10^{10}$ to about $2\times10^{11}$ vg/eye, about $7\times10^{10}$ to about $3\times10^{11}$ vg/eye, about $7\times10^{10}$ to about $4\times10^{11}$ vg/eye, about $7\times10^{10}$ to about $5\times10^{11}$ vg/eye, about $7\times10^{10}$ to about $6\times10^{11}$ vg/eye, about $7\times10^{10}$ to about $7\times10^{11}$ vg/eye, about $7\times10^{10}$ to about $8\times10^{11}$ vg/eye, about $7\times10^{10}$ to about $9\times10^{11}$ vg/eye, about $7\times10^{10}$ to about $1\times10^{12}$ vg/eye, about $8\times10^{10}$ to about $9\times10^{10}$ vg/eye, about $8\times10^{10}$ to about $1\times10^{11}$ vg/eye, about $8\times10^{10}$ to about $2\times10^{11}$ vg/eye, about $8\times10^{10}$ to about $3\times10^{11}$ vg/eye, about $8\times10^{10}$ to about $4\times10^{11}$ vg/eye, about $8\times10^{10}$ to about $5\times10^{11}$ vg/eye, about $8\times10^{10}$ to about $6\times10^{11}$ vg/eye, about $8\times10^{10}$ to about $7\times10^{11}$ vg/eye, about $8\times10^{10}$ to about $8\times10^{11}$ vg/eye, about $8\times10^{10}$ to about $9\times10^{11}$ vg/eye, about $8\times10^{10}$ to about $1\times10^{12}$ vg/eye, about $9\times10^{10}$ to about $1\times10^{11}$ vg/eye, about $9\times10^{10}$ to about $2\times10^{11}$ vg/eye, about $9\times10^{10}$ to about $3\times10^{11}$ vg/eye, about $9\times10^{10}$ to about $4\times10^{11}$ vg/eye, about $9\times10^{10}$ to about $5\times10^{11}$ vg/eye, about $9\times10^{10}$ to about $6\times10^{11}$ vg/eye, about $9\times10^{10}$ to about $7\times10^{11}$ vg/eye, about $9\times10^{10}$ to about $8\times10^{11}$ vg/eye, about $9\times10^{10}$ to about $9\times10^{11}$ vg/eye, about $9\times10^{10}$ to about $1\times10^{12}$ vg/eye, about $1\times10^{11}$ to about $2\times10^{11}$ vg/eye, about $1\times10^{11}$ to about $3\times10^{11}$ vg/eye, about $1\times10^{11}$ to about $4\times10^{11}$ vg/eye, about $1\times10^{11}$ to about $5\times10^{11}$ vg/eye, about $1\times10^{11}$ to about $6\times10^{11}$ vg/eye, about $1\times10^{11}$ to about $7\times10^{11}$ vg/eye, about $1\times10^{11}$ to about $8\times10^{11}$ vg/eye, about $1\times10^{11}$ to about $9\times10^{11}$ vg/eye, about $1\times10^{11}$ to about $1\times10^{12}$ vg/eye, about $2\times10^{11}$ to about $3\times10^{11}$ vg/eye, about $2\times10^{11}$ to about $4\times10^{11}$ vg/eye, about $2\times10^{11}$ to about $5\times10^{11}$ vg/eye, about $2\times10^{11}$ to about $6\times10^{11}$ vg/eye, about $2\times10^{11}$ to about $7\times10^{11}$ vg/eye, about $2\times10^{11}$ to about $8\times10^{11}$ vg/eye, about $2\times10^{11}$ to about $9\times10^{11}$ vg/eye, about $2\times10^{11}$ to about $1\times10^{12}$ vg/eye, about $3\times10^{11}$ to about $4\times10^{11}$ vg/eye, about $3\times10^{11}$ to about $5\times10^{11}$ vg/eye, about $3\times10^{11}$ to about $6\times10^{11}$ vg/eye, about $3\times10^{11}$ to about $7\times10^{11}$ vg/eye, about $3\times10^{11}$ to about $8\times10^{11}$ vg/eye, about $3\times10^{11}$ to about $9\times10^{11}$ vg/eye, about $3\times10^{11}$ to about $1\times10^{12}$ vg/eye, about $4\times10^{11}$ to about $5\times10^{11}$ vg/eye, about $4\times10^{11}$ to about $6\times10^{11}$ vg/eye, about $4\times10^{11}$ to about $7\times10^{11}$ vg/eye, about $4\times10^{11}$ to about $8\times10^{11}$ vg/eye, about $4\times10^{11}$ to about $9\times10^{11}$ vg/eye, about $4\times10^{11}$ to about $1\times10^{12}$ vg/eye, about $5\times10^{11}$ to about $6\times10^{11}$ vg/eye, about $5\times10^{11}$ to about $7\times10^{11}$ vg/eye, about $5\times10^{11}$ to about $8\times10^{11}$ vg/eye, about $5\times10^{11}$ to about $9\times10^{11}$ vg/eye, about $5\times10^{11}$ to about $1\times10^{12}$ vg/eye, about $6\times10^{11}$ to about $7\times10^{11}$ vg/eye, about $6\times10^{11}$ to about $8\times10^{11}$ vg/eye, about $6\times10^{11}$ to about $9\times10^{11}$ vg/eye, about $6\times10^{11}$ to about $1\times10^{12}$ vg/eye, about $7\times10^{11}$ to about $8\times10^{11}$ vg/eye, about $7\times10^{11}$ to about $9\times10^{11}$ vg/eye, about $7\times10^{11}$ to about $1\times10^{12}$ vg/eye, about $8\times10^{11}$ to about $9\times10^{11}$ vg/eye, about $8\times10^{11}$ to about $1\times10^{12}$ vg/eye, or about $9\times10^{11}$ to about $1\times10^{12}$ vg/eye.

Specific dosage forms comprise the rAAV vector at a dosage ranging from about $6\times10^{10}$ to about $6\times10^{11}$ vg/eye, for example, a dosage ranging from about $6\times10^{10}$ to about $7\times10^{10}$ vg/eye, about $6\times10^{10}$ to about $8\times10^{10}$ vg/eye, about $6\times10^{10}$ to about $9\times10^{10}$ vg/eye, about $6\times10^{10}$ to about $1\times10^{11}$ vg/eye, about $6\times10^{10}$ to about $2\times10^{11}$ vg/eye, about $6\times10^{10}$ to about $3\times10^{11}$ vg/eye, about $6\times10^{10}$ to about $4\times10^{11}$ vg/eye, about $6\times10^{10}$ to about $5\times10^{11}$ vg/eye, about $6\times10^{10}$ to about $6\times10^{11}$ vg/eye, about $7\times10^{10}$ to about $8\times10^{10}$ vg/eye, about $7\times10^{10}$ to about $9\times10^{10}$ vg/eye, about $7\times10^{10}$ to about $1\times10^{11}$ vg/eye, about $7\times10^{10}$ to about $2\times10^{11}$ vg/eye, about $7\times10^{10}$ to about $3\times10^{11}$ vg/eye, about $7\times10^{10}$ to about $4\times10^{11}$ vg/eye, about $7\times10^{10}$ to about $5\times10^{11}$ vg/eye, about $7\times10^{10}$ to about $6\times10^{11}$ vg/eye, about $8\times10^{10}$ to about $9\times10^{10}$ vg/eye, about $8\times10^{10}$ to about $1\times10^{11}$ vg/eye, about $8\times10^{10}$ to about $2\times10^{11}$ vg/eye, about $8\times10^{10}$ to about $3\times10^{11}$ vg/eye, about $8\times10^{10}$ to about $4\times10^{11}$ vg/eye, about $8\times10^{10}$ to about $5\times10^{11}$ vg/eye, about $8\times10^{10}$ to about $6\times10^{11}$ vg/eye, about $9\times10^{10}$ to about $1\times10^{11}$ vg/eye, about $9\times10^{10}$ to about $2\times10^{11}$ vg/eye, about $9\times10^{10}$ to about $3\times10^{11}$ vg/eye, about $9\times10^{10}$ to about $4\times10^{11}$ vg/eye, about $9\times10^{10}$ to about $5\times10^{11}$ vg/eye, about $9\times10^{10}$ to about $6\times10^{11}$ vg/eye, about $1\times10^{11}$ to about $2\times10^{11}$ vg/eye, about $1\times10^{11}$ to about $3\times10^{11}$ vg/eye, about $1\times10^{11}$ to about $4\times10^{11}$ vg/eye, about $1\times10^{11}$ to about $5\times10^{11}$ vg/eye, about $1\times10^{11}$ to about $6\times10^{11}$ vg/eye, about $2\times10^{11}$ to about $3\times10^{11}$ vg/eye, about $2\times10^{11}$ to about $4\times10^{11}$ vg/eye, about $2\times10^{11}$ to about $5\times10^{11}$ vg/eye, about $2\times10^{11}$ to about $6\times10^{11}$ vg/eye, about $3\times10^{11}$ to about $4\times10^{11}$ vg/eye, about $3\times10^{11}$ to about $5\times10^{11}$ vg/eye, about $3\times10^{11}$ to about $6\times10^{11}$ vg/eye, about $4\times10^{11}$ to about $5\times10^{11}$ vg/eye, about $4\times10^{11}$ to about $6\times10^{11}$ vg/eye, or about $5\times10^{11}$ to about $6\times10^{11}$ vg/eye.

In specific embodiments, the dosage form is for single use in each eye for treating a color vision deficiency in a human subject in need thereof.

In certain embodiments, a dosage form or pharmaceutical composition comprises a vector or virion (e.g., rAAV) described herein and one or more pharmaceutically acceptable carriers, diluents, or excipients. Pharmaceutical compositions suitable for use include sterile aqueous solutions or dispersions and sterile powders for the extemporaneous preparation of sterile injectable solutions or dispersion. In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the internal compositions can be brought about by including in the composition an agent which delays absorption, for example, aluminum monostearate and gelatin.

Sterile solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof In some embodiments, rAAV vectors are prepared with carriers that will protect the vector against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

In some embodiments, dosage forms and pharmaceutical compositions comprise, but are not limited to, solutions, emulsions, and liposome-containing formulations. These compositions may be generated from a variety of components that comprise, but are not limited to, preformed liquids, self-emulsifying solids and self-emulsifying semi-solids.

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The co-administration of a nucleic acid and a carrier compound, typically with an excess of the latter substance, can result in a substantial reduction of the amount of nucleic acid recovered in the liver, kidney or other extra circulatory reservoirs, presumably due to competition between the carrier compound and the nucleic acid for a common receptor. For example, the recovery of a partially phosphorothioate oligonucleotide in hepatic tissue can be reduced when it is co-administered with polyinosinic acid, dextran sulphate, polycytidic acid or 4-acetamido-4'isothiocyano-stilbene-2,2'disulfonic acid (Miyao et al., Antisense Res. Dev., 1995, 5, 115-121; Takakura et al., Antisense & Nucl. Acid Drug Dev., 1996, 6, 177-183).

The subject rAAV can be incorporated into dosage forms or pharmaceutical compositions for administration to mammalian patients, particularly humans. The virions can be formulated in nontoxic, inert, pharmaceutically acceptable aqueous carriers, preferably at a pH ranging from 3 to 8, more preferably ranging from 6 to 8. Such sterile compositions will comprise the vector or virion containing the nucleic acid encoding the therapeutic molecule dissolved in an aqueous buffer having an acceptable pH upon reconstitution.

In some embodiments, the dosage forms and pharmaceutical compositions provided herein comprise a therapeutically effective amount of a vector or virion in admixture with a pharmaceutically acceptable carrier and/or excipient, for example saline, phosphate buffered saline, phosphate and amino acids, polymers, polyols, sugar, buffers, preservatives and other proteins. Exemplary amino acids, polymers and sugars and the like are octylphenoxy polyethoxy ethanol compounds, polyethylene glycol monostearate compounds, polyoxyethylene sorbitan fatty acid esters, sucrose, fructose, dextrose, maltose, glucose, mannitol, dextran, sorbitol, inositol, galactitol, xylitol, lactose, trehalose, bovine or human serum albumin, citrate, acetate, Ringer's and Hank's solutions, cysteine, arginine, carnitine, alanine, glycine, lysine, valine, leucine, polyvinylpyrrolidone, polyethylene and glycol. Preferably, this formulation is stable for at least six months at 4° C.

In some embodiments, the dosage forms and pharmaceutical composition provided herein comprises a buffer, such as phosphate buffered saline (PBS) or sodium phosphate/sodium sulfate, tris buffer, glycine buffer, sterile water and other buffers known to the ordinarily skilled artisan such as those described by Good et al. (1966) Biochemistry 5:467. The pH of the buffer in which the pharmaceutical composition comprising the tumor suppressor gene contained in the adenoviral vector delivery system, may be in the range of 6.5 to 7.75, preferably 7 to 7.5, and most preferably 7.2 to 7.4.

In some embodiments, the dosage forms and pharmaceutical composition provided herein comprises substances which increase the viscosity of the suspension, such as sodium carboxymethyl cellulose, sorbitol, or dextran, in the amount about 1-10 percent, such as 1, 2, 3, 4, 5, 6, 7, 8, 9, or 10 percent.

The dosage forms and pharmaceutical compositions can be included in a container, pack, or dispenser together with instructions for administration.

In some instances, e.g., for intravitreal administration, it may be especially advantageous to formulate the pharmaceutical composition in dosage form for ease of administration and uniformity of dosage. Dosage forms as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

Example 1

Preclinical Evaluation of an Intravitreal Gene Therapy Vector for the Treatment of Blue Cone Monochromacy Experiments were performed to evaluate a replication-incompetent AAV-based gene therapy for the treatment of BCM in animals. The vector comprises the AAV2.7m8 capsid, expresses human OPN1LW under the control of the synthetic cone cell-specific expression cassette, MNTC, which drives robust protein expression in M- and L-cone photoreceptors (see U.S. Application No. 2015/025939), and is flanked by inverted terminal repeats (ITRs) derived from AAV2. The recombinant vector genome structure is shown in FIG. 1.

Materials and Methods

Vectors. The studies reported here used three different recombinant AAV constructs, flanked by AAV2 ITRs packaged in the AAV2.7m8 capsid variant: (1) ADVM-062, (2) ADVM-062.myc, and (3) AAV2.7m8-MNTC-GFP that expresses the GFP reporter gene under the control of the MNTC promoter.

ADVM-062 utilizes the AAV2 capsid variant, AAV2.7m8. The rAAV genome consists of the MNTC-L-opsin expression cassette, flanked by the AAV2 inverted terminal repeats (ITRs). The synthetic MNTC cassette includes an LCR enhancer sequence from the L- and M-opsin genomic locus and a truncated promoter sequence from the M-Opsin gene, comprising about 140 nucleotides upstream of the transcriptional start site. In addition, the cassette includes a 5' UTR based on the M-opsin 5'UTR but modified to have minimal secondary structure and to include additional sequence at its 3' end, into which an intron was inserted. The intronic sequence is a pSI chimeric intron having the 5'-donor site from the first intron of the human β-globin gene and the branch and 3'-acceptor site from the intron that lies between the leader and the body of an immunoglobulin gene heavy chain variable region. The sequences of the donor and acceptor sites, along with the branchpoint site, were changed to match the consensus sequences for splicing. The human L-opsin cDNA sequence is followed by a 3'UTR that corresponds to the downstream genomic region of M-opsin. Also included in the pMNTC polynucleotide cassette is a strong Kozak sequence and an SV40 polyadenylation sequence (FIG. 1).

To enable detection of AAV2.7m8-MNTC-driven expression of the transgene in vivo, using scanning laser ophthalmoscope (SLO), and ex vivo, we utilized AAV2.7m8-MNTC-GFP, which carried the GFP reporter gene under the control of the MNTC promoter.

To enable detection and localization of human L-opsin in the presence of endogenous opsins and to quantify the efficacy of transduction based on percentage of human L-opsin-positive cones, we engineered ADVM-062.myc to express human L-opsin with a C-terminal myc tag. With the exception of the myc-tag inserted in-frame into the OPN1LW coding sequence, ADVM-062.myc was identical to ADVM-062. To ensure comparability of results acquired from the animals treated with either vector, ADVM-062 and ADVM-062.myc vectors were produced and characterized using similar processes and protocols.

Both ADVM-062 and ADVM-062.myc were manufactured in the baculovirus expression vector system (BEVS) under cGMP conditions in an Sf9 working cell bank (WCB). In this system, two baculoviruses were used, one encoding the AAV2 Rep and AAV2.7m8 Cap proteins and another encoding the human L-opsin cDNA expression cassette. AAV2.7m8-MNTC-GFP was produced using the triple transfection method in HEK293 cells and purified by iodixanol gradient ultracentrifugation (see Choi et al., Curr Protoc Hum Genet. 2007 April; Chapter 12( ):Unit 12.9). AAV vectors were titered by quantitative PCR (qPCR) using Taqman probes (Thermo Fischer Scientific).

Animals and Study Design (African green monkeys—*Chlorocebus sabaeus*). The studies with AAV2.7m8-MNTC-GFP were conducted in adult (5-12 years old) African green monkeys (*Chlorocebus sabaeus*) of both sexes (n=2). Monkeys were anesthetized with intramuscular injection of 8.0 mg/kg ketamine/1.6 mg/kg xylazine and mydriasis achieved with topical 10% phenylephrine. An eye speculum was placed in the eye to facilitate injections. For IVT injections (n=4 eyes/condition), 50 μL of AAV2.7m8-MNTC-GFP vector was delivered to yield a final dose of $5\times10^{11}$ vg per eye. IVT injections to the central vitreous were administered using a 31-gauge 31 G ⅝₁₆-inch needle (inserted inferotemporally at the level of the ora serrata~2.5 mm posterior to the limbus. Central vitreous placement was confirmed by direct observation of the needle tip at the time of the injection. Following IVT injections a topical triple antibiotic ointment was administered.

Retinal examination and fundus color imaging were performed by using a Topcon TRC-50EX retinal camera with Canon 6D digital imaging hardware and New Vision Fundus Image Analysis System software and Spectralis OCT Plus.

Animals and Study Design (Cynomolgus monkeys—*Macaca fascicularis*). ADVM-062 and ADVM-062.myc expression and tolerability studies were conducted in 2.5-2.8 years old males. Animals were randomized into 7 treatment groups, 3 per group by weight and neutralizing antibody (Nab) titer (Table S1). Group 1 was treated with IVT-injected vehicle. Groups 2, 3, and 4 were treated with ADVM-062.myc IVT injected at $5\times10^9$, $5\times10^{10}$ and $5\times10^{11}$ vg/eye, respectively. Groups 5, 6, and 7 were treated with the equivalent doses of ADVM-062. All animals were evaluated for the treatment safety and tolerability. At termination, one eye from each treatment subgroup was processed for histopathology. In vehicle-treated group 1 and ADVM-062-treated groups 5, 6, and 7, all retinas not selected for histopathology were analyzed for dose-dependent expression of human L-opsin protein by LC-MS-MS. In ADVM-062.myc treated groups 2, 3, and 4, all right eyes were fixed and processed for the detection of human L-opsin.myc by immunofluorescence. Retinas from the left eyes were analyzed for dose-dependent expression of human L-opsin protein by LC-MS-MS (Table S1). The second study expanded testing with the doses of $3\times10^{10}$ and $5\times10^{10}$ vg/eye. Animals were randomized to 3 treatment groups. Groups 1 and 2 (3 animals in each) was treated with ADVM-062 or ADVM-062.myc at $3\times10^{10}$ vg/eye, respectively. Group 3 (2 animals) was treated with ADVM-062 or ADVM-062.myc injected in 50 µL at $5\times10^{10}$ vg/eye to the left and right eye, respectively (Table S1). All retinas from ADVM-062-dosed eyes from all treatment groups and right eyes of group 2 dosed with ADVM-062.myc were analyzed for human L-opsin protein expression. Left eyes from group 2 and group 3 (ADVM-062.myc-dosed) were analyzed by the immunofluorescence for transgenic human L-opsin.myc localization and percentage of the transgene-positive cones in fovea.

All animals were in the normal range at baseline ophthalmic screening, including tonometry, slit lamp biomicroscopy, fundoscopy, fluorescein angiography (FA), and optical coherence tomography (OCT). All animals recruited in the study were pre-screened for the neutralizing antibody (Nab); only Nab-negative animals were assigned to the ADVM-062 treatment groups.

Animal Care and Handling. Animals were anesthetized for all procedures and ophthalmic evaluations using intramuscular ketamine/dexdomitor. General well-being was assessed before, during, and after sedation as well as twice daily on non-procedure days. The daily consumption of food biscuits was monitored. Body weight was measured at the time of ophthalmic examinations.

Test article delivery. IVT doses were administered under local anesthesia (0.5% proparacaine) using a 31-gauge ⁵⁄₁₆-inch needle (Ulticare Vet RX U-100, #09436) 2 mm posterior to the limbus in the inferior temporal quadrant, targeting the central vitreous body. Alternatively, IVT doses were administered under local anesthesia (0.5% proparacaine). The eye was positioned into place with a cotton tipped applicator or the conjunctival tissue held with forceps and a 30 G needle attached to a 1 mL luer lock syringe was used to inject into the eye at a 45 degree angle pointed towards the optic nerve, avoiding the lens. The injection needle was inserted into the superior temporal region, approximately 3 mm from the limbus. The intravitreal dose was injected to posterior pole of the eye, aiming close to optic disc region. After injection the needle was slowly removed and monitored for efflux. Antibiotic ointment was applied immediately post dose. In both cases, injections were followed by topical administration of 0.3% ciprofloxacin ophthalmic solution and 1% atropine ophthalmic ointment.

In-life studies. Slit lamp biomicroscopy was used to examine the anterior segment, lens, and anterior vitreous body. Indirect ophthalmoscopy was used to examine the vitreous, fundus, and optic disc. For ERGs, animals were anesthetized and pupils were dilated with 1% tropicamide. Animals were dark-adapted for at least 1 hour before the scotopic tests, and light-adapted for at least 10 minutes before the photopic tests. Animals were fasted at least 2 hours before ERG procedures. Optical Coherence Tomography (OCTs) were acquired using the Heidelberg Spectralis. Scan acquisition was as follows: infrared plus optical coherence tomography (IR+OCT), blue reflectance (BR), and BluePeak autofluorescence (BAF). Fluorescein angiography (FA) was performed following IV injection of 10% fluorescein sodium (0.1 mL/kg). An SLO image was generated during the IR scan to capture representative images of each eye.

At completion of the in-life part of the study, animals were euthanized by intravenous (IV) injection of a commercially available veterinary euthanasia solution (identified in the study record), followed by exsanguination. Ocular tissues were collected for histopathology (Groups 1-7), analysis of human L-opsin expression by myc-tag immunofluorescence (Groups 4-6), and human L-opsin protein analysis by LC-MS-MS, according to the procedures detailed below according to the assignments made at the initiation of the study, as shown in Table S1 below.

TABLE S1

NHP Study Design

| Study | Group No. | Animal No. | Treatment | Dose Level (vg/eye) | Assessments | Right Eye (OD) | Left Eye (OS) |
|---|---|---|---|---|---|---|---|
| 1 | 1 | 1.1001 | OU: Vehicle | 0 | Ophthalmic | Histopathology | hL-opsin LC-MS* |
|   |   | 1.1002 | Control |   | Examinations, | hL-opsin LC-MS | hL-opsin LC-MS |
|   |   | 1.1003 |   |   | IOP at pre- | hL-opsin LC-MS | hL-opsin LC-MS |
|   | 2 | 1.2001 | OU: ADVM- | $5 \times 10^9$ | treatment and | hL-opsin-myc IF** | hL-opsin LC-MS |
|   |   | 1.2002 | 062.myc |   | Days 3, 15, and | hL-opsin-myc IF | hL-opsin LC-MS |
|   |   | 1.2003 |   |   | during Weeks 4, | hL-opsin-myc IF | hL-opsin LC-MS |
|   | 3 | 1.3001 | OU: ADVM- | $5 \times 10^{10}$ | 6 and 8. | hL-opsin-myc IF | hL-opsin LC-MS |
|   |   | 1.3002 | 062.myc |   | ERG and OCT at | hL-opsin-myc IF | hL-opsin LC-MS |
|   |   | 1.3003 |   |   | pre-treatment | hL-opsin-myc IF | hL-opsin LC-MS |
|   | 4 | 1.4001 | OU: ADVM- | $5 \times 10^{11}$ | and during | hL-opsin-myc IF | hL-opsin LC-MS |
|   |   | 1.4002 | 062.myc |   | Weeks 4 and 8. | hL-opsin-myc IF | hL-opsin LC-MS |
|   |   | 1.4003 |   |   |   | hL-opsin-myc IF | hL-opsin LC-MS |
|   | 5 | 1.5001 | OU: ADVM- | $5 \times 10^9$ |   | Histopathology | hL-opsin LC-MS |
|   |   | 1.5002 | 062 |   |   | hL-opsin-myc IF | hL-opsin LC-MS |
|   |   | 1.5003 |   |   |   | hL-opsin-myc IF | hL-opsin LC-MS |
|   | 6 | 1.6001 | OU: ADVM- | $5 \times 10^{10}$ |   | Histopathology | hL-opsin LC-MS |
|   |   | 1.6002 | 062 |   |   | hL-opsin-myc IF | hL-opsin LC-MS |
|   |   | 1.6003 |   |   |   | hL-opsin-myc IF | hL-opsin LC-MS |
|   | 7 | 1.7001 | OU: ADVM- | $5 \times 10^{11}$ |   | Histopathology | hL-opsin LC-MS |
|   |   | 1.7002 | 062 |   |   | hL-opsin-myc IF | hL-opsin LC-MS |
|   |   | 1.7003 |   |   |   | hL-opsin-myc IF | hL-opsin LC-MS |

TABLE S1-continued

NHP Study Design

| Study | Group No. | Animal No. | Treatment | Dose Level (vg/eye) | Assessments | Right Eye (OD) | Left Eye (OS) |
|---|---|---|---|---|---|---|---|
| 2 | 1 | 2.1001 2.1002 2.1003 | OU: ADVM-062 | $3 \times 10^{10}$ | Ophthalmic Examinations, OCT and IOP at pre-treatment and Days 7, 14, 28, 42, & 56 ERG: pre-treatment and Day 55 | mRNA | hL-opsin LC-MS |
|  | 2 | 2.2001 2.2002 2.2003 | OU: ADVM-062.myc |  |  | mRNA | hL-opsin-myc IF |
|  | 3 | 2.3001 2.3002 | OD: ADVM-062 OS: ADVM-062.myc | $3 \times 10^{11}$ |  | hL-opsin LC-MS | hL-opsin-myc IF |

IVT = Intravitreal; OD = oculus dexter (right eye), OS = oculus sinister (left eye); OU = oculus uterque (both eyes).
*hL-opsin LC-MS designates tissue analyzed for human L-opsin transgene levels by LC-MS.
**hL-opsin-myc IF designates tissue analyzed for localization of human L-opsin-myc transgene and percentage of transgene-positive cones by myc-immunofluorescence.

In the first study, the test article was delivered to mid-vitreous. In the second study, the dose was injected to posterior pole of the eye, aiming closer to optic disc region, to explore whether administration closer to the optic disc could afford reproducible foveal cone transduction.

In both studies, the animals were sedated with ketamine and dexdomitor for the dosing procedure. In addition, atropine (0.04 mg/kg IM) was administered in the second study. The eyes were be cleansed with Betadine® (5% Ophthalmic Prep Solution) and rinsed with sterile saline. In the first study, a mydriatic (1% tropicamide) was instilled in each eye followed by a topical anesthetic (proparacaine), and the second study did not use topical mydriatics. In both studies, injections were performed in each eye.

In the first study, a lid speculum was inserted to keep the lids open during the procedure and the globe retracted. The needle of the dose syringe was inserted through the sclera and pars plana approximately 4 mm posterior to the limbus. The needle was directed posterior to the lens and advanced into the mid-vitreous. The test article was slowly injected into the mid-vitreous. Each eye received a single dose injection (50 µL per injection) into the superior temporal region.

In the second study (as in the first study), the eyes were held open with a speculum. During the injection procedure, the eye was positioned into place with a cotton tipped applicator or the conjunctival tissue was held with forceps. The injection needle was inserted into the superior temporal region, approximately 3 mm from the limbus, and directed at a 45 degree angle pointed towards the optic nerve. The intravitreal dose was injected to posterior pole of the eye, aiming closer to optic disc region.

After the injection the needle was slowly removed, and eyes were monitored for efflux. Topical ocular antibiotic was be applied immediately post dose.

It should be mentioned that the first study uses conventional IVT injection procedure to deliver gene therapy dose to mid-vitreous, a commonly used procedure for intra-ocular delivery of therapeutics. Without being bound by theory, a disadvantage of this method for IVT delivery for gene therapy aimed to transduce retinal cells is that the vector needs to diffuse through the vitreous to posterior pole of the eye to reach the target cells. Since vector particles diffuse in all directions, this will result in significant loss of vector as well as in the increased non-productive transduction of non-retinal ocular tissues with potential liabilities.

The injection of the dose close to posterior pole of the eye delivers gene therapy closer to the fovea and macula, which are retinal areas essential for human vision, thus increasing the chances of the vectors to reach the target retinal cells. Thus, this method may provide a more robust delivery of gene therapy to foveal cones, to achieve higher efficacy with lesser variability.

Animals and Study Design (Mongolian gerbils—*Meriones unguiculatus*). Ten-week-old female Mongolian gerbils (*Meriones unguiculatus*) were obtained from Charles River Laboratories, Wilmington, MA. Baseline screening by fundus imaging ensured that all animals had normal ocular health.

Test Article Administration. For IVT injections (n=8 eyes/condition), gerbils were anesthetized with a subcutaneous injection of 50 mg/kg ketamine and 10 mg/kg xylazine. Eyes were topically treated with 0.1% dexamethasone and pupils were dilated with 1% atropine. Injection was performed using a beveled 36-gauge needle mounted on a 100-µL Hamilton syringe connected to a micro-injection pump (UMP-3 UltraMicroPump, World Precision Instruments, Florida, USA) to deliver 5-6 µL of test solution into the vitreous cavity. The needle tip was allowed to remain in the eye for 1 minute to ensure complete test article dispensing. After injection, eyes were treated with topical bacitracin/atrophine/0.1% dexamethasone ointments. In vector treatment groups, animals were injected bilaterally with ADVM-062 at doses of $3.8 \times 10^8$-$3.8 \times 10^{11}$ vg per eye, or with ADVM-062.myc at $3.8 \times 10^{11}$ vg per eye. In the vehicle control group, animals were treated with injection of 5-6 µL formulation buffer (180 mM NaCl, 10 mM phosphate, 0.001% Pluronic® F-68, pH 7.3) to both eyes. Eye examinations and fundus photography were performed by using a slit lamp (Topcon) and Micron IV fundus microscope (Phoenix).

ERG and Statistical Analysis. Gerbils were anesthetized with subcutaneous injections of ketamine/xylazine (50 mg/mL ketamine, 10 mg/ml xylazine). Pupils were dilated with topical atropine ophthalmic solution (1%) and one drop of GenTeal was applied to the cornea. A subdermal reference electrode was placed in the nasal septum and a ground electrode was placed subcutaneously above the base of the tail. The animals were positioned on a temperature-controlled platform (Espion Electrophysiology System (Diagnosys LLC, Lowell, MA) with the gerbil head covered with the ColorDome E3 stimulator, customized by the manufacturer to deliver long-wavelength LED stimuli with a peak at 660 nm. Animals were adapted to ambient room light for at least 1 hr. Prior to ERG, animals were exposed for 5 minutes to a 513-nm ganzfeld background at 30 cd·s/m2. All ERG procedures were conducted on the same background. Human L-opsin activity was tested using stimulation with 660 nM LED flashes at varying intensities delivered at 1 Hz. Flicker ERG responses to 660 nm stimuli at 10 cd·s/m2 were recorded at 10 and 25 Hz. Responses to short (440 nm peak) and medium (513 nm peak) LED light flashes at 0.1 cd/m2 or 0.5 cd/m2 respectively, were recorded to evaluate whether the expression of human L-opsin from ADVM-062 affected normal function of cones in gerbil retina.

Immunohistochemistry. Gerbil and NHP eyes were fixed in 10% neutral buffered formalin (NBF) for 24 hours upon enucleation. Whole eyes were prepared for paraffin embedding using vacuum infiltration processing and placed into blocks. During gerbil eye processing, mid-sagittal sections through the visual streak were collected at 5-μm thickness. During NHP eye processing, transverse sections through the optic disc and central cornea were collected at 5-μm thickness and mounted on charged slides. Five serial slides were selected starting from the central fovea towards the superior parafovea at 25-μm or 40-μm increments. Slides were deparaffinized and rehydrated prior to antigen retrieval in citrate buffer. Immunofluorescent labeling was performed using a Dako LV-1 autostainer following tissue permeabilization and serum protein blocking. Antibodies and PNA (peanut agglutinin) used for detection of retinal markers are listed in Table S2.

TABLE S2

Antibodies for Immunofluorescence

| Antibody | Vendor | Working Concentration |
|---|---|---|
| Calbindin | Abcam (ab108404) | 1 μg/mL |
| Cone Arrestin | Milipore Sigma (AB15282) | 2 μg/mL |
| Peanut agglutinin PNA | Vector Laboratories (RL-1072-5) | 5 μg/mL |
| S-Opsin | Santa Cruz Biotech (SC-14363) | Diluted Stock: 1/500 uL |
| L/M Opsin | Santa Cruz Biotech (SC-22117) | 0.2 μg/mL |
| MYC-tag | Abcam (ab172) | 0.4 μg/mL |
| Rhodopsin (4D2) | Millipore-Sigma (MABN15) | 0.4 μg/mL |
| Long wavelength-sensitive opsin antibody | Biorbyt (orb182458) | 1 μg/mL |
| GFP | Abcam (ab13970) | 10 μg/mL |

Images were acquired with a Hamamatsu ORCA-Flash4.0 camera on a Zeiss Axio Observer.Z1 inverted microscope equipped with a 20× objective lens. Fluorescent images employed the additional use of the Zeiss Apotome optical sectioning system using structured illumination. Images were processed and analyzed using the Zeiss Zen Blue imaging and analysis software. NHP foveal cone cell quantifications were performed on stitched 20× enhanced resolution images. The foveal area was subdivided into regions, the fovea and parafovea. A 500-μm region centered over the foveal avascular zone (FAZ) was selected to represent foveal cone cell counts. Parafoveal cone cell counts were assessed by selecting a 550-μm region starting from the margins of the FAZ and extending out towards the temporal and nasal parafoveal periphery. In brief, the analysis of percentage of cones expressing human L-opsin-myc was performed using c-myc tag-specific monoclonal antibody 9E10, using 5-μm sections cut from formalin fixed paraffin-embedded (FFPE) ocular tissues. To evaluate expression in the fovea, serial sections were cut along the fovea-optic disc axis. After antigen retrieval, sections were stained for c-myc and the cone-specific marker, cone arrestin. Nuclei were identified using DAPI. Total cone number of human L-opsin-myc-positive cone outer segments were counted and normalized to total cone number, estimated as the number of nuclei in the outer nuclear layer of fovea known to consist entirely of cones based on cone arrestin staining (Ikeda et al, 2019). To evaluate expression of human L-opsin-myc in S-cones, myc immunostaining was colocalized with the S-opsin. Cell counting was performed by the treatment-masked investigator.

Statistical analysis. The effect of treatment on the ERG b-wave amplitudes in response to 600-nm stimuli provided with different intensities was evaluated using RM ANOVA with Sidak's multiple comparisons test. The amplitude of response to 660 nm stimuli in animals treated with different doses of ADVM-062 was compared with that in vehicle-treated animals and was evaluated using an ordinary one-way ANOVA with Dunnett's multiple comparisons test. The comparison of responses in vehicle- and ADVM-062-treated animals to 440, 513, and 660-nm stimuli was performed using an unpaired t-test. Amplitudes of the fundamental component of flicker ERG responses at 25 Hz in vehicle and ADVM-062-treated eyes were measured using Fast Fourier Transformation (FFT) and compared using an unpaired t-test.

Results

Figures 1, 7A:
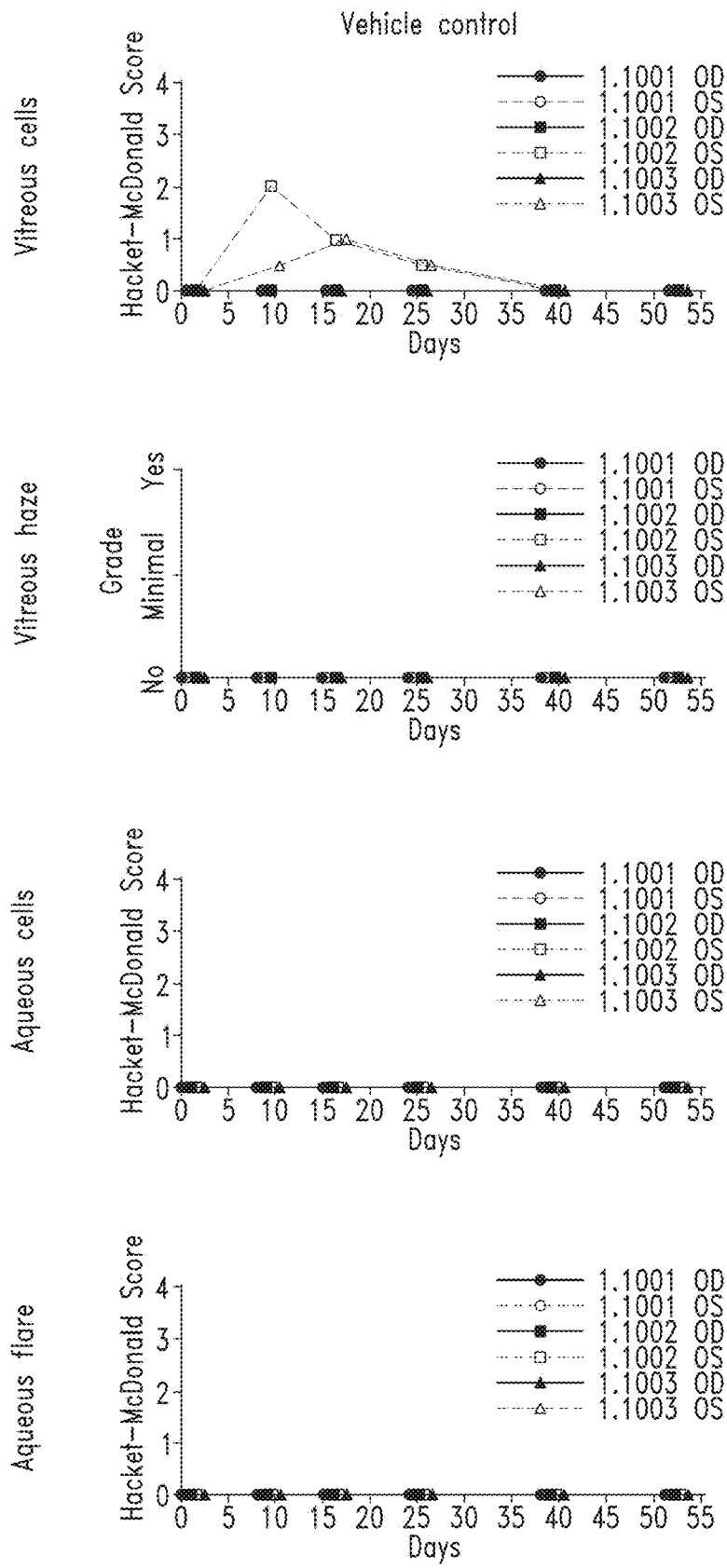
Figures 2, 7A:
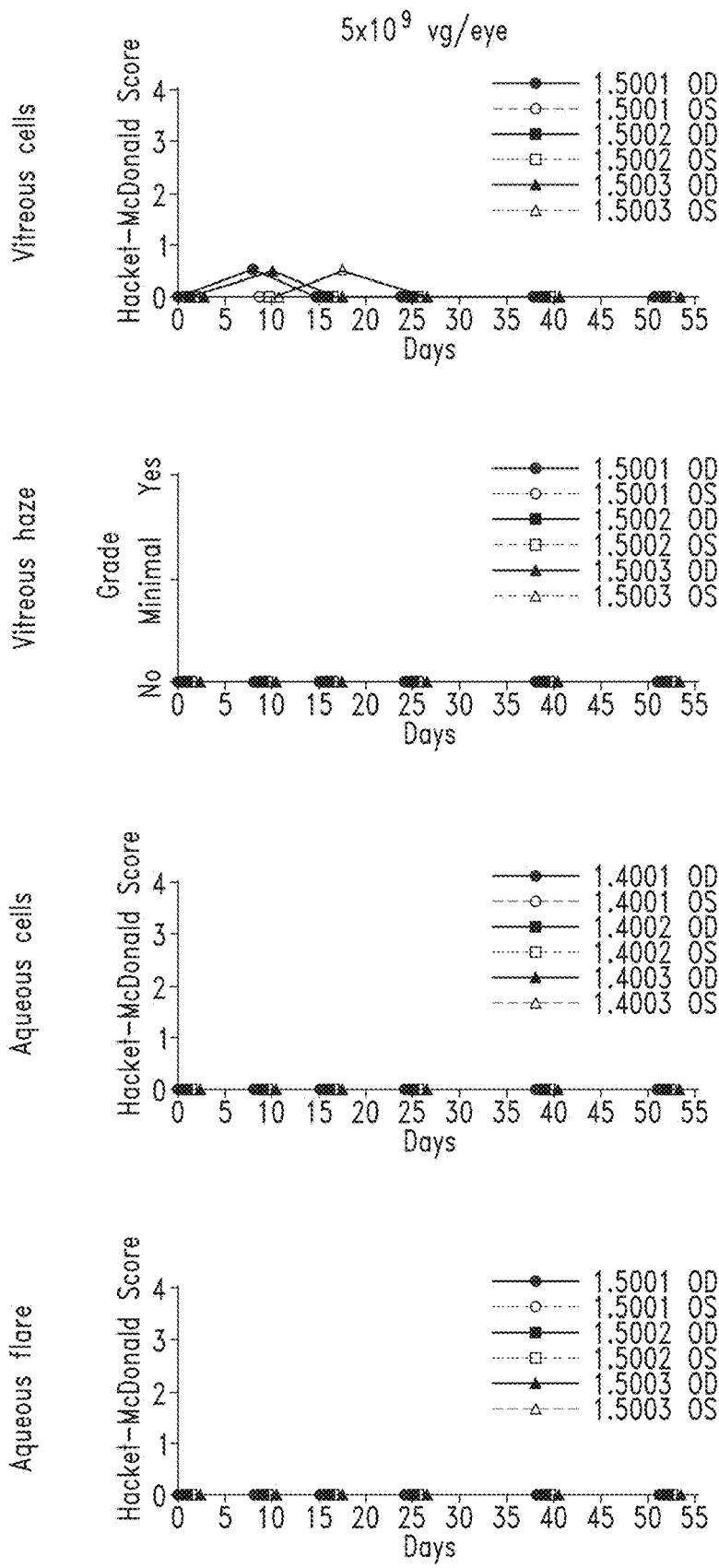

Vector Characterization. The cone specificity and efficiency of the AAV2.7m8 capsid combined with MNTC regulatory elements was initially characterized in African green monkeys using the surrogate vector, AAV2.7m8-MNTC-GFP, with regulatory elements identical to ADVM-062 but with an EGFP reporter as a transgene. An SLO (scanning laser ophthalmoscopy) study of the topology of GFP expression in eyes intravitreally (IVT) injected with AAV2.7m8-MNTC-GFP showed efficient transduction of the fovea and peripheral retina. Evaluation of the cellular specificity of GFP expression demonstrated robust and strictly cone-specific expression of GFP in the fovea and peripheral retina (FIG. 2).

Pharmacological Activity. In vivo functional activity of ADVM-062 was assessed in Mongolian gerbils, a rodent model suitable for testing cone-targeted therapies, as their cone-rich retinas (12-15% of gerbil photoreceptors are cones), consisting of short- (S; UV) and middle (M)-wavelength-sensitive opsins but lacking long-wavelength-sensitive L-opsin (Neitz 2001). Therefore, the native ability of the gerbil retina to respond photometrically to red light is very limited, thus allowing for the evaluation of ADVM-062 delivered human L-opsin functionality.

Figure 3A:
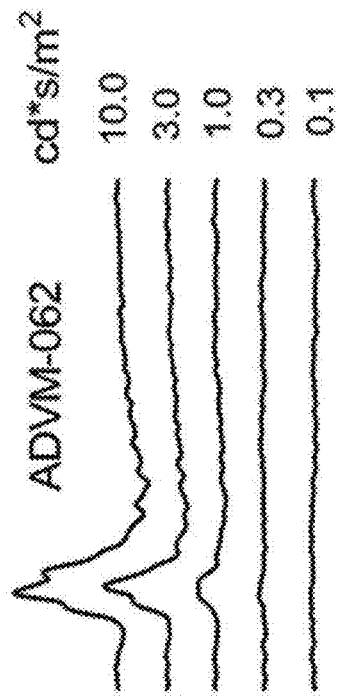
Figure 3B:
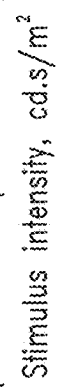
Figure 3C:
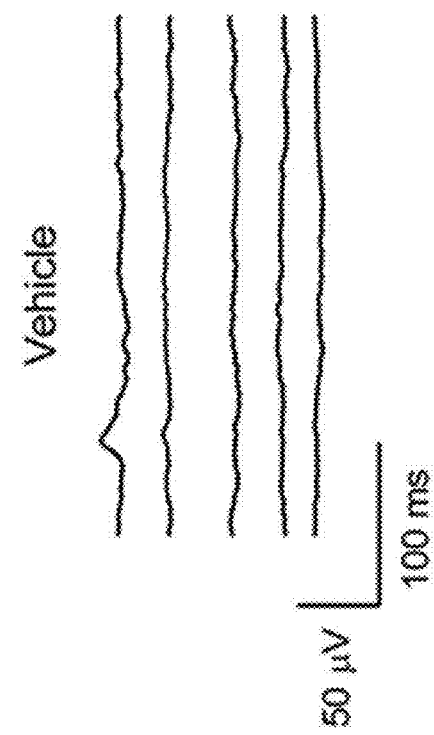
Figure 3D:
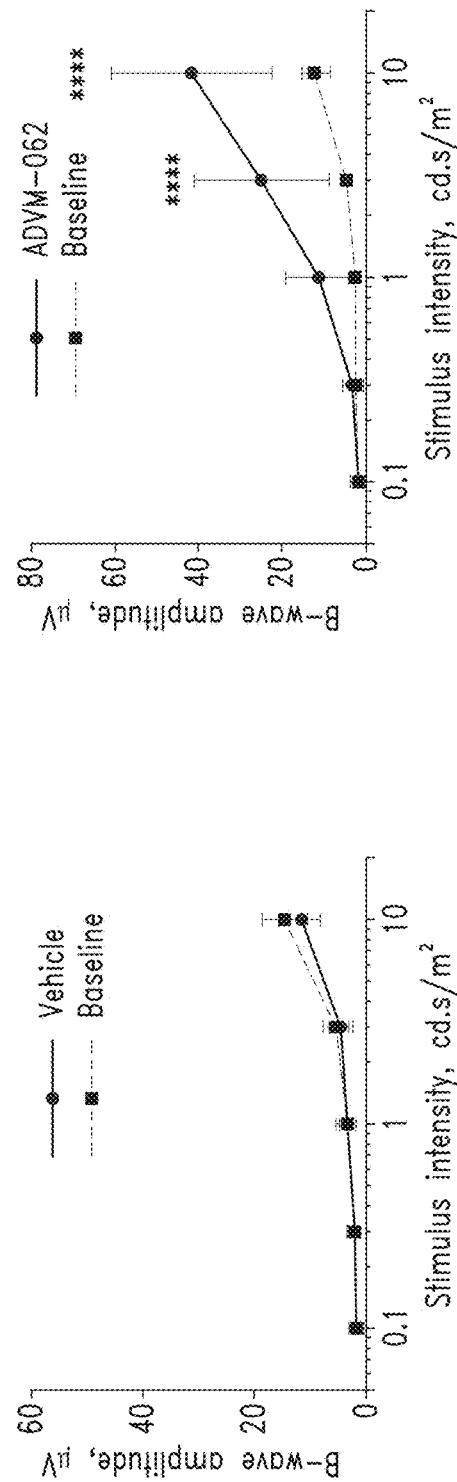
Figures 3, 7A:
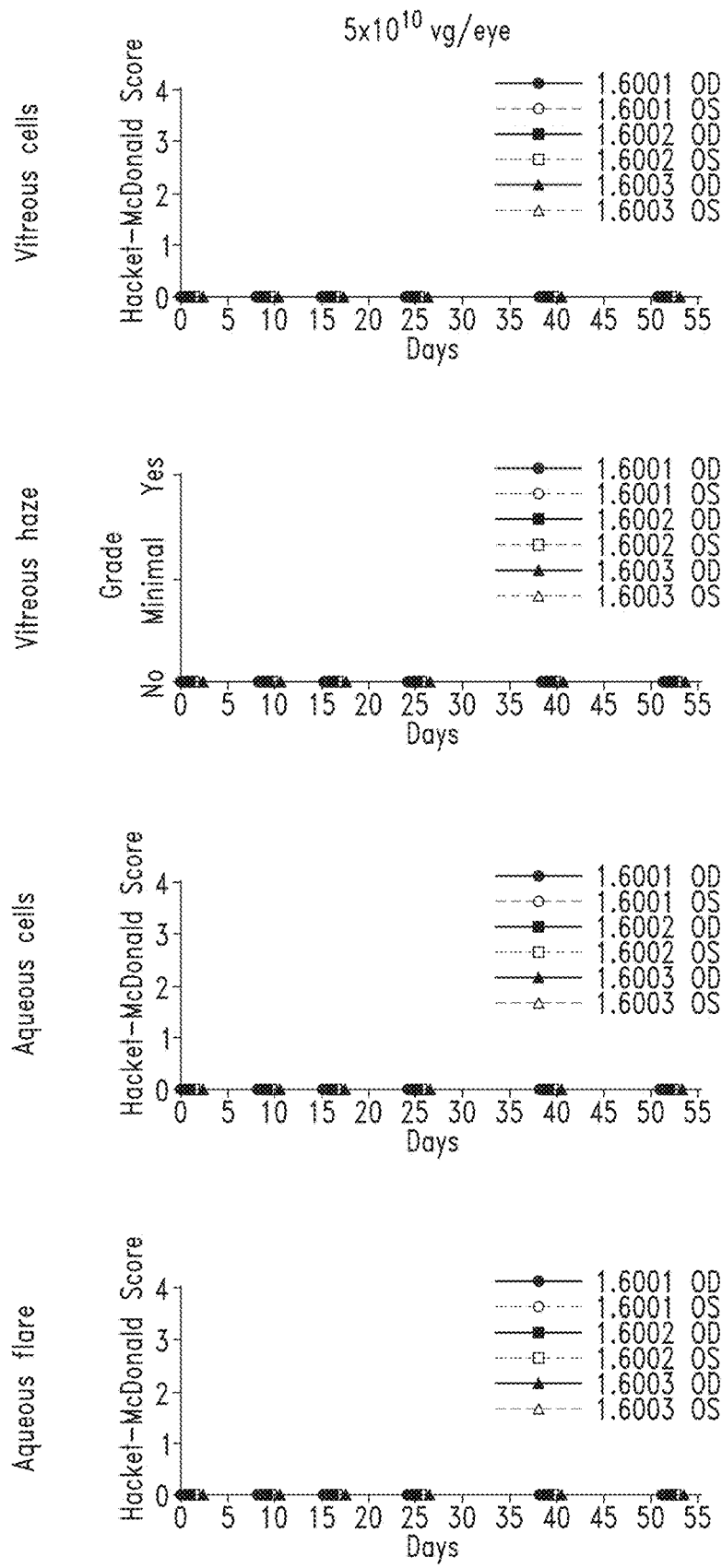
Figures 4, 7A:
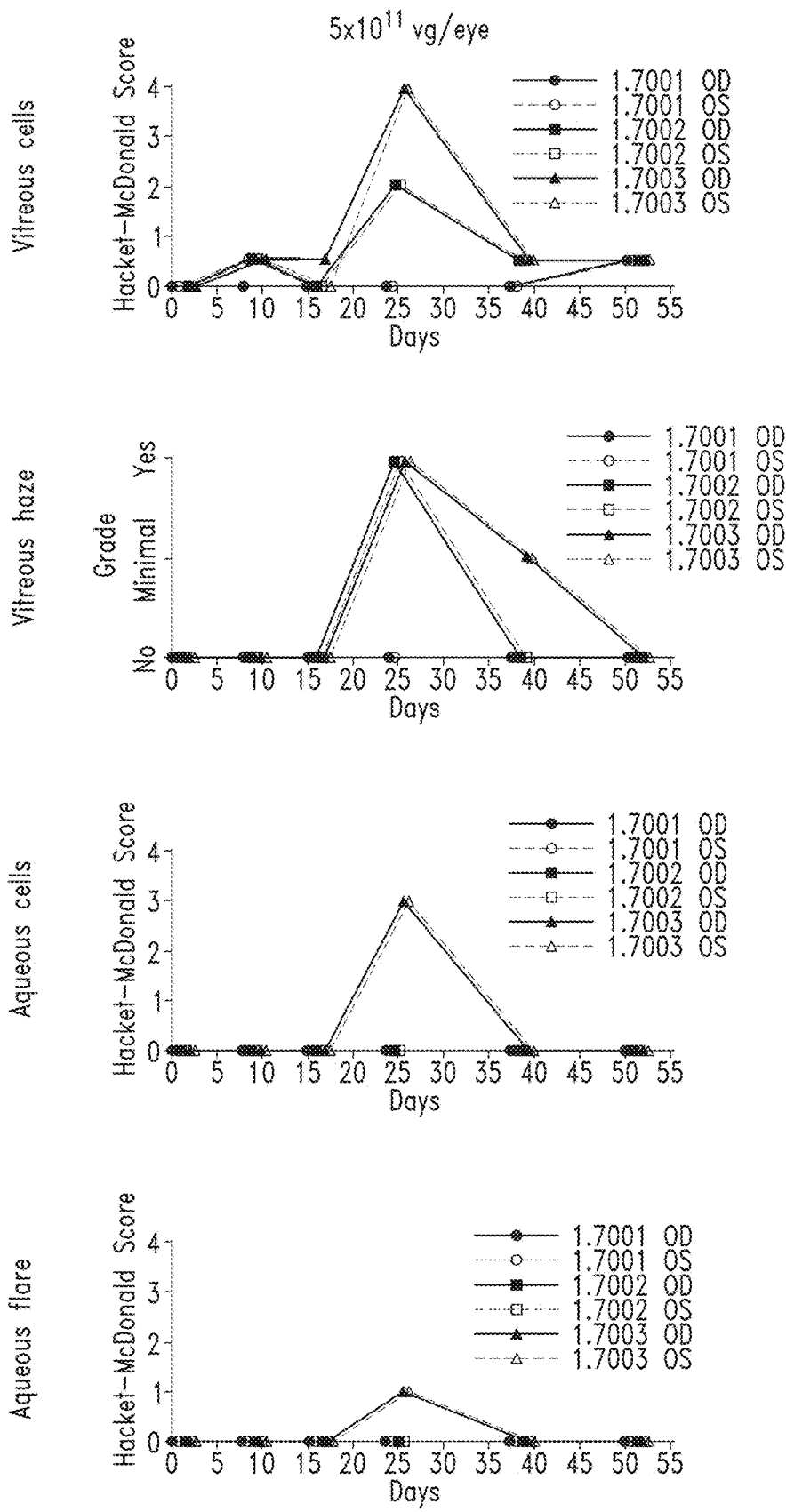

Functional expression of human L-opsin was evaluated using full-field color ERG (cERG) with light emitting diodes (LED) of different wavelengths, at different intensities and frequencies (FIG. 3). A ganzfeld green background illumination (513 nm, 30 cd·s/m2) was used to suppress rod activity and to reduce the sensitivity of cones expressing M-opsin to long-wavelength light. Vehicle-injected gerbil eyes adapted to medium wavelength light had low cERG responses to long-wavelength (660 nm) light flashes applied at intensities between 0.1 and 10 cd·s/m2 (FIG. 3A, 3C). A small increase observed at higher stimulus intensities (above 1 cd·s/m2) was likely mediated by gerbil M-opsin. Eyes treated with a single IVT injection of ADVM-062 demonstrated significantly increased retinal sensitivity to red light (FIG. 3B, 3D). Cone-isolating 25 Hz flicker cERG responses to 660-nm flashes were recorded to confirm the cone-specific nature of the ADVM-062-mediated sensitivity to red light. The significant increase of 25 Hz flicker cERG response to 660-nm light found in the ADVM-062-treated eyes was consistent with a response driven by cone cells (FIG. 3E, 3F). The de novo sensitivity to red light was detected as early as 3 weeks post-dose and remained stable out to the last data point collected at 26 weeks post-dose (FIG. 3G). Durability of the pharmacological activity of ADVM-062 was assessed in a separate study, in which gerbils injected with a single IVT injection of ADVM-062, showed retinal sensitivity to red light out to as long as 20 months (87 weeks) post-dose (FIG. 3H). Co-expression of the human L-opsin transgene in cells that express endogenous medium- and short-wavelength opsin proteins did not alter the response to short or medium wavelengths, as evidenced by the similarity in b-wave amplitudes among naïve, vehicle-treated, and ADVM-062-treated animals in response to 440-nm and 513-nm light stimuli (FIG. 3H).

Figure 3J:
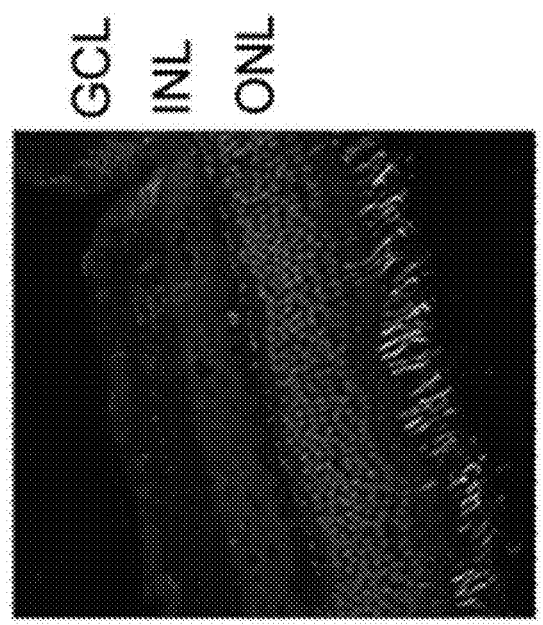
Figure 3I:
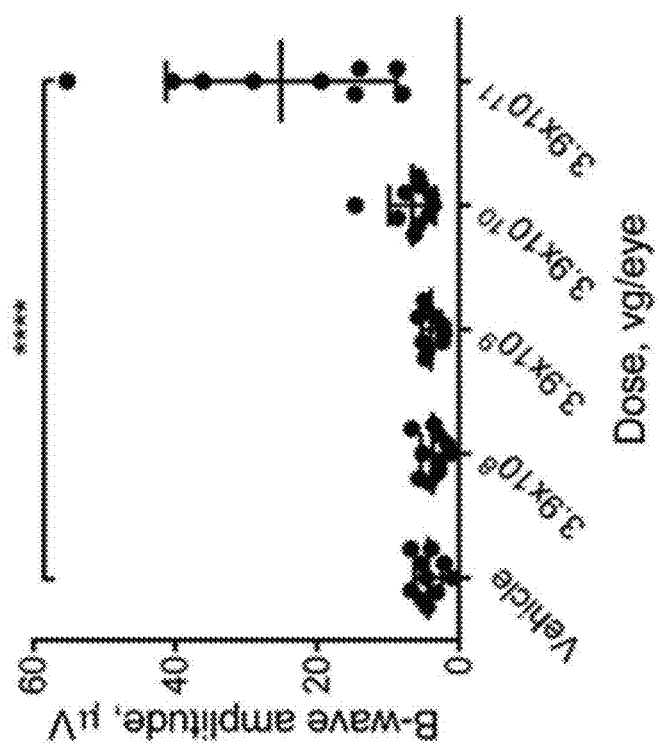

The effect of ADVM-062 was dose-dependent. Doses ranging from $3.9 \times 10^8$ to $3.9 \times 10^{11}$ vg/eye resulted in increased response over background starting at a dose of $3.9 \times 10^{10}$ vg/eye (17.94±1.54 µV in ADVM-062-treated vs 12.28±0.92 µV in vehicle-treated eyes; n=10 eyes per group) and reached statistical significance at $3.9 \times 10^{11}$ vg/eye (51.12±1.54 µV, $P<0.0001$) in ADVM-062 treated eyes (FIG. 3I). This steep dose-response might result from the need for vector to diffuse through the gerbil inner limiting membrane and several retinal cell layers to reach the cone photoreceptors. Since the AAV2.7m8 capsid tropism is not restricted to cones, it is possible for the vector particles to be trapped by the proximal retinal cells encountered early in the diffusion process, resulting in the need for higher doses to transduce distally located cone photoreceptors.

Figure 9:
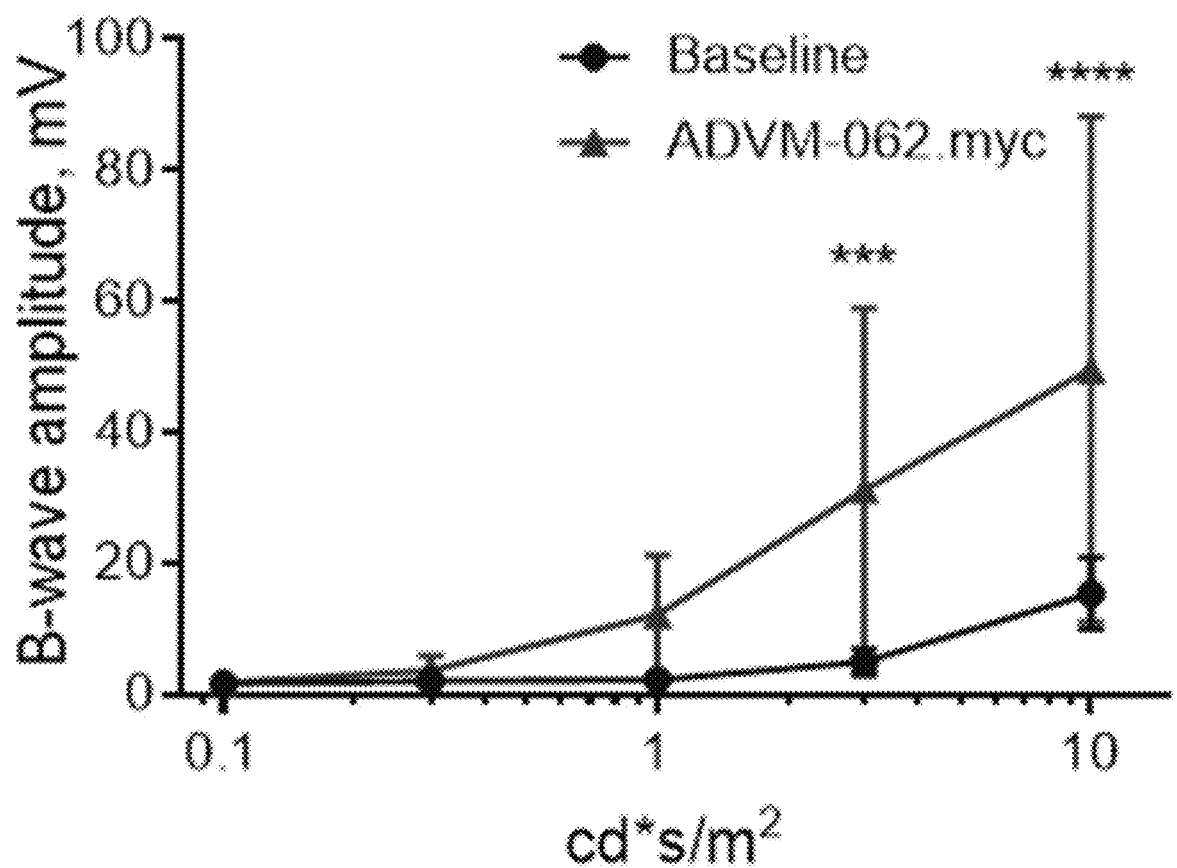
FIG. 9 shows that ADVM-062.myc sensitizes ERG responses in gerbil retina to 660 nm light stimuli, on rod and M-opsin suppressing background (*: P<0.001, **: P<0.0001 RM 2 way ANOVA with Sidak's multiple comparisons test). Means±SD shown.

MNTC-driven cone specific expression of human L-opsin was determined using an epitope-tagged ADVM-062 vector (ADVM-062.myc) engineered to express human L-opsin with a C-terminal myc tag. Use of the myc tag was necessary because there are no commercially available antibodies that differentiate between the human L opsin transgene and either rodent M opsin or non-human primate L or M opsins. It has been previously shown that myc-tagging of L-opsin results in expression of functional protein (Deng et al, 2018). Similarly, IVT ADVM-062.myc resulted in the expression of functional tagged L-opsin in the gerbil, as evidenced by the augmented ERG responses to 660-nm light stimuli (FIG. 9), corroborating functionality of the myc tagged human L-opsin transgene. Staining of retinal sections from ADVM-062.myc-dosed gerbil eyes showed cone-specific expression of human myc-tagged L-opsin where it was localized to cone photoreceptor outer segments, identified by PNA staining (FIG. 3J).

Dose-dependent expression of transgenic human L-opsin in the NHP retina. To establish dose-dependent efficacy and tolerability of IVT delivered ADVM-062 that could translate to doses to be used clinically, the vector was tested in NHPs (*Macaca fascicularis*). We conducted two dose-ranging studies using ADVM-062 and ADVM-062.myc that evaluated (i) safety at all doses delivered by IVT administration, (ii) dose-dependent expression of human L-opsin transgene in the retina, (iii) the dose-dependent protein localization in foveal cones, and (iv) percentage of transduced foveal cones. The latter measurement served as a metric for evaluating potential ADVM-062 clinical efficacy using the NHP retinal model. In one of the studies, vectors were administered as single IVT injections at three dose levels ($5 \times 10^9$, $5 \times 10^{10}$ and $5 \times 10^{11}$ vg/eye). A second study expanded the evaluation of doses at $3 \times 10^{10}$ and $5 \times 10^{10}$ vg/eye (see Table S1). Human dosages are calculated as a factor of two (2) relative to NHP dosages (Human dosage=NHP dosage×2).

The detection of activity of human L-opsin in retina of NHPs with trichromatic vision by ERG or using conventional biochemical or immunostaining methods is challenging due to the presence of endogenous L-opsin with similar spectrum of absorbance to that of human L-opsin, as well as a nearly identical protein and nucleotide sequence, (98% identity between human and NHP L/M opsins). Therefore, to assess transduction efficacy, we have qualified an LC-MS-MS-based method for quantitation of human L-opsin in whole retina lysates based on quantitation of a signature peptide unique to human L-opsin. In addition, we utilized the ADVM-062.myc vector strategy to evaluate localization of expression of transgenic human L-opsin and to measure percentage of human L-opsin positive cones in the NHP retina.

Figure 4:
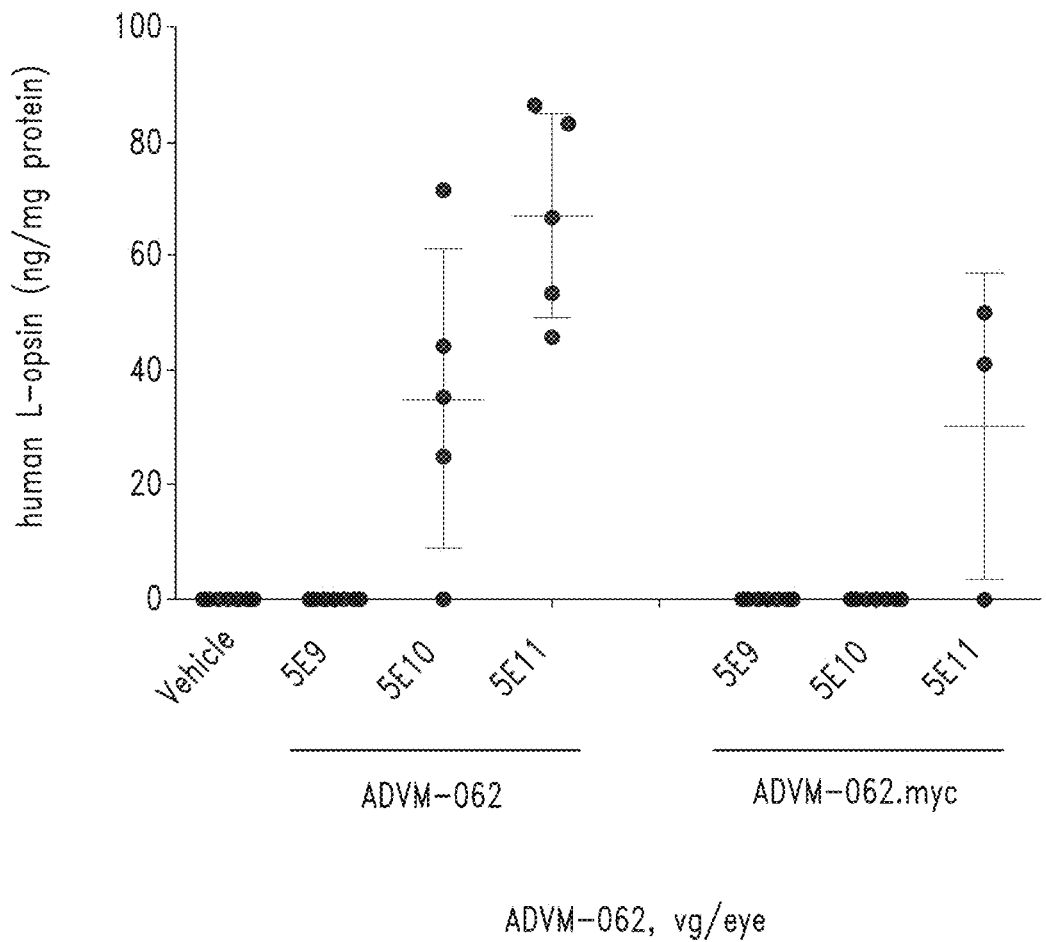
FIG. 4 shows the levels of human L-opsin protein as determined by LC-MS-MS in whole NHP retinal lysates from vehicle-treated (blue symbols), ADVM-062-treated (green symbols), and ADVM-062.myc-treated (red symbols) NHP eyes. Levels of human L-opsin are normalized to total protein in lysates. Means±SD are shown.

Using the LC-MS-MS method, we determined that the levels of human L-opsin were below the limit of quantitation in the eyes from the animals treated with $5 \times 10^9$ vg/eye of the vector. At doses of $5 \times 10^{10}$ and $5 \times 10^{11}$ vg/eye, a dose-dependent increase in the levels of human L-opsin was observed (FIG. 4). LC-MS-MS quantified levels of myc-tagged human L-opsin in retinal lysates from the ADVM-062.myc-treated animals were lower than the ones measured in the ADVM-062-treated eyes (FIG. 4). Nevertheless, the levels sufficed to detect human L-opsin-myc-positive cones by myc-tag-directed immunofluorescence and to quantify the efficacy of transduction based on the percentage of hhL-opsin-myc positive cells (FIGS. 5A-5H).

Figure 5A:
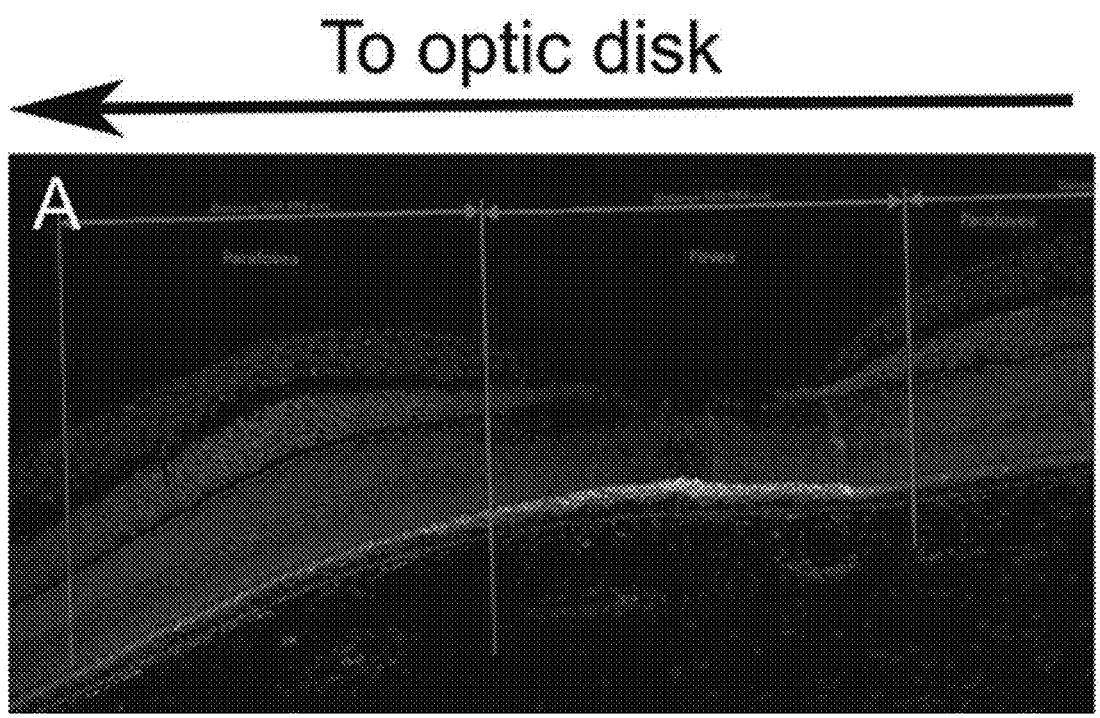
Figure 5B:
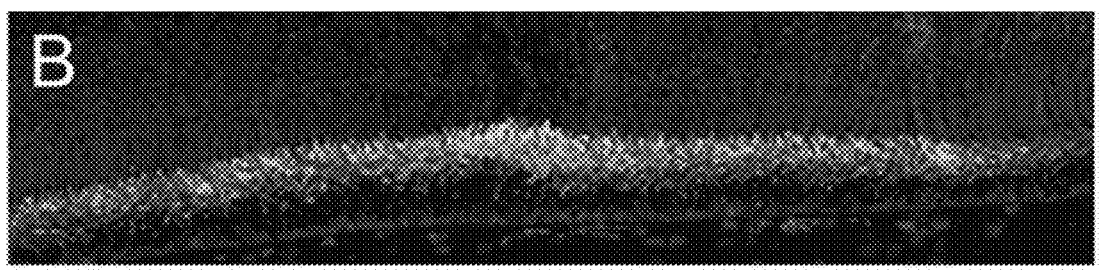
Figure 5C:
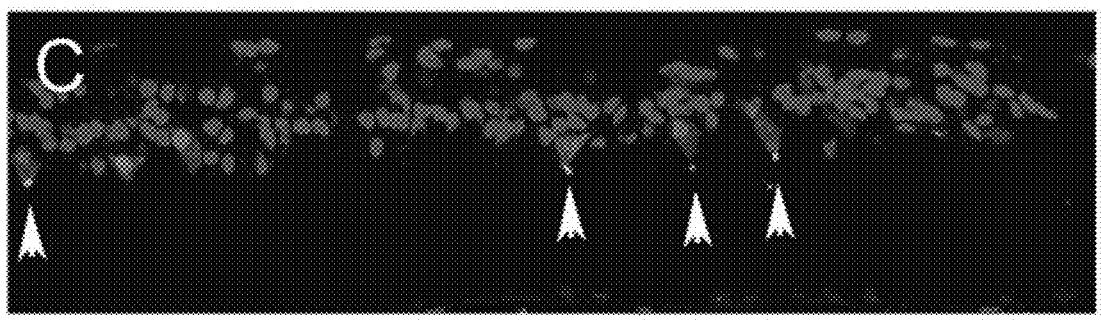
Figures 10A, 10B, 10C:
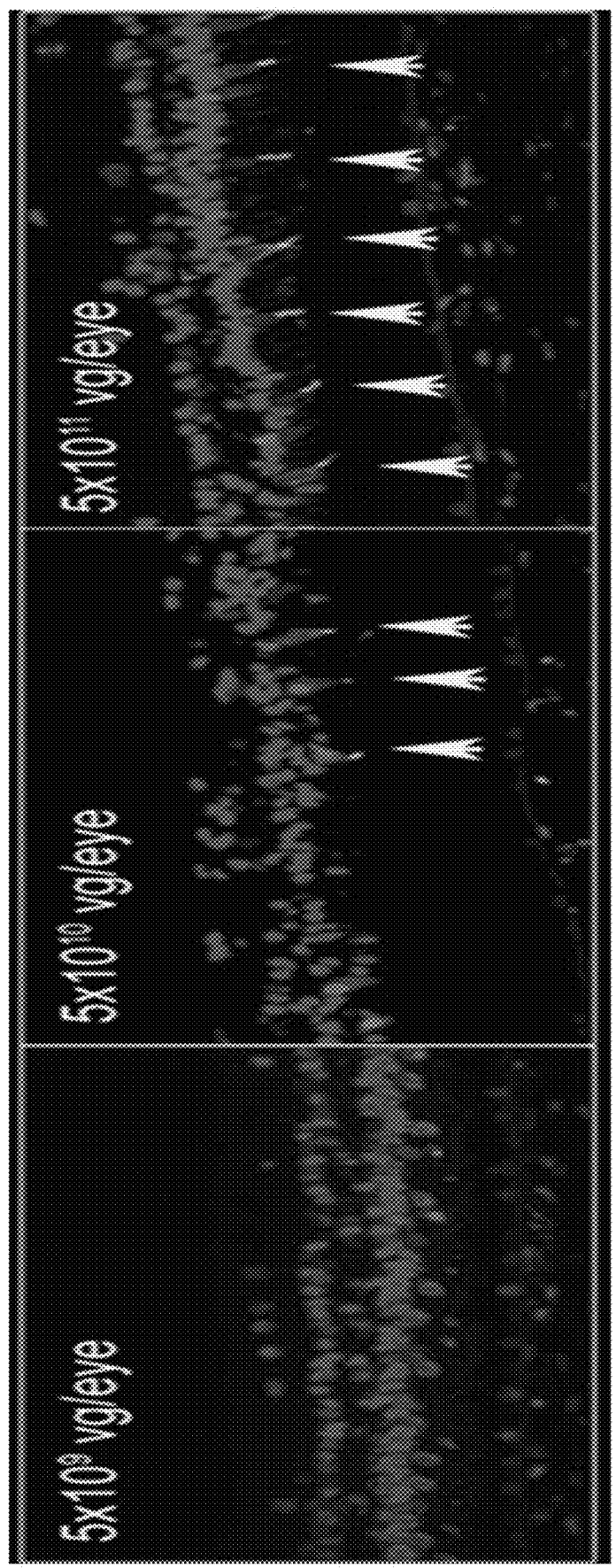
FIGS. 10A-10C show dose-dependent expression of hL-Opsin.myc in peripheral cones. ADVM-062-myc was IVT dosed at $5\times10^9$ vg/eye (Animal 21001) (A), $5\times10^{10}$ vg/eye (Animal 3002), (B) and $5\times10^{11}$ vg/eye (Animal 3003), (B). Blue: DAPI, nuclei. Red: cone arrestin, Green: hOPN1LW-myc (To add animal numbers for panels). Arrowheads: hL-opsin-myc—positive cones in peripheral retinas.

Immunostaining of the retina from the NHPs treated with ADVM-062.myc demonstrated dose-dependent human L-opsin.myc expression at all doses tested. ADVM-062.myc-mediated expression of myc-tagged human L-opsin was concentrated in the fovea, which contains densely packed cones responsible for high-acuity vision (FIGS. 5A-5C). Representative images of foveal (FIG. 5A, 5B) and peripheral (5C) retinal sections from an NHP dosed with ADVM-062.myc at $5 \times 10^{10}$ vg/eye, 8 weeks post-dose, stained with a myc-tag antibody and counterstained with the pan-cone marker cone arrestin are shown. Frequency of hL-opsin-myc positive cones was evaluated by counting of myc-positive cones identified by immunofluorescence in serial histological sections cut through the fovea avascular zone (FAZ) to the periphery. Frequencies measured in the 500-µm region centered over the FAZ showed that the lowest dose of ADVM-062.myc ($5 \times 10^9$ vg/eye) resulted in variable transduction of foveal cones ranging from 4.8% to 49.8% in individual animals, while ADVM-062.myc at doses of either $3 \times 10^{10}$, $5 \times 10^{10}$, or $5 \times 10^{11}$ vg/eye resulted in transduction of foveal cones between 17.7% and 85.3%. With increasing vector doses, expression extended outwards toward the periphery, with increasing percentage of hL-opsin-myc-positive cones in the parafovea (FIG. 5D) and periphery (FIGS. 10A-10C). No expression of human L-opsin.myc was found in any retinal cells other than the cones.

Figures 6A, 6B:
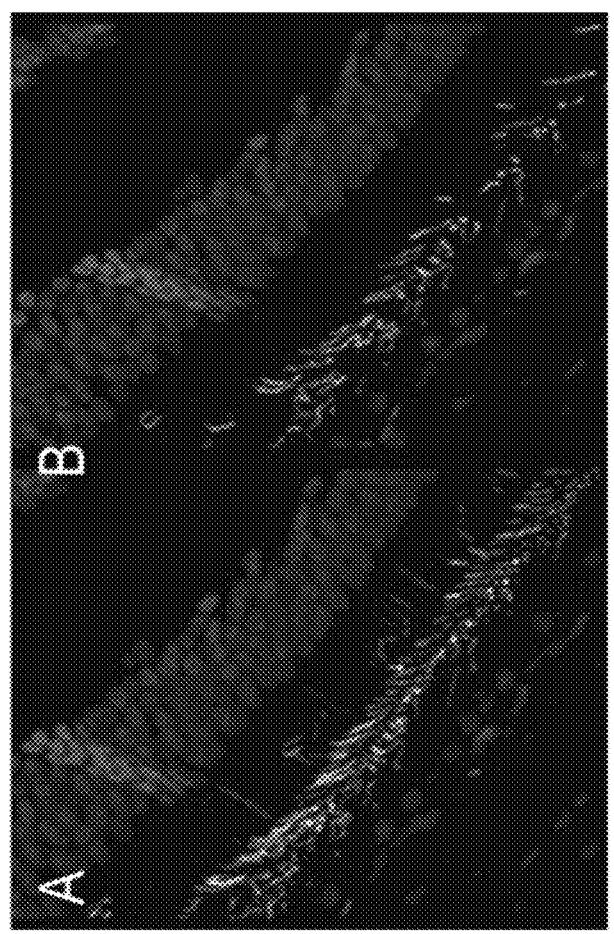
FIGS. 6A-6C show that ADVM-062.myc causes low frequency of expression of transgenic hL-opsin-myc in S-cones. (A) Colocalization of hL-opsin-myc (Green) with pan-cone marker arrestin (Red). (B) Colocalization of hL-opsin-myc (Green) with S-cone marker S-opsin (OPN1SW) (Purple). (C) Percentage of hL-opsin-myc positive S-cones counted in the 500-µm region of retina section cut from optic disk through FAZ. Means±SD are shown.
Figure 6C:
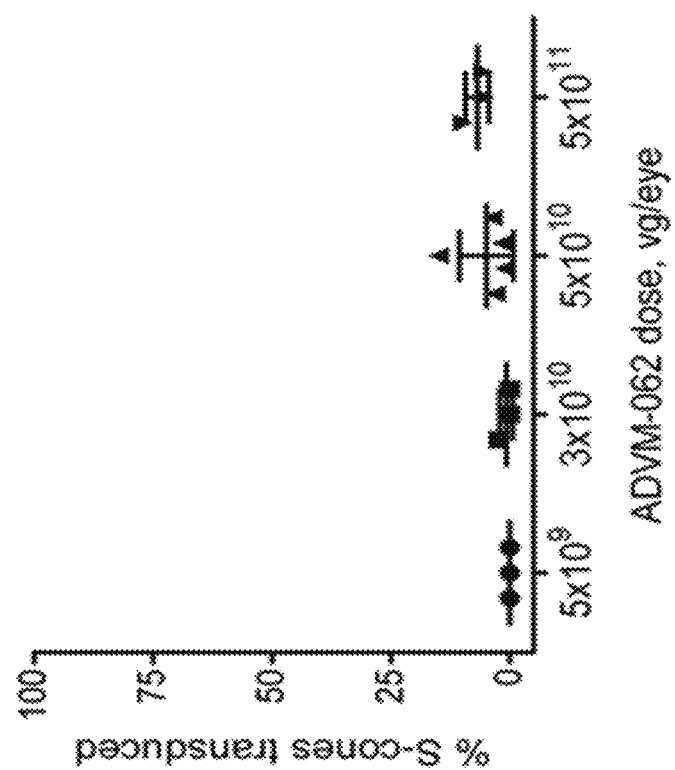

To determine whether ADVM-062 drives expression of transgenic human L-opsin in all cones or has a preference for M and L cones, we compared the percentage of S-cones positive for human L-opsin.myc to the percentage of human L-opsin.myc-positive cells among all cone types in NHPs using pan-cone cone arrestin as a marker. Co-staining for myc tag and S-opsin revealed that the frequency of the S-cones positive for the transgene was much lower than the frequency of the transgene-positive M- and L-cones, suggesting that the MNTC regulatory element preferentially drives transgene expression in M- and L-cones (FIGS. 6A-6C).

Figures 1, 7B:
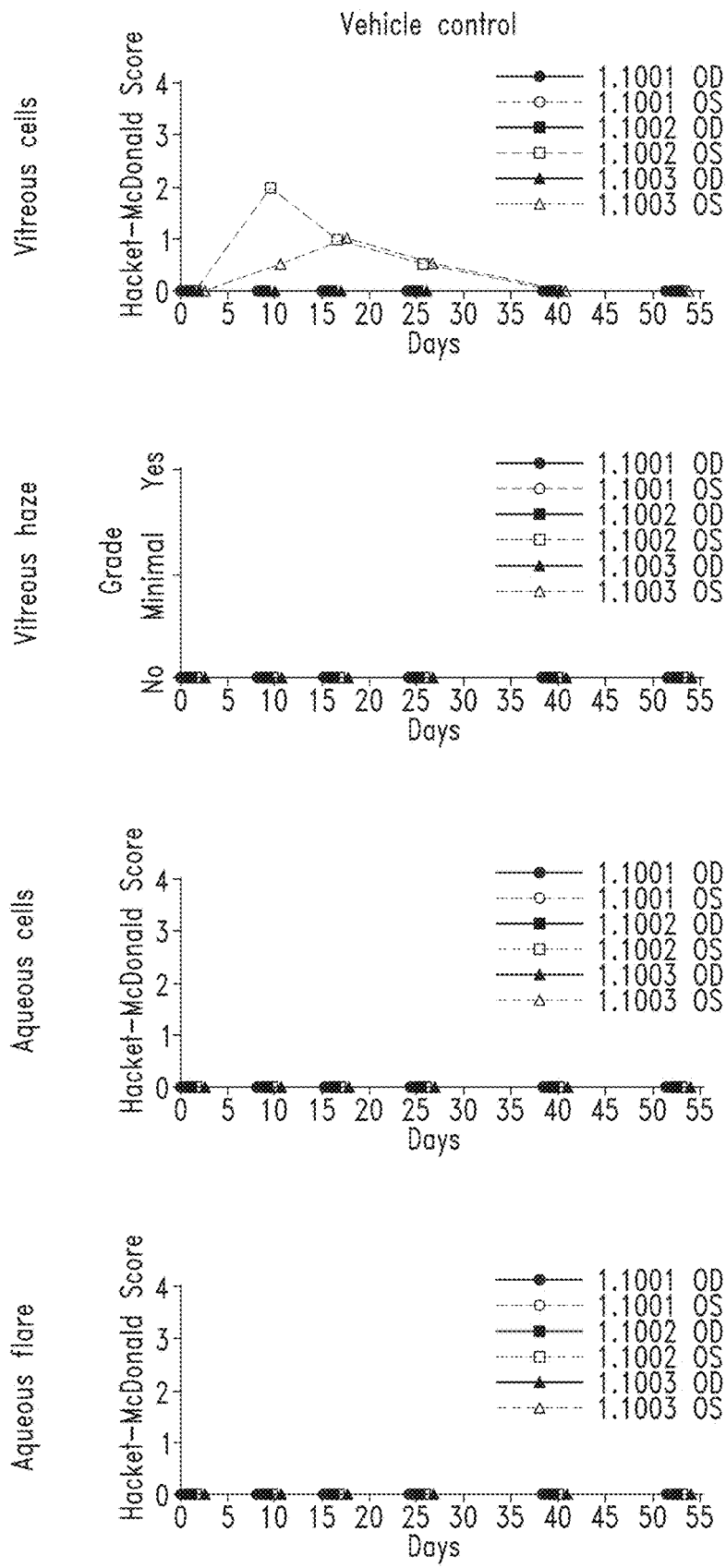
Figures 2, 7B:
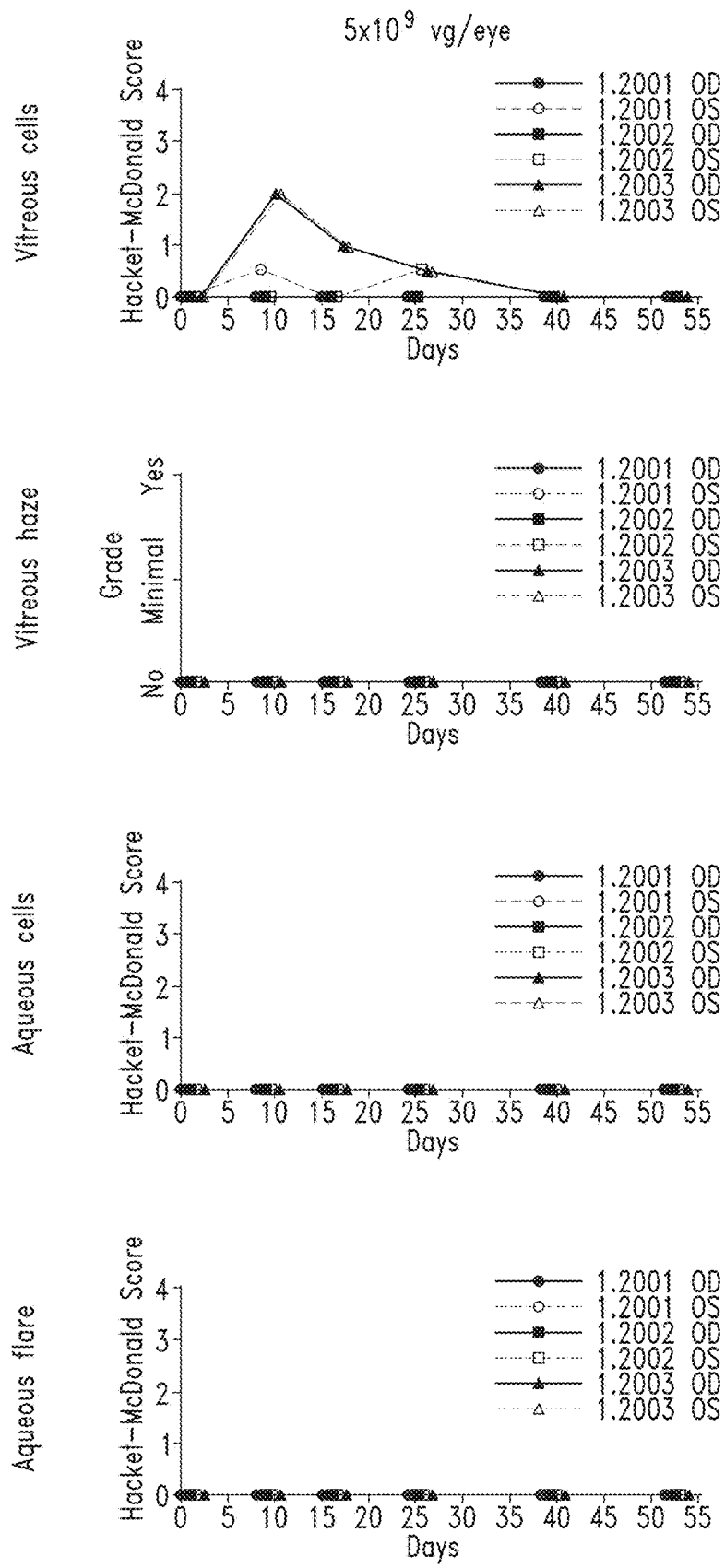
Figures 3, 7B:
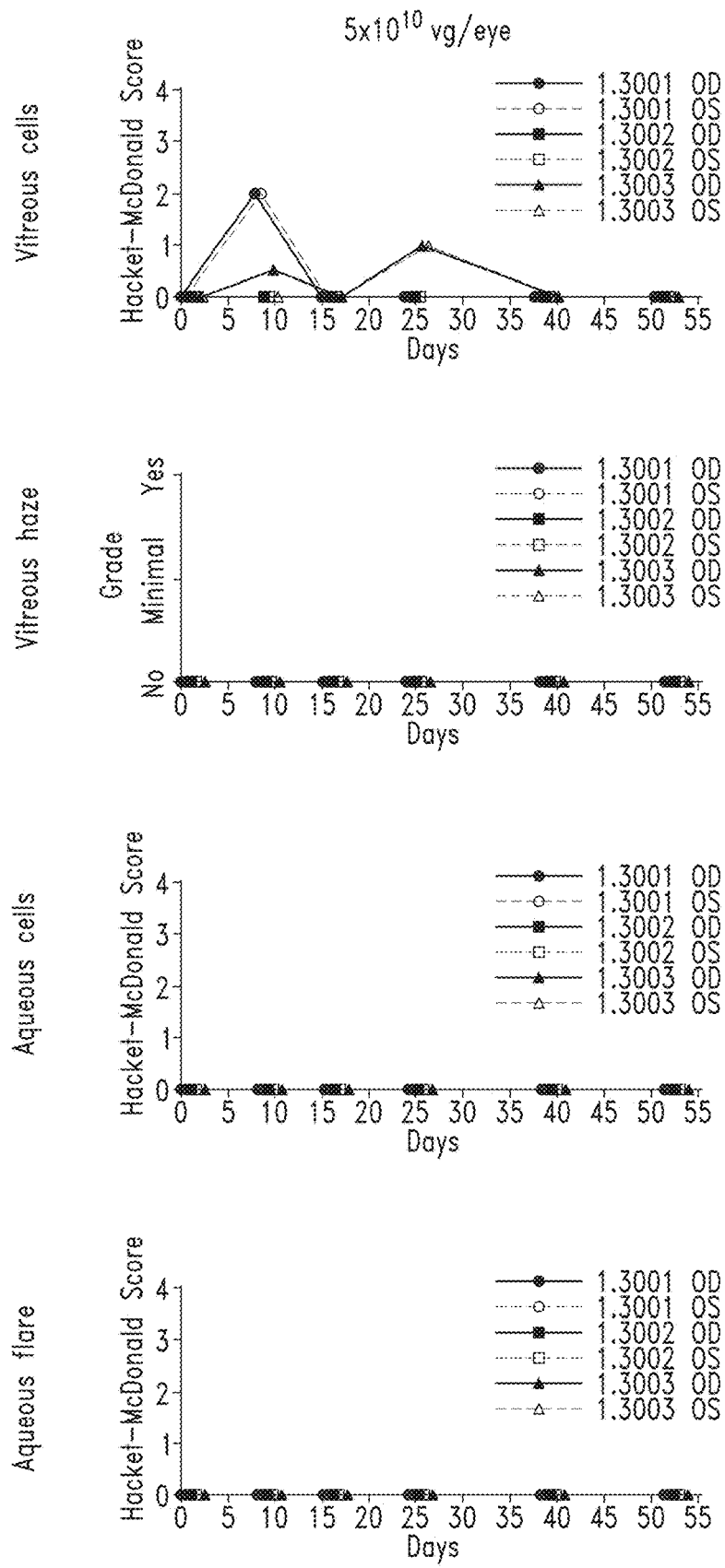
Figures 4, 7B:
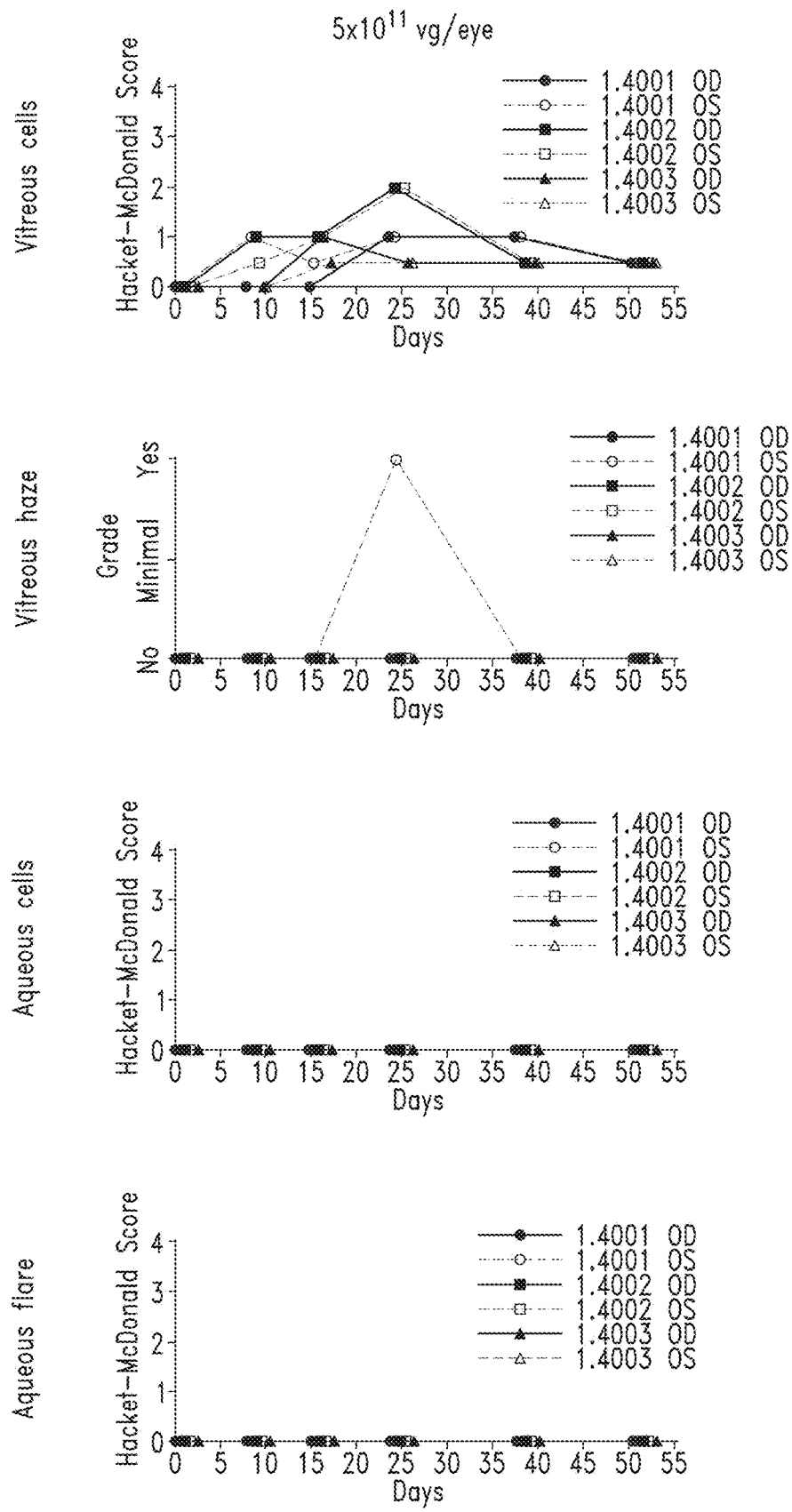
Figure 8A:
FIGS. 8A-8D show histological sections of retinas through fovea from NHPs dosed (A) with vehicle control (Animal 1101 OD) or IVT ADVM-062 at doses (B) $5\times10^9$ vg/eye (Animal 5001 OD), (C) $5\times10^{10}$ (Animal 6001 OD(C), or (D) $5\times10^{11}$ (Animal 7001 OD), stained with hematoxylin/eosin (H&E).
Figure 8B:
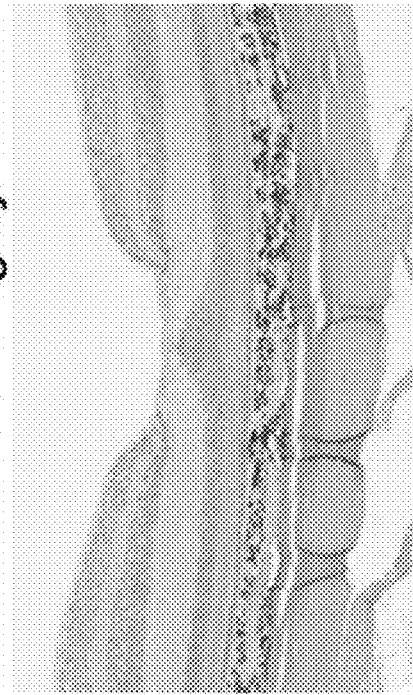
Figure 8C:
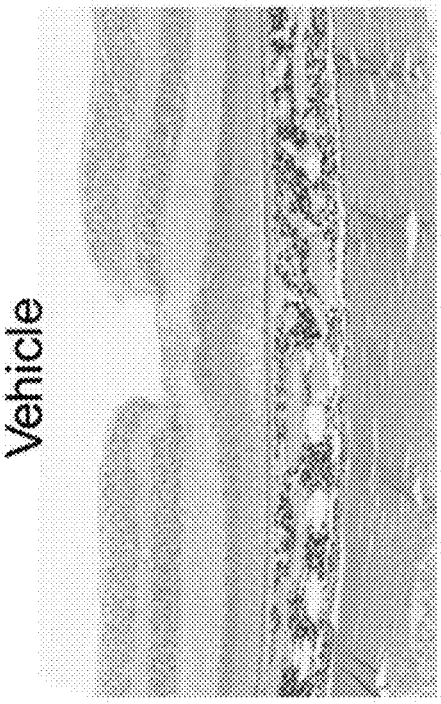
Figure 8D:
Figure 11A:
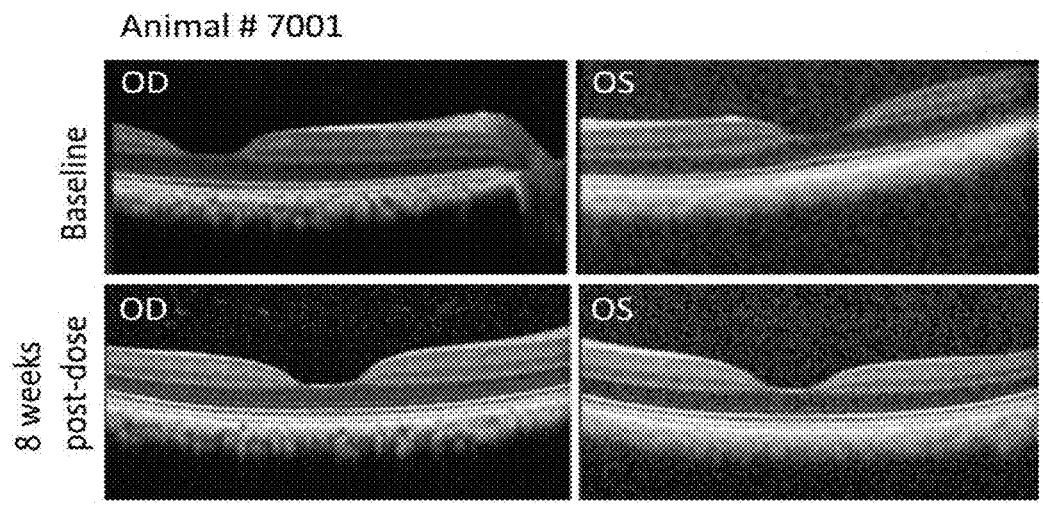
FIGS. 11A-11C show SD-OCT sections through fovea centralis of NHP at the baseline and 8 weeks post IVT dose of ADVM-062. Images of retinas of animals treated with ADVM-062 at the high dose of $5\times10^{11}$ vg/eye are shown.
Figure 11B:
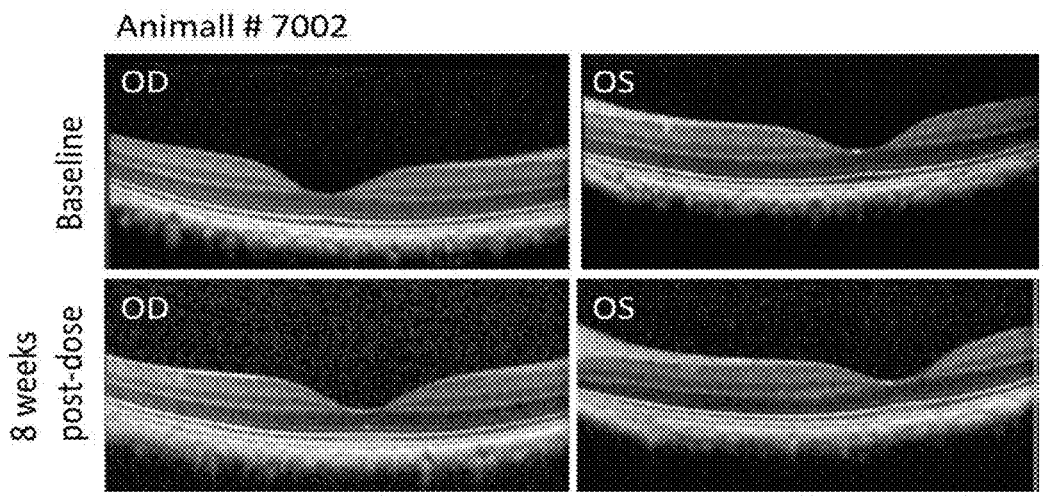
Figure 11C:
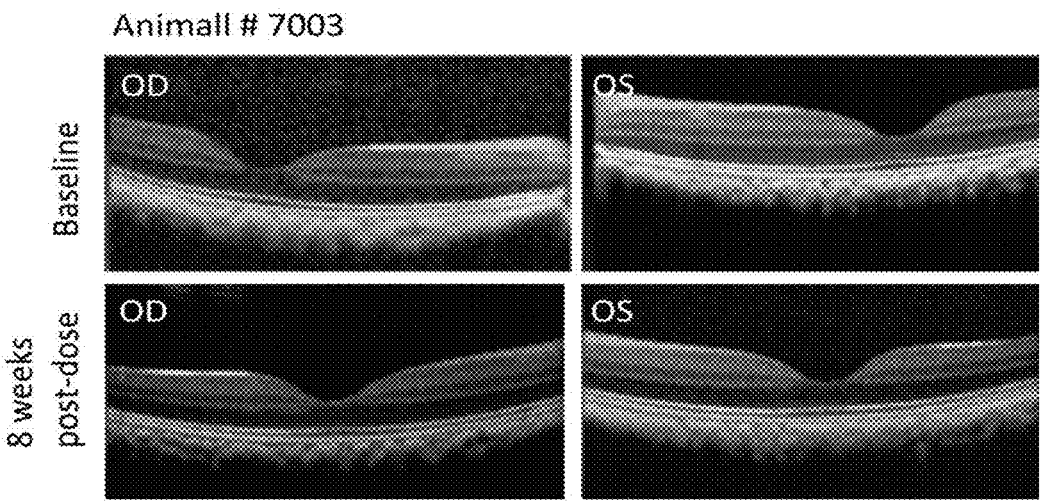

Safety and tolerability in non-human primates. Ocular tolerability and safety in NHPs was assessed for 2 months post ADVM-062 IVT injection. IVT administration of ADVM-062 or ADVM-062.myc in doses ranging from $5 \times 10^9$ to $5 \times 10^{11}$ vg/eye was well tolerated. In eyes dosed with the highest dose of $5 \times 10^{11}$ vg/eye of ADVM-062 resulted in transient Grade 4+ vitreous cell infiltrates and vitreous haze, and Grade 3+ aqueous infiltrates in some of the eyes at Day 24. However, this inflammatory response self-resolved without intervention by Day 38, and only trace numbers of vitreous cells and pigmented cells were noted by the end of the study (Day 56). The animals treated with ADVM-062 at $5 \times 10^9$ and $5 \times 10^{10}$ vg/eye demonstrated no test article-related ocular events beyond those observed in the vehicle group (FIGS. 7A-1 to 7A-4, 7B-1 to 7B-4). No anti-inflammatory treatment was warranted at any time during the study. The NHP groups treated with ADVM-062.myc showed similar dose-dependency of inflammation (FIGS. 7B-1 to 7B-4). Importantly, no changes in retinal anatomy were observed, as evaluated by optical coherent tomography (OCT) at any dose of vectors (FIGS. 11A-11C).

Figure 12A:
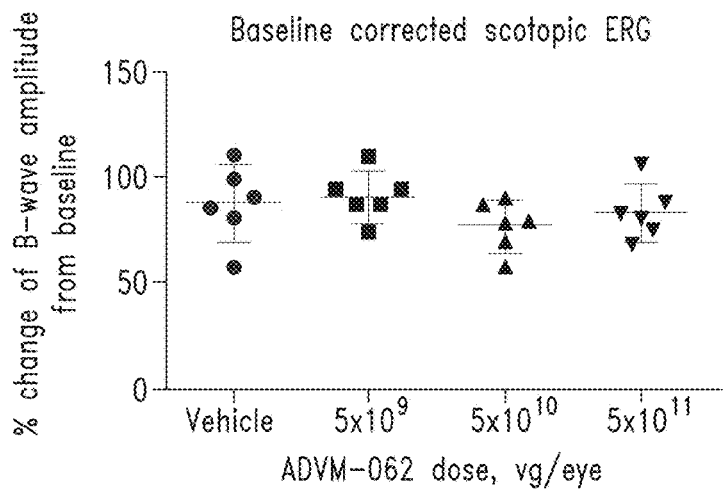
FIGS. 12A-12C show dark adapted (scotopic) (A), light adapted (photopic) (B), B-wave ERG, and flicker (C) amplitudes in NHPs dosed with IVT injected vehicle and ADVM-062, measured at Day 53 and normalized to responses recorded at the baseline before dose administration. Shown are scotopic responses to −8 dB white single flash, photopic responses to 0 dB single white flash, and flicker response to 0 dB 30.3 Hz flicker. No statistically significant difference was found between vehicle dosed eyes and any ADVM-062 dose group. (Ordinary one-way ANOVA with Dunnett's multiple comparisons test). Means±SD.
Figure 12B:
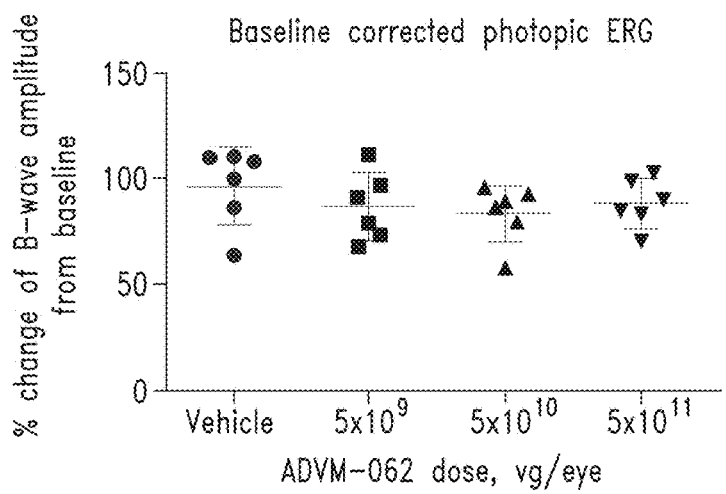
Figure 12C:
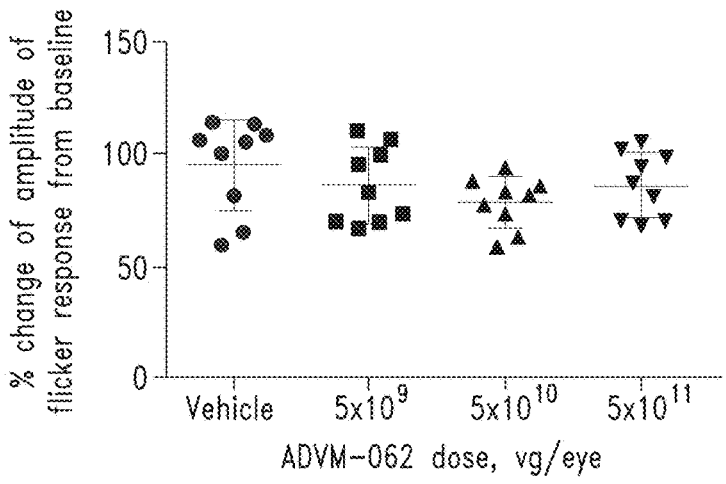

In agreement with the in-life assessments, hematoxylin/eosin (H&E) staining of the eye sections from select eyes from animals (one per dose group) dosed with vehicle or ADVM-062 at $5 \times 10^9$ or $5 \times 10^{10}$ vg/eye did not reveal any histological abnormalities (FIGS. 8A-8D). At the highest ADVM-062 dose of $5 \times 10^{11}$ vg/eye, minimal perivascular mononuclear cell infiltrates within the retina and anterior uvea were observed. This observation likely was associated with the trace inflammatory response observed at this dose at the end of the study. In agreement with the observed normal anatomy, full field scotopic, photopic, and flicker electroretinograms (ERG) did not identify any retinal functional abnormalities (FIGS. 12A-12C).

Discussion

A gene therapy approach to deliver sustained levels of a functional copy of L-opsin can improve BCM symptoms in patients affected by this debilitating, inherited retinal cone dystrophy. ADVM-062 mediated expression of functional human L opsin in the foveal region can improve central vision and increase visual acuity in BCM patients, while the expression of human L-opsin in the outer retina cones provides additional benefit, since peripheral cones were shown to play a role in the perception and processing of color and motion information out to the far periphery of the visual field. ADVM-062 is a gene therapy product specifically designed to deliver a functional copy of the OPN1LW gene via AAV2.7m8 vector to the foveal cones of patients suffering from BCM via a single in-office intravitreal injection From the safety perspective, ADVM-062 was designed to mediate expression of human L opsin exclusively in the cone photoreceptors, sparing other retinal neurons. Using AAV2.7m8-MNTC-GFP delivered IVT to the NHP eye, we have demonstrated that the MNTC regulatory elements that employ the human opsin LCR and a minimal M-opsin promoter used in ADVM-062 drive gene expression in a cone-specific manner.

Since the pharmacological activity of ADVM-062 could not be tested in trichromatic NHPs, we used Mongolian gerbils, a rodent species with a cone-rich retina that express only short (S/UV) and middle (M) wavelength sensitive opsins, as a suitable model to establish the functionality of ADVM-062-mediated human L-opsin (see Govardovskii 1991; Mauck 2008). Gerbils very limited innate ability to respond to long wavelength (red) light was significantly augmented by IVT-injected ADVM-062. ERG responses to 660-nm light using 25 Hz flicker were used to confirm the cone-specific nature of this sensitization. A robust ADVM-062-mediated response to red light was detected over 1.5 years after a single IVT dose of ADVM-062, the longest observation time in this study. Further, immunofluorescence studies conducted on retinas of animals treated with ADVM-062.myc confirmed that human L-opsin expression was localized to outer segments of cone photoreceptor cells. These results provide strong support for the proposal that IVT administration of ADVM-062 is effective in generating sustained functional expression of human L-opsin in cone photoreceptors.

However, the significant differences in the ocular anatomy between the primate and rodent retina pose a barrier for the extrapolation of a human dose from those evaluated in the rodent studies. To propose pharmacologically relevant clinical doses of ADVM-062 and to potentially establish safety margins for patients, ADVM-062 was tested in NHPs (*Macaca fascicularis*), a species whose overall retinal structure, including the presence of a fovea, closely resembles that of humans (Picaud 2019). Importantly, cone cells in the fovea are the primary targets of gene therapies aiming to treat inherited retinal diseases that affect cone photoreceptor function and survival (Khabou 2018).

Measuring expression, subcellular localization, and pharmacological activity of human L-opsin on the background of trichromatic NHP retina is challenging, due to an inability to differentiate and quantitate human L-opsin from the endogenous, functionally similar, NHP opsin that shares 98% sequence identity with human protein. To overcome these constrains, two strategies were applied: an LC-MS-MS method was developed that can measure levels of human L opsin in the background of the NHP retina, and an AAV2.7m8 vector was generated that carries the expression cassette for human L-opsin with the same regulatory elements as ADVM-062 but with an addition of C-terminal myc tag. The combination of these two approaches allowed us to measure the levels of transgene expressed in the NHP tissues and to determine localization and percentage of cone transduction. With the confirmation of the functionality of ADVM-062-expressed human L-opsin in the gerbil studies, the expression data from the NHP studies together with the observed safety and tolerability provide a translation of the findings to clinical doses.

LC-MS-MS was used to quantify the dose-dependent human L-opsin protein expression of IVT-delivered ADVM-062 in NHPs in retinal lysates, confirming the activity of ADVM-062 in NHPs. ADVM-062.myc was utilized to allow the detection and localization of human L-opsin in NHPs. Using this approach, levels of hL-opsin-myc were sufficient to allow detection of transduced cones in the NHP retina, thus enabling evaluation of a dose-effect of ADVM-062 by quantifying transduction of foveal cones at the cellular level as a measure of the pharmacological activity of ADVM-062.

The effect of density of functional foveal cones on visual function could be inferred from the clinical studies in the patients with retinal degenerative diseases with a residual number of surviving cones, or studies in the individuals with X-linked dichromacy, who have various number of functional cones, as well as neurophysiological studies in healthy individuals. For example, in Stargardt's disease, an autosomal recessive macular dystrophy, it was estimated that significant changes in visual acuity result only upon the loss of approximately 90% of the cone photoreceptors (Geller et al., 1992; Geller and Sieving 1993). Adaptive optics scanning laser ophthalmoscopy studies involving patients with several different retinal degenerative diseases that measured relationships between reduced cone density and visual acuity found that visual acuity in patients was weakly affected by cone loss until cone densities were 52%-62% (Ratnam IOVS, 2013) or 40%-50% below normal average (Foote, IOVS 2018), respectively.

In the study of Seipe et al (Seipe et al, 1994, Vis. Res), photoreceptor losses were modeled in healthy subjects by blanking randomly selected pixels. The study predicted that patients with a cone loss of 50% or more would be able to maintain 20/20 acuity, and 96% random loss of photoreceptors would result in visual acuity at 20/60. Additionally, information about the cone density sufficient to support foveal vision can be obtained from the studies of humans with X-linked red-green color vision deficit. It has been shown that the relative number of L and M cones (L:M ratio) varies greatly across individuals (Carroll 2002, Hofer 2005, Patterson 2016), and inactivation of one opsin gene (L or M) results in a variable degree of disruption of the foveal cone mosaic, likely due to variability in the L/M cone ratio. Studies of the relationship of foveal cone density with visual acuity in human dichromats demonstrated that differences in cone density were not apparent functionally (Patterson 2016). Interestingly, a patient in that study with the very low cone peak density of 18,927 cones/mm2 had normal visual acuity, comparable to another subject with normal trichromatic vision, and a density of 195,030 cones/mm2. This value was also significantly lower than the average peak cone density in the foveal area of 164,000±24 000 cones/mm2, (Wells-Gray, 2016) as determined by ASLO. These data indicate that restoration of function of ~10-17% of foveal cones is sufficient achieve clinical benefit in BCM patients.

We evaluated the percentage of foveal cones that express transgenic human L-opsin in the NHP retina as a relevant metric for ADVM-062 activity that can be used to establish the efficacious dose range for ADVM-062 in NHPs to guide selection of human doses (Human Dosage—NHP dosage× 2).

The use of ADVM-062.myc confirmed cone-specific expression in the NHP retina at all doses tested and established a preference for the transduction of L- and M-cones, known to be affected in BCM, over S-cones. This preference for L/M cones could be beneficial to BCM patients, whose vision is limited to rod cells and S-cone cells, which account for only 5% of the total cones in the human retina. The low probability of co-expression of L-opsin in S-cones together with naturally expressed S-opsin would reduce any hypothetical risk of expansion of spectral sensitivity of S-cones toward long-wavelength light due to co-expression of two opsins resulting in different absorbance spectra in the same cells.

The exploration of the doses yielding efficient cone transduction, revealed that at low dose of vector ($5\times10^9$ vg/eye), transduction was achieved, from very few transgene positive cones detected in a section cut through fovea center (4.8%) to a half of foveal cones transduced (49.8%). The doses of $3\times10^{10}$ vg/eye and above resulted in a clinically meaningful transduction ranging from 17.7% to 85.29%. At the lower dose range ($5\times10^9$-$3\times10^{10}$ vg/eye), human L-opsin expression was localized to the foveal cones, but extended outwards towards the periphery with increasing percentages of hL-opsin-myc-positive cones in the parafovea and peripheral retina with increasing doses ($5\times10^{10}$ and $5\times10^{11}$ vg/eye). This dose-dependent expansion of expression toward the periphery may reflect the thickness profile of the inner limiting membrane in the NHP retina, the major barrier for IVT-delivered AAV vectors in reaching the neural retina cells (Halfter 2014, in J. Sebag (ed) Vitreous: in Health and Disease. 2012). The lowest dose of vector ($5\times10^9$ vg/eye) resulted in variable transduction of foveal cones ranging from 4.8% to 49.8%, while the doses at $3\times10^{10}$ vg/eye and above resulted in clinically meaningful transduction of foveal cones ranging from 17.7% to 85.3%.

Overall, dose-dependence of retinal transduction as evaluated by the percentage of hL-opsin-myc-positive cones in the fovea and parafovea had the same trend as the dose-dependent expression of transgenic human hL-opsin protein in the retina measured by LC-MS-MS. Indeed, dose-dependent transduction of peripheral cones contributed to the levels of hL-opsin protein in total retina lysates quantitated by LC-MS-MS. This is supported by the increased number of transduced peripheral cones detected at higher doses of ADVM-062.myc, as detected by myc-immunofluorescence.

ADVM-062 was well tolerated, with no adverse events observed at dose levels of $5\times10^9$ and $5\times10^{10}$ vg/eye, while self-resolving ocular inflammation was observed at $5\times10^{11}$ vg/eye. This indicates that ADVM-062 displays a favorable risk-benefit ratio, consistent with safe dosing at potentially clinically meaningful levels. In conclusion, the studies described herein demonstrated ADVM-062, designed as an intravitreal gene therapy to treat BCM, can deliver clinically meaningful levels of foveal cone transduction and subsequent L-opsin expression at safe doses.

Example 2

GLP-Compliant Toxicology and Biodistribution Study of ADVM-062 (AAV.7m8-L-Opsin) as Single Intravitreal (IVT) Administration for Blue Cone Monochromacy (BCM)

To assess the tolerability of ADVM-062, an IND-enabling GLP-toxicology study was performed to assess IVT ADVM-062 administration in non-human primates (NHP) (~2 years old males), at $5\times10^{10}$ vg/eye, $1\times10^{11}$ vg/eye, and $3\times10^{11}$ vg/eye, to both eyes (n=3/group). Measuring the expression, subcellular localization, and function of hL-opsin on the background of the trichromatic NHP retina is challenging, due to the presence of endogenous L- and M-opsins, which are highly homologous to hL-opsin. Thus, doses were selected based on a non-GLP study with ADVM-062.myc surrogate, a vector similar to ADVM-062 engineered to express hL-opsin with a C-terminal myc tag for enumeration of transduced fovea cones, which suggested that IVT ADVM-062 similar doses may effectively transduce sufficient numbers of foveal cones to potentially achieve clinical efficacy (see Example 1).

Single bilateral intravitreal injection of ADVM-062 was administered to male cynomolgus monkeys at $5\times10^{10}$, $1\times10^{11}$, or $3\times10^{11}$ viral genomes (vg)/eye (Table S3).

TABLE S3

| Group No. | Test Material | Dose Level (vg/eye) | Dose Volume (mL/eye) | Dose Concentration (vg/mL) | No. of Male Animals [a, b] |
|---|---|---|---|---|---|
| 1 | Control (vehicle) | 0 | 0.05 | 0 | 2 |

TABLE S3-continued

| Group No. | Test Material | Dose Level (vg/eye) | Dose Volume (mL/eye) | Dose Concentration (vg/mL) | No. of Male Animals [a, b] |
|---|---|---|---|---|---|
| 2 | ADVM-062 | 5E10 | 0.05 | 1E12[c] | 3 |
| 3 | ADVM-062 | 1E11 | 0.05 | 2E12[c] | 3 |
| 4 | ADVM-062 | 3E11 | 0.05 | 6E12[c] | 3 |

No. = Number;

vg = viral genomes

[a] Each animal dosed on Day 1 by bilateral intravitreal injection.

[b] Animals will be euthanized on Day 98.

[c] Nominal dose concentration.

Ophthalmic examinations (slit-lamp biomicroscopy and indirect ophthalmoscopy) and tonometry were performed throughout the course of the study (Table S4). Electroretinography and optical coherence tomography were performed once pretreatment, and during Weeks 4 and 12 (Table S4).

TABLE S4

| Parameter | Population (s) a | Frequency |
|---|---|---|
| Mortality | All study animals | At least once daily (afternoon) beginning by Week −2 |
| Cage Side Observations | All study animals | At least once daily in the morning beginning by Day −7 |
| Individual Body Weights | All study animals | Weekly; from at least Day −7 |
| Food Consumption | All study animals | Once daily; from at least Day −7 |
| Ophthalmic Examinations and Tonometry | All study animals | Once pretreatment; Days 3, 8, 15, and 21, and during Weeks 4, 6, 8, 10, 12, and 14. |
| Electroretinograms | All study animals | Once pretreatment and during Weeks 4 and 12 |
| Optical Coherence Tomography (OCT) | All study animals | Once pretreatment and during Weeks 4 and 12 |
| Electrocardiology (ECG) Exams | All study animals | Once pretreatment, Day 2, and during Week 13 |

Eye examination procedures. The animals were lightly sedated with ketamine prior to this procedure. Prior to ophthalmic examination, a mydriatic (1% tropicamide) was instilled in each eye. Slit-lamp biomicroscopy was performed to examine the anterior segment of the eye, lens, and anterior vitreous. Included in the examination of the anterior segment were the lids and conjunctiva, cornea and tear film, anterior chamber, iris, and pupil. The anterior segment was scored using the modified Hackett-McDonald scale. Indirect ophthalmoscopy was performed to evaluate the vitreous, retina (including the retinal vessels), optic disc, and choroid. Exams were performed at the baseline (9 days prior to the dose on day 1), and on days 3, 8, 15, 21, and during weeks 4, 6, 8, 10, 12, and 14 post-dose.

Intraocular pressure measurements. Intraocular pressure was measured in the eyes of sedated animals using a TONOVET® tonometer on the default setting under laboratory light conditions, at approximately the same time of day as when the IVT injections were performed. Tonometry was performed at the baseline (9 days prior to the dose on day 1), and on days 3, 8, 15, 21, and during weeks 4, 6, 8, 10, 12, and 14 post-dose.

Quantitative PCR (qPCR) assay for biodistribution (BD). The assay components are listed in Table S5 below.

TABLE S5

| Component | Name | Sequence |
|---|---|---|
| Fwd Primer | ADVM062-Set5-3SV FWD | 5'-CTCTCCTTTCCCCCTCCTTC-3' (SEQ ID NO: 4) |
| Rev Primer | ADVM062-Set5-3SV REV | 5'-GCATTCTAGTTGTGGTTTGTCCA-3' (SEQ ID NO: 5) |
| Probe | ADVM062-Set5-PRO | 5'-6FAM-TGCCAAAACCAACAGACATGA-MGB 3' (SEQ ID NO: 6) |

DNA extraction from solid tissues was performed according to Avance Biosciences' SOP LO GEN 13 (for most solid tissues) and SOP LO GEN 30 (for fatty tissues). Briefly, tissue was homogenized using a TissueLyser II (Qiagen) and followed by proteinase K digestion and DNA extraction. DNA extraction from blood was performed according to Avance Biosciences' SOP LO GEN 31 using a Maxwell 16 Blood DNA Purification Kit on a Maxwell 16 Instrument. Genomic DNA was quantified by PicoGreen fluorescence. A Standard Curve dilution series was included on each ADVM062-Set5-3SV qPCR assay reaction plate. The standard curve consisted of a dilution series of the linearized control plasmid pADV676-CMV-L-Opsin 3'UTR-sv40PA DNA. For qPCR plate setup, 2.5 mL of each standard curve dilution was combined with 2.5 mL naïve cynomolgus monkey liver genomic DNA at 200 ng/mL and that was used as the reaction template in triplicate wells. NHP liver genomic DNA has been selected as a matrix due the high yield and quality of its preparation.

After each qPCR run, the data were analyzed using the QuantStudio 12k Flex Sequence Detection System software and the $C_T$ values of each reaction were determined with a cycle threshold set in the exponential phase of amplification. Raw data contains quantity of the target in each reaction well was reported by the QuantStudio 12k Flex Sequence Detection System software and was exported to an Excel spreadsheet. The copies of target DNA were calculated by averaging the quantities detected in the first three wells for each sample. The $C_T$ value of the fourth well containing a spike for each sample was examined and the reactions for that sample would be considered to have significant PCR inhibition if the $C_T$ value is more than spike control $C_T+1$. Samples found to have PCR inhibition or have a detected quantity more than STD1 (5.0E+06) were diluted and retested via qPCR.

The average of the ADVM-062 vector copies detected in triplicate reactions was used to calculate the vector copies per microgram (µg) DNA tested. The numbers of ADVM-062 vector copies detected, if equal or above the LOQ (25 copies/reaction), were reported. Samples with a quantity of ADVM-062 vector detected below LOQ were reported as <LOQ.

ADVM-062 was well-tolerated throughout the course of the 3-month GLP study with no adverse clinical signs observed. There was one early euthanasia due to incidental aspiration of ingesta during a procedure and had no ADVM-062-related macroscopic or microscopic findings.

Figures 1, 13:
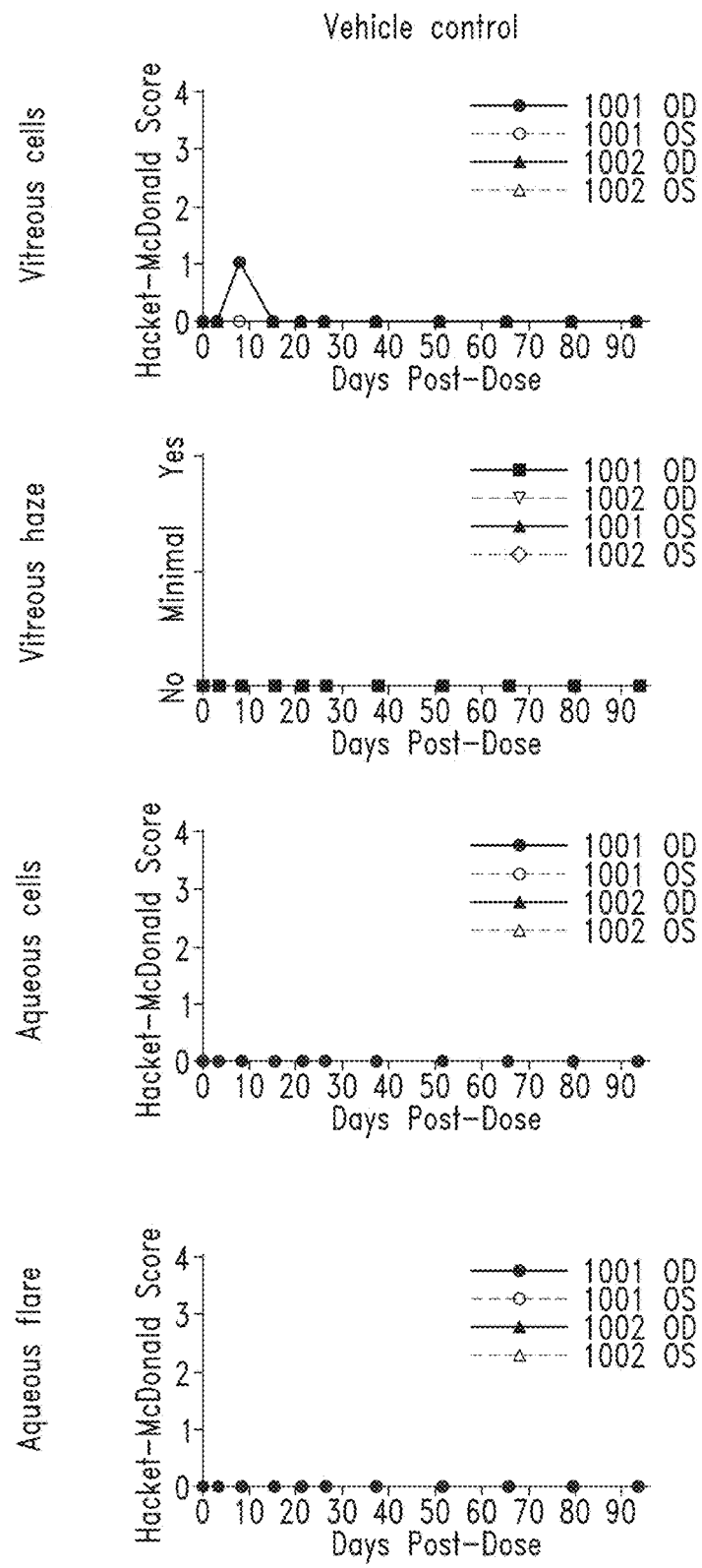
Figures 2, 13:
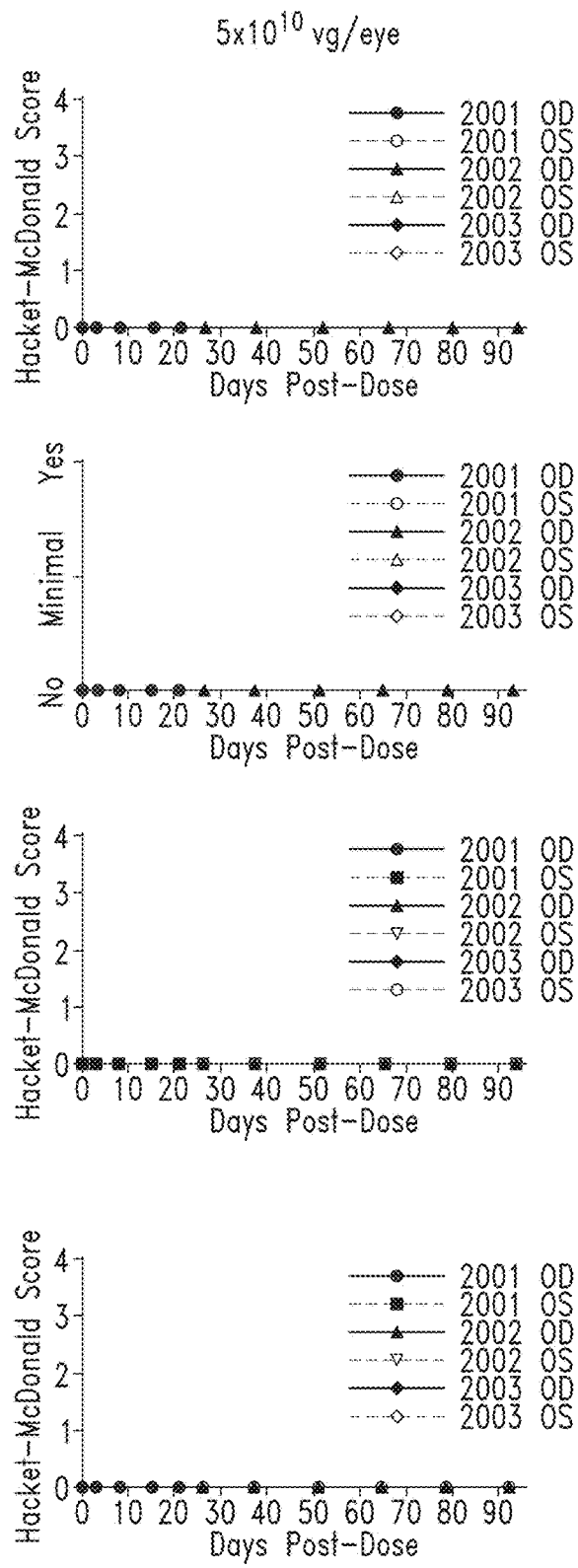
Figures 3, 13:
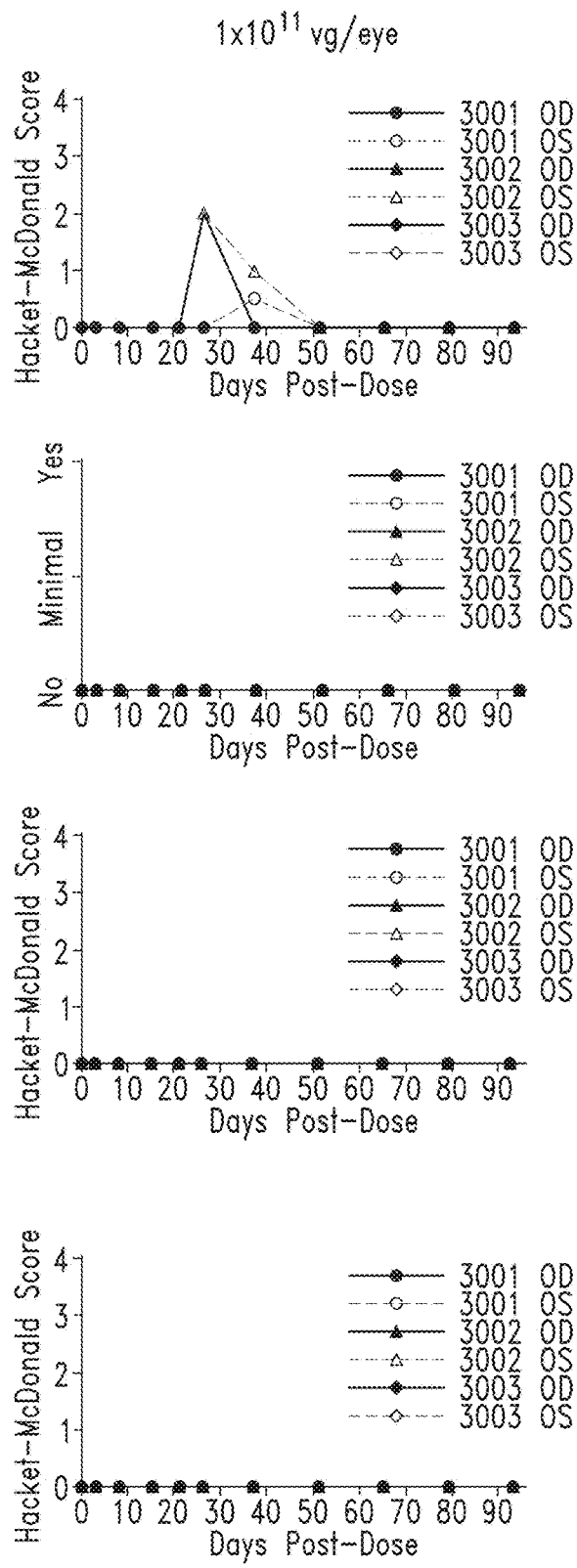
Figures 4, 13:
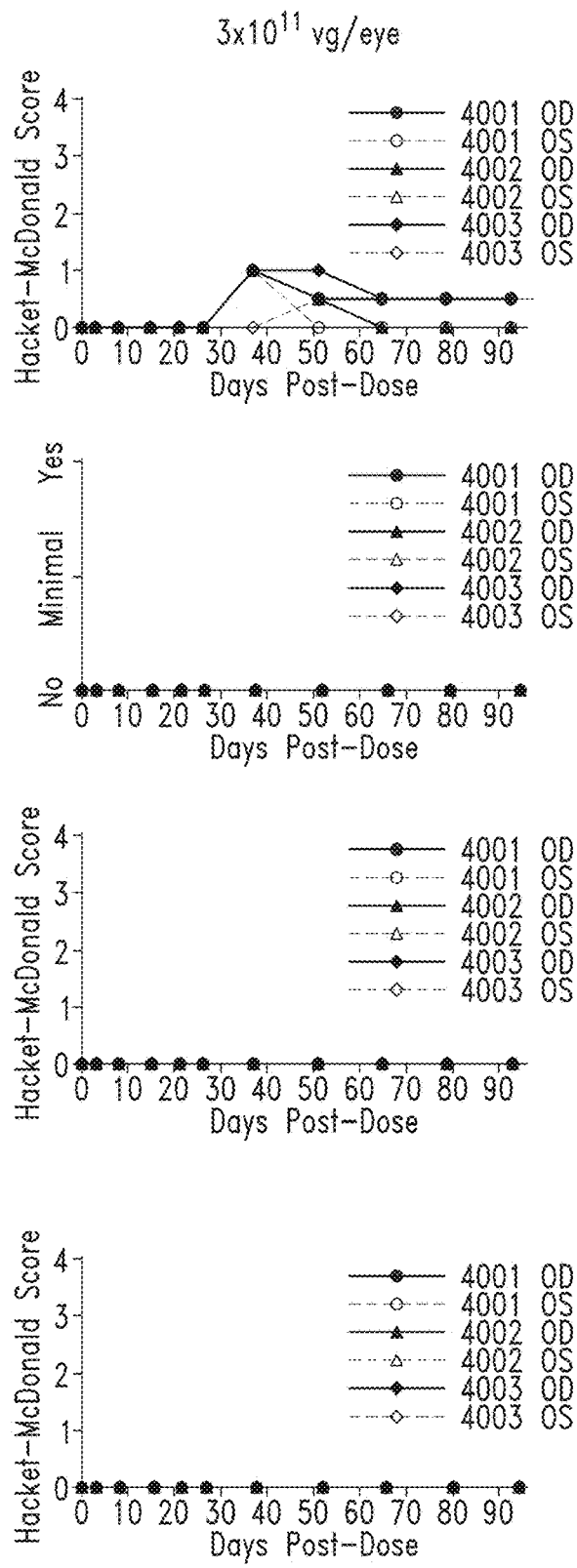
Figures 14A, 14B:
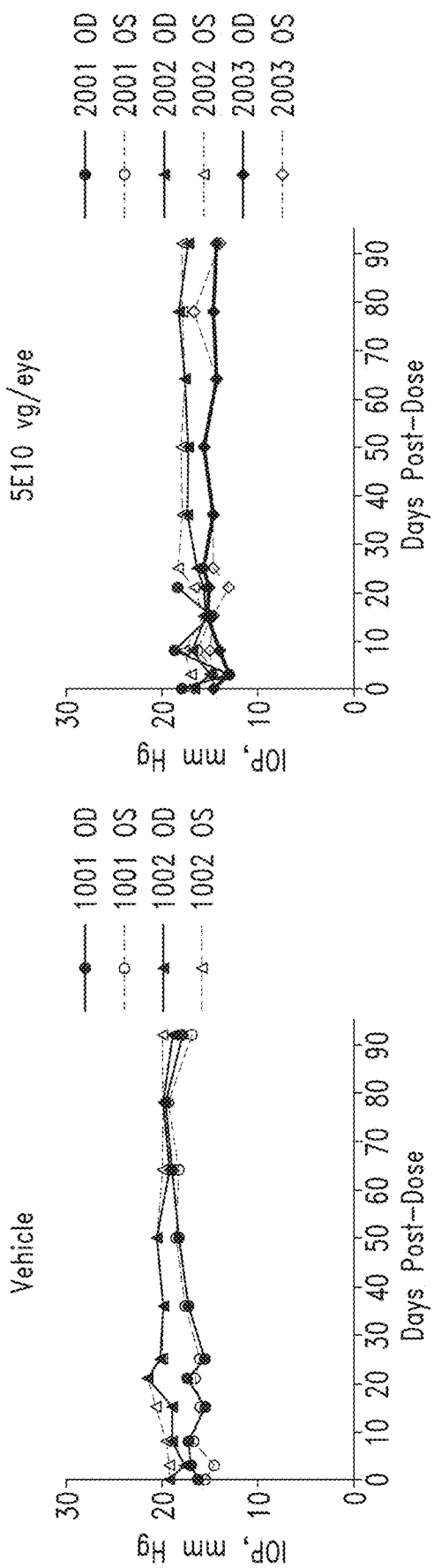
FIGS. 14A-14D show individual intraocular pressure (IOP) per dose group in NHPs IVT doses of vehicle (A) or ADVM-062 at $5\times10^{10}$ (B), $1\times10^{11}$ (C), or $3\times10^{11}$ vg/eye (D).
Figures 14C, 14D:
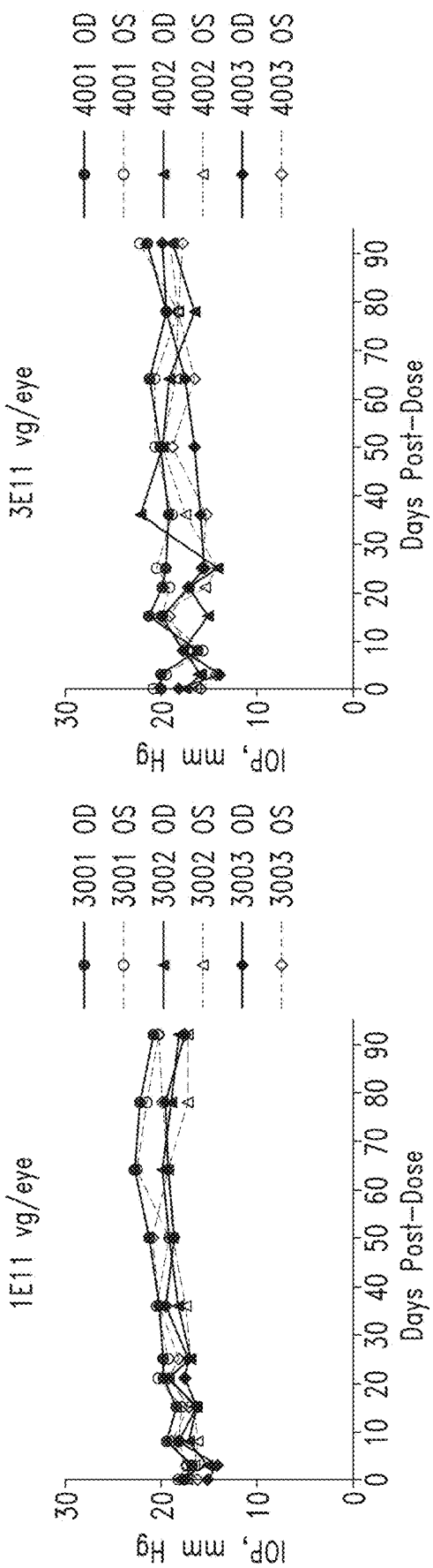

Administration of ADVM-062 at 5E10 vg/eye resulted in no ophthalmic, macroscopic, or microscopic findings. Doses of $1\times10^{11}$ vg/eye and $3\times10^{11}$ vg/eye eyes resulted in slight to mild posterior inflammation characterized by pigment and cells in the vitreous (see FIGS. 13-1 to 13-4). There were no adverse tonometry findings in all treatment groups (see FIGS. 14A-14D). ADVM-062-related microscopic findings were limited to minimal mononuclear infiltrates within the superficial optic disc which was observed in one eye of one animal from the 3E11 vg/eye dose group, which is similar to findings reported in the retina with this vector capsid. Other microscopic findings observed were considered incidental, of the nature commonly observed in cynomolgus monkeys, and/or were of similar incidence and severity in control and dosed animals and, therefore, were considered unrelated to administration of ADVM-062.

Figure 15A:
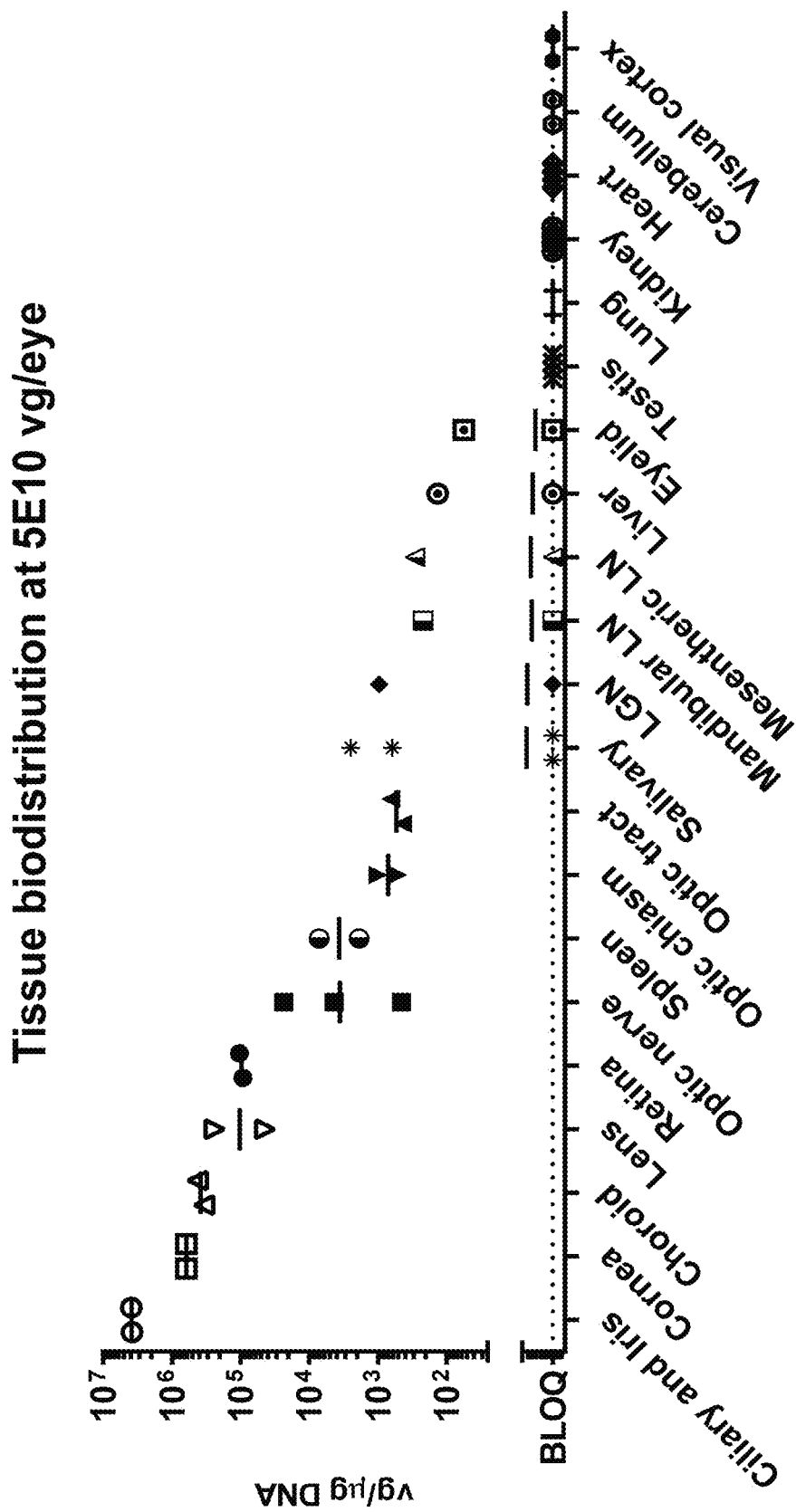
FIGS. 15A-15C show tissue distribution of ADVM-062 vector genomes (Day 97 post dose) in the animals bilaterally treated with IVT injections of ADVM-062 at $5\times10^{10}$ (A), $1\times10^{11}$ (B) and $3\times10^{11}$ (C) vg/eye.
Figure 15B:
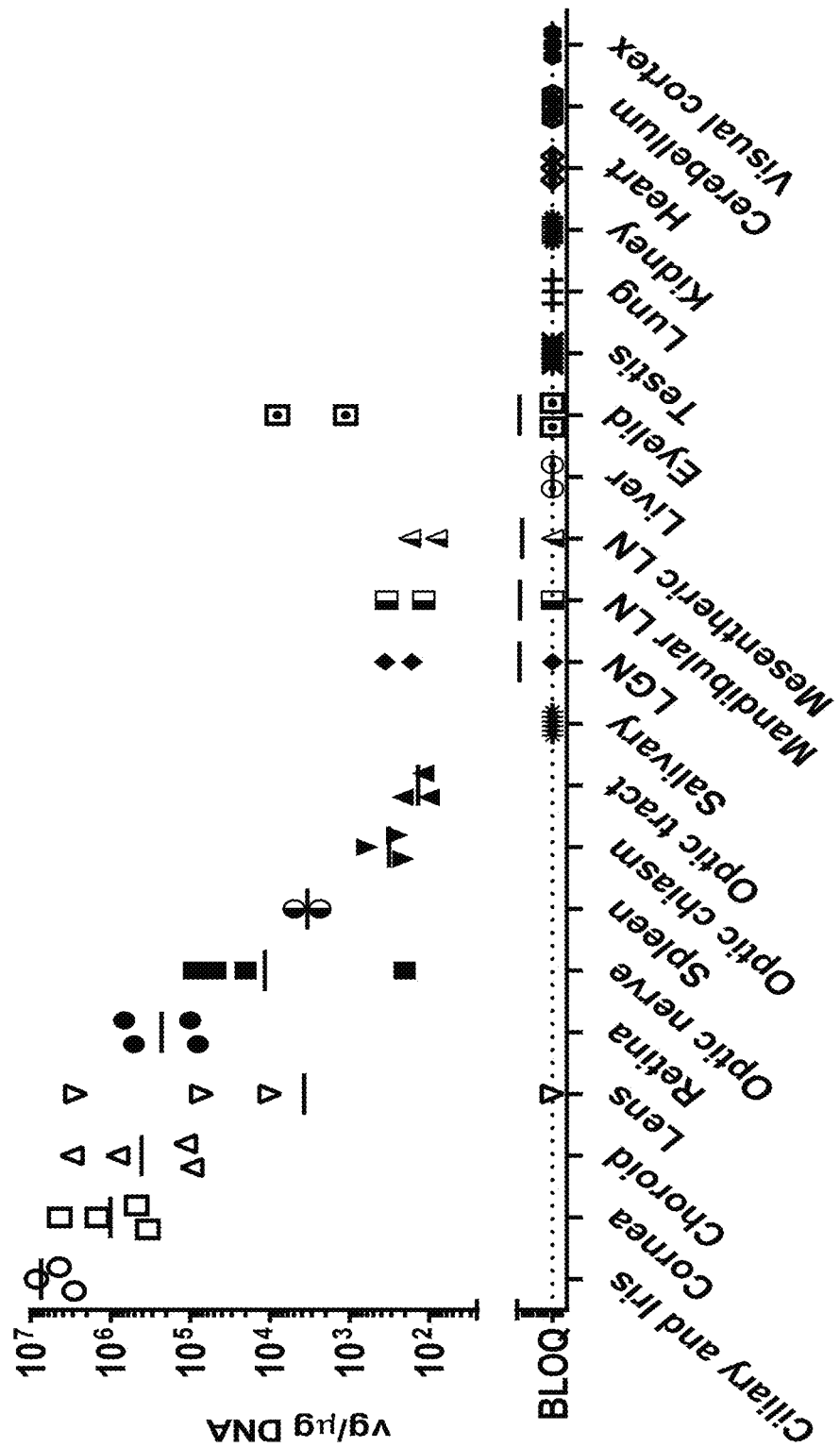
Figure 15C:
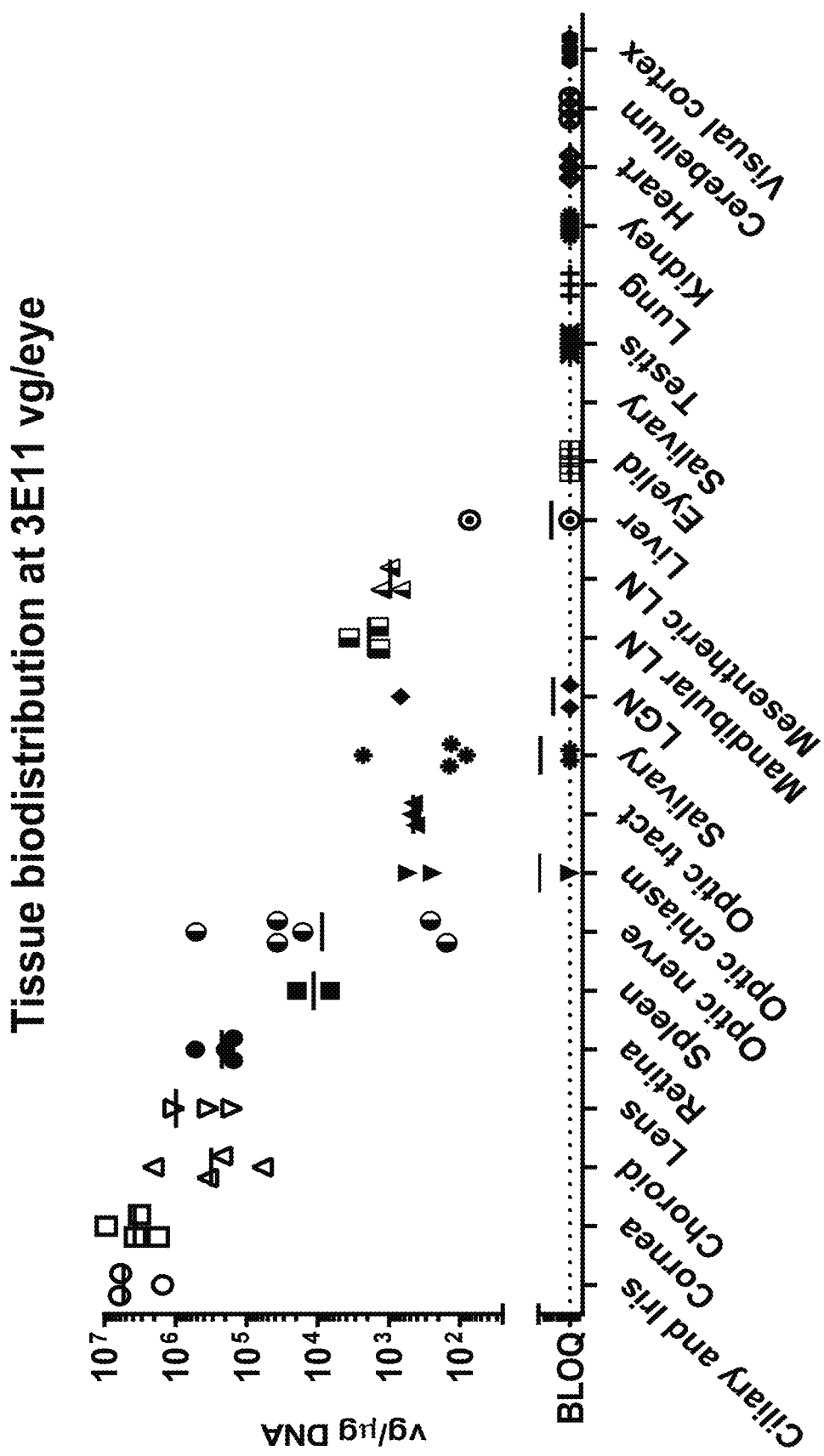
Figures 16A, 16B, 16C:
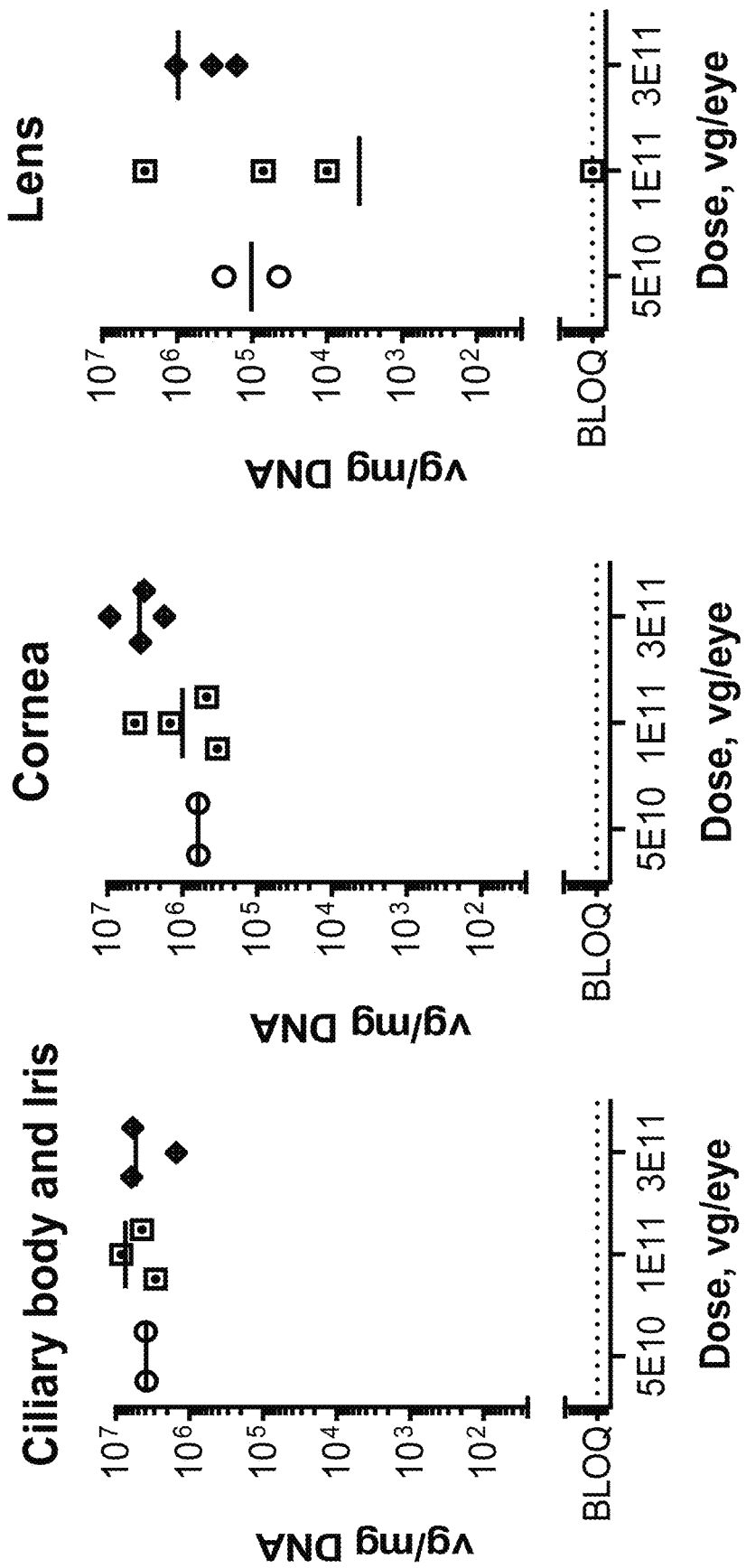
FIGS. 16A-16F show distribution of ADVM-062 vector genomes in the ocular tissues of the animals bilaterally treated with IVT injections of ADVM-062 at $5\times10^{10}$, $1\times10^{11}$, and $3\times10^{11}$ vg/eye.
Figures 16D, 16E, 16F:
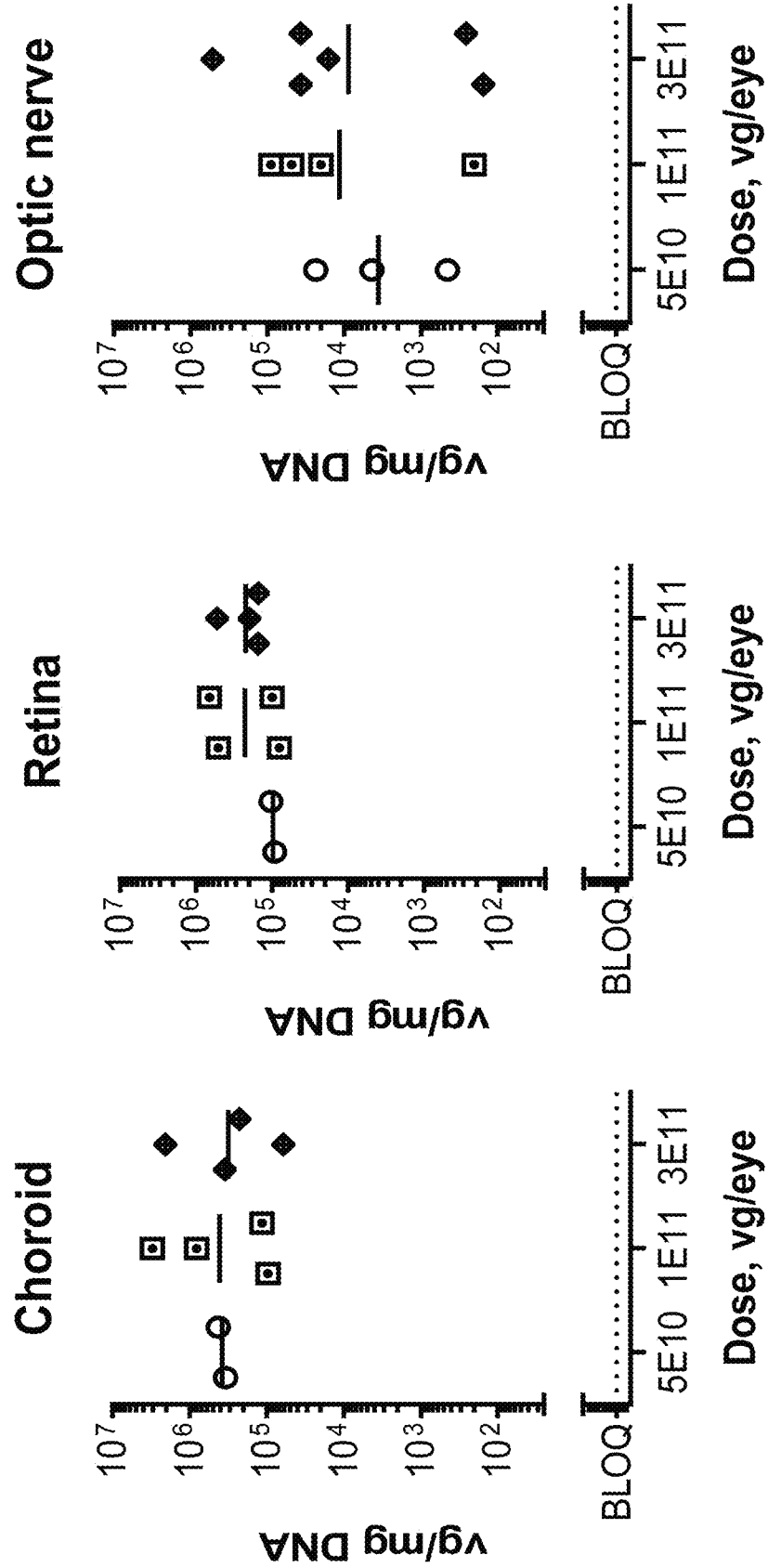

In the biodistribution study, the concentration of the ADVM-062 vector genomes was measured in ocular, CNS and systemic tissues, including retina, ciliary body and iris, choroid, lens, optic nerve, optic chiasm, lateral geniculate nucleus (LGN), optic tract, salivary gland, spleen, mandibular lymph node, mesenteric lymph node, liver, eyelid, testis, lung, kidney, heart, cerebellum, visual cortex (see FIGS. 15A-15C). Highest levels of ADVM-062 vector genomes were found in ocular tissues, as well as in the parts of visual pathway up to LGN, potentially due to the vector presence in the axons of retinal ganglion cells. In addition, presence of vector genomes were consistently detected in the lymphatic system. No significant dependency of vector genomes content in ocular tissue on the dose of vector was seen at the doses used in the study (see FIGS. 16A-16F).

In summary, IVT administration of ADVM-062 at doses of $5\times10^{10}$, $1\times10^{11}$, and $3\times10^{11}$ vg/eye were well-tolerated, supporting clinical doses for the treatment of BCM patients.

---

The invention claimed is:

1. An intravitreal dosage form, comprising a recombinant adeno-associated virus (rAAV) vector at a dosage ranging from about $1\times10^{10}$ to about $1\times10^{12}$ vector genomes (vg)/eye, wherein the rAAV vector comprises a polynucleotide comprising a human L-opsin protein coding sequence operably linked to an M-opsin promoter sequence and followed by a 3' UTR, and wherein the rAAV vector comprises an AAV2 capsid variant that transduces foveal cone photoreceptors, wherein the polynucleotide comprises a sequence that is at least 95, 98, 99, or 100% identical to the sequence set forth in SEQ ID NO: 3, and which encodes and expresses a biologically-active human L-opsin protein.

2. The intravitreal dosage form of claim 1, wherein the polynucleotide comprises, in a 5' to 3' orientation, a 5' AAV2 inverted terminal repeat (ITR), a human locus control region (LCR) enhancer sequence, a truncated M-opsin promoter sequence, a 5' untranslated region (UTR) composed of an M-opsin 5' UTR with an inserted chimeric intron and a strong Kozak sequence, the human L-opsin protein coding sequence, an M-opsin 3' UTR, an SV40 polyadenylation sequence, and a 3' AAV2 ITR.

3. The intravitreal dosage form of claim 1, wherein the AAV2 capsid variant is an AAV2.7m8 capsid or AAV2.5T.LSV1 capsid that comprises, an amino acid sequence that is at least 95, 98, 99, or 100% identical to the sequence set forth in SEQ ID NO: 1 or 2, and which transduces foveal cone photoreceptors.

4. The intravitreal dosage form of claim 1, comprising the rAAV vector at a dosage of about $5\times10^{10}$, about $1\times10^{11}$, or about $2\times10^{11}$ vg/eye, or optionally about $1\times10^{10}$, about $2\times10^{10}$, about $3\times10^{10}$, about $4\times10^{10}$, about $5\times10^{10}$, about $6\times10^{10}$, about $7\times10^{10}$, about $8\times10^{10}$, about $9\times10^{10}$, about $1\times10^{11}$, about $2\times10^{11}$, about $3\times10^{11}$, about $4\times10^{11}$, about $5\times10^{11}$, about $6\times10^{11}$, about $7\times10^{11}$, about $8\times10^{11}$, about $9\times10^{11}$, or about $1\times10^{12}$ vg/eye.

5. The intravitreal dosage form of claim 1, comprising the rAAV vector at a dosage ranging from about $1\times10^{10}$ to about $2\times10^{10}$ vg/eye, about $1\times10^{10}$ to about $3\times10^{10}$ vg/eye, about $1\times10^{10}$ to about $4\times10^{10}$ vg/eye, about $1\times10^{10}$ to about $5\times10^{10}$ vg/eye, about $1\times10^{10}$ to about $6\times10^{10}$ vg/eye, about $1\times10^{10}$ to about $7\times10^{10}$ vg/eye, about $1\times10^{10}$ to about $8\times10^{10}$ vg/eye, about $1\times10^{10}$ to about $9\times10^{10}$ vg/eye, about $1\times10^{10}$ to about $1\times10^{11}$ vg/eye, about $1\times10^{10}$ to about $2\times10^{11}$ vg/eye, about $1\times10^{10}$ to about $3\times10^{11}$ vg/eye, about $1\times10^{10}$ to about $4\times10^{11}$ vg/eye, about $1\times10^{10}$ to about $5\times10^{11}$ vg/eye, about $1\times10^{10}$ to about $6\times10^{11}$ vg/eye, about $1\times10^{10}$ to about $7\times10^{11}$ vg/eye, about $1\times10^{10}$ to about $8\times10^{11}$ vg/eye, about $1\times10^{10}$ to about $9\times10^{11}$ vg/eye, about $1\times10^{10}$ to about $1\times10^{12}$ vg/eye, about $2\times10^{10}$ to about $3\times10^{10}$ vg/eye, about $2\times10^{10}$ to about $4\times10^{10}$ vg/eye, about $2\times10^{10}$ to about $5\times10^{10}$ vg/eye, about $2\times10^{10}$ to about $6\times10^{10}$ vg/eye, about $2\times10^{10}$ to about $7\times10^{10}$ vg/eye, about $2\times10^{10}$ to about $8\times10^{10}$ vg/eye, about $2\times10^{10}$ to about $9\times10^{10}$ vg/eye, about $2\times10^{10}$ to about $1\times10^{11}$ vg/eye, about $2\times10^{10}$ to about $2\times10^{11}$ vg/eye, about $2\times10^{10}$ to about $3\times10^{11}$ vg/eye, about $2\times10^{10}$ to about $4\times10^{11}$ vg/eye, about $2\times10^{10}$ to about $5\times10^{11}$ vg/eye, about $2\times10^{10}$ to about $6\times10^{11}$ vg/eye, about $2\times10^{10}$ to about $7\times10^{11}$ vg/eye, about $2\times10^{10}$ to about $8\times10^{11}$ vg/eye, about $2\times10^{10}$ to about $9\times10^{11}$ vg/eye, about $2\times10^{10}$ to about $1\times10^{12}$ vg/eye, about $3\times10^{10}$ to about $4\times10^{10}$ vg/eye, about $3\times10^{10}$ to about $5\times10^{10}$ vg/eye, about $3\times10^{10}$ to about $6\times10^{10}$ vg/eye, about $3\times10^{10}$ to about $7\times10^{10}$ vg/eye, about $3\times10^{10}$ to about $8\times10^{10}$ vg/eye, about $3\times10^{10}$ to about $9\times10^{10}$ vg/eye, about $3\times10^{10}$ to about $1\times10^{11}$ vg/eye, about $3\times10^{10}$ to about $2\times10^{11}$ vg/eye, about $3\times10^{10}$ to about $3\times10^{11}$ vg/eye, about $3\times10^{10}$ to about $4\times10^{11}$ vg/eye, about $3\times10^{10}$ to about $5\times10^{11}$ vg/eye, about $3\times10^{10}$ to about $6\times10^{11}$ vg/eye, about $3\times10^{10}$ to about $7\times10^{11}$ vg/eye, about $3\times10^{10}$ to about $8\times10^{11}$ vg/eye, about $3\times10^{10}$ to about $9\times10^{11}$ vg/eye, about $3\times10^{10}$ to about $1\times10^{12}$ vg/eye, about $4\times10^{10}$ to about $5\times10^{10}$ vg/eye, about $4\times10^{10}$ to about $6\times10^{10}$ vg/eye, about $4\times10^{10}$ to about $7\times10^{10}$ vg/eye, about $4\times10^{10}$ to about $8\times10^{10}$ vg/eye, about $4\times10^{10}$ to about $9\times10^{10}$ vg/eye, about $4\times10^{10}$ to about $1\times10^{11}$ vg/eye, about $4\times10^{10}$ to about $2\times10^{11}$ vg/eye, about $4\times10^{10}$ to about $3\times10^{11}$ vg/eye, about $4\times10^{10}$ to about $4\times10^{11}$ vg/eye, about $4\times10^{10}$ to about $5\times10^{11}$ vg/eye, about $4\times10^{10}$ to about $6\times10^{11}$ vg/eye, about $4\times10^{10}$ to about $7\times10^{11}$ vg/eye, about $4\times10^{10}$ to about $8\times10^{11}$ vg/eye, about $4\times10^{10}$ to about $9\times10^{11}$ vg/eye, about $4\times10^{10}$ to about $1\times10^{12}$ vg/eye, about $5\times10^{10}$ to about $6\times10^{10}$ vg/eye, about $5\times10^{10}$ to about $7\times10^{10}$ vg/eye, about $5\times10^{10}$ to about $8\times10^{10}$ vg/eye, about $5\times10^{10}$ to about $9\times10^{10}$ vg/eye, about $5\times10^{10}$ to about $1\times10^{11}$ vg/eye, about $5\times10^{10}$ to about $2\times10^{11}$ vg/eye, about $5\times10^{10}$ to about $3\times10^{11}$ vg/eye, about $5\times10^{10}$ to about $4\times10^{11}$ vg/eye, about $5\times10^{10}$ to about $5\times10^{11}$ vg/eye, about $5\times10^{10}$ to about $6\times10^{11}$ vg/eye, about $5\times10^{10}$ to about $7\times10^{11}$ vg/eye, about $5\times10^{10}$ to about $8\times10^{11}$ vg/eye, about $5\times10^{10}$ to about $9\times10^{11}$ vg/eye, about $5\times10^{10}$ to about $1\times10^{12}$ vg/eye, about $6\times10^{10}$ to about $7\times10^{10}$ vg/eye, about $6\times10^{10}$ to about $8\times10^{10}$ vg/eye, about $6\times10^{10}$ to about $9\times10^{10}$ vg/eye, about $6\times10^{10}$ to about $1\times10^{11}$ vg/eye, about $6\times10^{10}$ to about $2\times10^{11}$ vg/eye, about $6\times10^{10}$ to about $3\times10^{11}$ vg/eye, about $6\times10^{10}$ to about $4\times10^{11}$ vg/eye, about $6\times10^{10}$ to about $5\times10^{11}$ vg/eye, about $6\times10^{10}$ to about $6\times10^{11}$ vg/eye, about $6\times10^{10}$ to about $7\times10^{11}$ vg/eye, about $6\times10^{10}$ to about $8\times10^{11}$ vg/eye, about $6\times10^{10}$ to about $9\times10^{11}$ vg/eye, about $6\times10^{10}$ to about $1\times10^{12}$ vg/eye, about $7\times10^{10}$ to about $8\times10^{10}$ vg/eye, about $7\times10^{10}$ to about $9\times10^{10}$ vg/eye, about $7\times10^{10}$ to about $1\times10^{11}$ vg/eye, about $7\times10^{10}$ to about $2\times10^{11}$ vg/eye, about $7\times10^{10}$ to about $3\times10^{11}$ vg/eye, about $7\times10^{10}$ to about $4\times10^{11}$ vg/eye, about $7\times10^{10}$ to about $5\times10^{11}$ vg/eye, about $7\times10^{10}$ to about $6\times10^{11}$ vg/eye, about $7\times10^{10}$ to about $7\times10^{11}$ vg/eye, about $7\times10^{10}$ to about $8\times10^{11}$ vg/eye, about $7\times10^{10}$ to about $9\times10^{11}$ vg/eye, about $7\times10^{10}$ to about $1\times10^{12}$ vg/eye, about $8\times10^{10}$ to about $9\times10^{10}$ vg/eye, about $8\times10^{10}$ to about $1\times10^{11}$ vg/eye, about $8\times10^{10}$ to about $2\times10^{11}$ vg/eye, about $8\times10^{10}$ to about $3\times10^{11}$ vg/eye, about $8\times10^{10}$ to about $4\times10^{11}$ vg/eye, about $8\times10^{10}$ to about $5\times10^{11}$ vg/eye, about $8\times10^{10}$ to about $6\times10^{11}$ vg/eye, about $8\times10^{10}$ to about $7\times10^{11}$ vg/eye, about $8\times10^{10}$ to about $8\times10^{11}$ vg/eye, about $8\times10^{10}$ to about $9\times10^{11}$ vg/eye, about $8\times10^{10}$ to about $1\times10^{12}$ vg/eye, about $9\times10^{10}$ to about $1\times10^{11}$ vg/eye, about $9\times10^{10}$ to about $2\times10^{11}$ vg/eye, about $9\times10^{10}$ to about $3\times10^{11}$ vg/eye, about $9\times10^{10}$ to about $4\times10^{11}$ vg/eye, about $9\times10^{10}$ to about $5\times10^{11}$ vg/eye, about $9\times10^{10}$ to about $6\times10^{11}$ vg/eye, about $9\times10^{10}$ to about $7\times10^{11}$ vg/eye, about $9\times10^{10}$ to about $8\times10^{11}$ vg/eye, about $9\times10^{10}$ to about $9\times10^{11}$ vg/eye, about $9\times10^{10}$ to about $1\times10^{12}$ vg/eye, about $1\times10^{11}$ to about $2\times10^{11}$ vg/eye, about $1\times10^{11}$ to about $3\times10^{11}$ vg/eye, about $1\times10^{11}$ to about $4\times10^{11}$ vg/eye, about $1\times10^{11}$ to about $5\times10^{11}$ vg/eye, about $1\times10^{11}$ to about $6\times10^{11}$ vg/eye, about $1\times10^{11}$ to about $7\times10^{11}$ vg/eye, about $1\times10^{11}$ to about $8\times10^{11}$ vg/eye, about $1\times10^{11}$ to about $9\times10^{11}$ vg/eye, about $1\times10^{11}$ to about $1\times10^{12}$ vg/eye, about $2\times10^{11}$ to about $3\times10^{11}$ vg/eye, about $2\times10^{11}$ to about $4\times10^{11}$ vg/eye, about $2\times10^{11}$ to about $5\times10^{11}$ vg/eye, about $2\times10^{11}$ to about $6\times10^{11}$ vg/eye, about $2\times10^{11}$ to about $7\times10^{11}$ vg/eye, about $2\times10^{11}$ to about $8\times10^{11}$ vg/eye, about $2\times10^{11}$ to about $9\times10^{11}$ vg/eye, about $2\times10^{11}$ to about $1\times10^{12}$ vg/eye, about $3\times10^{11}$ to about $4\times10^{11}$ vg/eye, about $3\times10^{11}$ to about $5\times10^{11}$ vg/eye, about $3\times10^{11}$ to about $6\times10^{11}$ vg/eye, about $3\times10^{11}$ to about $7\times10^{11}$ vg/eye, about $3\times10^{11}$ to about $8\times10^{11}$ vg/eye, about $3\times10^{11}$ to about $9\times10^{11}$ vg/eye, about $3\times10^{11}$ to about $1\times10^{12}$ vg/eye, about $4\times10^{11}$ to about $5\times10^{11}$ vg/eye, about $4\times10^{11}$ to about $6\times10^{11}$ vg/eye, about $4\times10^{11}$ to about $7\times10^{11}$ vg/eye, about $4\times10^{11}$ to about $8\times10^{11}$ vg/eye, about $4\times10^{11}$ to about $9\times10^{11}$ vg/eye, about $4\times10^{11}$ to about $1\times10^{12}$ vg/eye, about $5\times10^{11}$ to about $6\times10^{11}$ vg/eye, about $5\times10^{11}$ to about $7\times10^{11}$ vg/eye, about $5\times10^{11}$ to about $8\times10^{11}$ vg/eye, about $5\times10^{11}$ to about $9\times10^{11}$ vg/eye, about $5\times10^{11}$ to about $1\times10^{12}$ vg/eye, about $6\times10^{11}$ to about $7\times10^{11}$ vg/eye, about $6\times10^{11}$ to about $8\times10^{11}$ vg/eye, about $6\times10^{11}$ to about $9\times10^{11}$ vg/eye, about $6\times10^{11}$ to about $1\times10^{12}$ vg/eye, about $7\times10^{11}$ to about $8\times10^{11}$ vg/eye, about $7\times10^{11}$ to about $9\times10^{11}$ vg/eye, about $7\times10^{11}$ to about $1\times10^{12}$ vg/eye, about $8\times10^{11}$ to about $9\times10^{11}$ vg/eye, about $8\times10^{11}$ to about $1\times10^{12}$ vg/eye, or about $9\times10^{11}$ to about $1\times10^{12}$ vg/eye.

6. The intravitreal dosage form of claim 5, comprising the rAAV vector at a dosage ranging from about $6\times10^{10}$ to about $6\times10^{11}$ vg/eye.

7. The intravitreal dosage form of claim 6, comprising the rAAV vector at a dosage of about $6\times10^{10}$, about $7\times10^{10}$, about $8\times10^{10}$, about $9\times10^{10}$, about $1\times10^{11}$ vg/eye, about $2\times10^{11}$ vg/eye, about $3\times10^{11}$ vg/eye, about $4\times10^{11}$ vg/eye, about $5\times10^{11}$ vg/eye, or about $6\times10^{11}$ vg/eye.

8. The intravitreal dosage form of claim 6, comprising the rAAV vector at a dosage ranging from about $6\times10^{10}$ to about $7\times10^{10}$ vg/eye, about $6\times10^{10}$ to about $8\times10^{10}$ vg/eye, about $6\times10^{10}$ to about $9\times10^{10}$ vg/eye, about $6\times10^{10}$ to about $1\times10^{11}$ vg/eye, about $6\times10^{10}$ to about $2\times10^{11}$ vg/eye, about $6\times10^{10}$ to about $3\times10^{11}$ vg/eye, about $6\times10^{10}$ to about $4\times10^{11}$ vg/eye, about $6\times10^{10}$ to about $5\times10^{11}$ vg/eye, about $6\times10^{10}$ to about $6\times10^{11}$ vg/eye, about $7\times10^{10}$ to about $8\times10^{10}$ vg/eye, about $7\times10^{10}$ to about $9\times10^{10}$ vg/eye, about $7\times10^{10}$ to about $1\times10^{11}$ vg/eye, about $7\times10^{10}$ to about $2\times10^{11}$ vg/eye, about $7\times10^{10}$ to about $3\times10^{11}$ vg/eye, about $7\times10^{10}$ to about $4\times10^{11}$ vg/eye, about $7\times10^{10}$ to about $5\times10^{11}$ vg/eye, about $7\times10^{10}$ to about $6\times10^{11}$ vg/eye, about $8\times10^{10}$ to about $9\times10^{10}$ vg/eye, about $8\times10^{10}$ to about $1\times10^{11}$ vg/eye, about $8\times10^{10}$ to about $2\times10^{11}$ vg/eye, about $8\times10^{10}$ to about $3\times10^{11}$ vg/eye, about $8\times10^{10}$ to about $4\times10^{11}$ vg/eye, about $8\times10^{10}$ to about $5\times10^{11}$ vg/eye, about $8\times10^{10}$ to about $6\times10^{11}$ vg/eye, about $9\times10^{10}$ to about $1\times10^{11}$ vg/eye, about $9\times10^{10}$ to about $2\times10^{11}$ vg/eye, about $9\times10^{10}$ to about $3\times10^{11}$ vg/eye, about $9\times10^{10}$ to about $4\times10^{11}$ vg/eye, about $9\times10^{10}$ to about $5\times10^{11}$ vg/eye, about $9\times10^{10}$ to about $6\times10^{11}$ vg/eye, about $1\times10^{11}$ to about $2\times10^{11}$ vg/eye, about $1\times10^{11}$ to about $3\times10^{11}$ vg/eye, about $1\times10^{11}$ to about $4\times10^{11}$ vg/eye, about $1\times10^{11}$ to about $5\times10^{11}$ vg/eye, about $1\times10^{11}$ to about $6\times10^{11}$ vg/eye, about $2\times10^{11}$ to about $3\times10^{11}$ vg/eye, about $2\times10^{11}$ to about $4\times10^{11}$ vg/eye, about $2\times10^{11}$ to about $5\times10^{11}$ vg/eye, about $2\times10^{11}$ to about $6\times10^{11}$ vg/eye, about $3\times10^{11}$ to about $4\times10^{11}$ vg/eye, about $3\times10^{11}$ to about $5\times10^{11}$ vg/eye, about $3\times10^{11}$ to about $6\times10^{11}$ vg/eye, about $4\times10^{11}$ to about $5\times10^{11}$ vg/eye, about $4\times10^{11}$ to about $6\times10^{11}$ vg/eye, or about $5\times10^{11}$ to about $6\times10^{11}$ vg/eye.

* * * * *